(12) United States Patent
Murata et al.

(10) Patent No.: US 7,989,445 B2
(45) Date of Patent: Aug. 2, 2011

(54) THIENOPYRIMIDONE COMPOUND

(75) Inventors: Toshiki Murata, Osaka (JP); Shingo Makino, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 604 days.

(21) Appl. No.: 11/919,301

(22) PCT Filed: Apr. 27, 2006

(86) PCT No.: PCT/JP2006/309201
§ 371 (c)(1),
(2), (4) Date: Oct. 25, 2007

(87) PCT Pub. No.: WO2006/118320
PCT Pub. Date: Nov. 9, 2006

(65) Prior Publication Data
US 2010/0069362 A1    Mar. 18, 2010

(30) Foreign Application Priority Data
Apr. 28, 2005 (JP) ................................. 2005-132652

(51) Int. Cl.
A61K 31/55    (2006.01)
A61K 31/519   (2006.01)
A61P 3/04     (2006.01)
C07D 495/04   (2006.01)

(52) U.S. Cl. .............. 514/217.01; 514/247; 514/252.16; 540/594; 544/278

(58) Field of Classification Search .................. None
See application file for complete search history.

(56) References Cited

U.S. PATENT DOCUMENTS

| | | | |
|---|---|---|---|
| 2003/0158177 A1 | 8/2003 | Ishihara et al. | |
| 2004/0077628 A1 | 4/2004 | Ishihara et al. | |
| 2004/0220404 A1* | 11/2004 | Carpenter et al. | 544/184 |
| 2005/0209213 A1 | 9/2005 | Ishihara et al. | |
| 2006/0128690 A1 | 6/2006 | Ishihara et al. | |

FOREIGN PATENT DOCUMENTS

| | | |
|---|---|---|
| EP | 1283199 | 2/2003 |
| EP | 1285651 | 2/2003 |
| EP | 1447402 | 8/2004 |
| WO | WO 01/21577 A2 | 3/2001 |
| WO | WO 03/033476 A1 | 4/2003 |
| WO | WO 2004/092181 A1 | 10/2004 |

OTHER PUBLICATIONS

Stella, Valentino. J. Expert Opinion of Therapeutic Patents, Prodrugs as therapeutics, 2004, 14(3): 277-280.*
Testa, Bernard. Biochemical Pharmacology, Prodrug Research: futile or fertile?. 68(2004): 2097-2106.*
Ettmayer, Peter. Medicinal Chemistry, Lessons Learned from Marketed and Investigational Prodrugs, 47(10), 2004: 2394-2404.*
Schaefer et al. Failure is not an option: learning from unsucessful proof-of-concept trials. Drug Discovery Today, 2008, 13: (21/22), 913-916.*
Horig et al. Review: from bench to clinic and back: Perspective on the 1st IQPC Translational Research Conference. Journal of Translational Medicine, 2004, 2(44).*
J.G. Cannon. Chapter Nineteen in Burger's Medicinal Chemistry and Drug Discovery, Fifth Edition, vol. I: Principles and Practice, Wiley-Interscience, 1995, pp. 783-802.*
Meyer et al. Structure-activity studies for a novel series of bicyclic substituted hexahydrobenz[e]isoindole alpha1A adrenoceptor antagonist as potential agents for the symptomatic treatment of benign prostatic hyperplasia. J. Med. Chem. 2001, 44, 1971-1985.*
Friedman et al. Leptin and the regulation of body weight in mammals. Nature. vol. 395, 1996.*
Search Report for Corresponding European Application No. 06746033.7 dated Aug. 11, 2009.

* cited by examiner

*Primary Examiner* — Brandon Fetterolf
*Assistant Examiner* — Anna Pagonakis
(74) *Attorney, Agent, or Firm* — David G. Conlin; Dwight D. Kim; Edwards Angell Palmer & Dodge LLP

(57) ABSTRACT

The present invention relates to a compound represented by the formula:

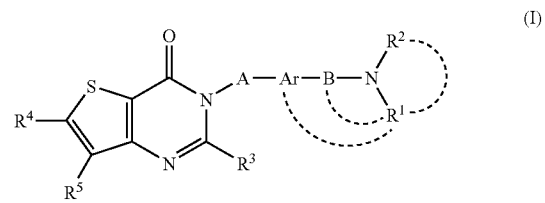

wherein
Ar is an optionally substituted ring;
A is a spacer having a main chain of 1 to 4 atoms;
B is a bond, a $C_{1-10}$ alkylene group or an oxygen atom;
$R^3$ and $R^5$ are each independently a hydrogen atom or a substituent;
$R^4$ is an optionally substituted cyclic group or an optionally substituted $C_{1-10}$ alkyl group; and
$R^1$ and $R^2$ are each independently a hydrogen atom or a substituent, or
$R^1$ and $R^2$ or $R^1$ and B are bonded to form an optionally substituted nitrogen-containing heterocycle, or
$R^1$ and Ar are bonded to form an optionally substituted nitrogen-containing fused heterocycle, or a salt thereof. The thienopyrimidone compound of the present invention has a superior melanin-concentrating hormone receptor antagonistic action, and is useful as an agent for the prophylaxis or treatment of obesity and the like.

8 Claims, No Drawings

THIENOPYRIMIDONE COMPOUND

TECHNICAL FIELD

The present invention relates to a thienopyrimidone compound having superior melanin-concentrating hormone (hereinafter sometimes abbreviated as MCH) receptor antagonistic action, and useful as an agent for the prophylaxis or treatment of obesity and the like.

BACKGROUND ART

MCH receptor antagonists are to be anorexigenic agents or antiobesity agents, and as concrete examples thereof, the following compounds have been reported.
1) A compound represented by the formula

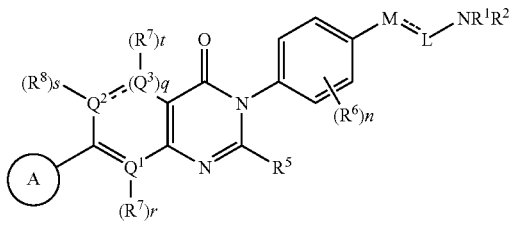

wherein ring A is an optionally substituted aryl or heteroaryl; q, r, s and t are each independently 0 or 1; $Q^1$ and $Q^3$ are each independently C or N; $Q^2$ is N, S, O or C; when $Q^1$ or $Q^3$ is C, $R^7$ is a hydrogen atom, $C_{1-6}$ alkyl or the like; $R^5$ is a hydrogen atom, $C_{1-6}$ alkyl or the like; $R^6$ is a hydrogen atom, $C_{1-6}$ alkyl or the like; M is O, S, $S(O)_2$, $S(O)_2NR$, N—R, C(O), $C(R)_2$, N—C(O)R or N—$S(O)_2R$ (R is a hydrogen atom, phenyl, heteroaryl, $C_{1-6}$ alkyl or $C_{3-6}$ cycloalkyl); L is $C_{2-3}$ alkyl, $C_{2-3}$ alkenyl or —C(O)($CH_2$)—; and $R^1$ and $R^2$ are each independently a hydrogen atom, $C_{1-6}$ alkyl or the like (see WO03/033476).
2) A compound represented by the formula

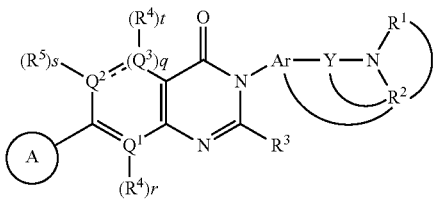

wherein ring A is an optionally substituted aryl or heteroaryl; q, r, s and t are each independently 0 or 1; $Q^1$ and $Q^3$ are each independently C or N; $Q^2$ is N, S, O or C; when $Q^1$ or $Q^3$ is C, $R^4$ is a hydrogen atom, $C_{1-6}$ alkyl or the like; $R^3$ is a hydrogen atom, $C_{1-6}$ alkyl or the like; $R^5$ is a hydrogen atom, $C_{1-6}$ alkyl or the like; Ar is an optionally substituted bicyclic fused ring; Y is a bond or an optionally substituted $C_{1-6}$ alkylene; and $R^1$ and $R^2$ are each independently a hydrogen atom, $C_{1-6}$ alkyl or the like (see WO2004/092181).
3) A compound represented by the formula

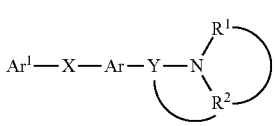

wherein $Ar^1$ is a cyclic group which may have substituents; X is a spacer having a main chain of 1 to 6 atoms; Y is a bond or a spacer having a main chain of 1 to 6 atoms; Ar is a monocyclic aromatic ring which may be condensed with a 4 to 8 membered non-aromatic ring, and may have further substituents; and $R^1$ and $R^2$ are the same or different and each is a hydrogen atom or a hydrocarbon group which may have substituents; or $R^1$ and $R^2$, together with the adjacent nitrogen atom, may form a nitrogen-containing heterocycle which may have substituents; or $R^2$ may form a spiro ring together with Ar; or $R^2$, together with the adjacent nitrogen atom and Y, may form a nitrogen-containing heterocycle which may have substituents (see WO01/21577).
4) A compound represented by the formula

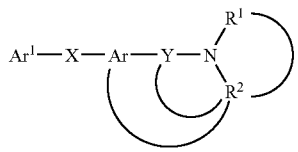

wherein $Ar^1$ is a cyclic group which may be substituted;

X and Y are the same or different and each is a spacer having a main chain of 1 to 6 atoms;

Ar is a condensed polycyclic aromatic ring which may be substituted; and $R^1$ and $R^2$ are the same or different and each is a hydrogen atom or a hydrocarbon group which may be substituted; or $R^1$ and $R^2$, together with the adjacent nitrogen atom, may form a nitrogen-containing heterocycle which may be substituted; or $R^2$, together with the adjacent nitrogen atom and Y, may form a nitrogen-containing heterocycle which may be substituted; or $R^2$, together with the adjacent nitrogen atom, Y and Ar, may form a condensed ring (see WO01/82925).

5) A compound represented by the formula

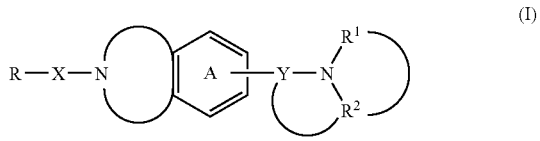

(I)

wherein R is hydrogen atom, a halogen atom or a cyclic group which may be substituted;

X is a bond or a spacer having a main chain of 1 to 10 atoms;

Y is a spacer having a main chain of 1 to 6 atoms;

ring A is benzene ring which may be further substituted;

ring B is a 5- to 9-membered nitrogen-containing non-aromatic heterocycle which may be further substituted; and $R^1$ and $R^2$ are the same or different and each is a hydrogen atom, a hydrocarbon group which may be substituted or a heterocyclic group which may be substituted; or $R^1$ and $R^2$, together with the adjacent nitrogen atom, may form a nitrogen-containing heterocycle which may be substituted; or $R^2$, together with the adjacent nitrogen atom and Y, may form a nitrogen-containing heterocycle which may be substituted (see WO01/87834).

6) A compound represented by the formula

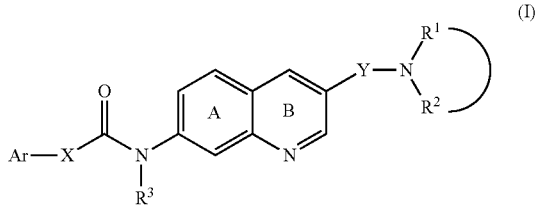

wherein Ar is a cyclic group optionally having substituent(s);
X is a bond or a spacer having a main chain of 1 to 6 atoms;
$R^1$ and $R^2$ are the same or different and each is a hydrogen atom or a hydrocarbon group optionally having substituent(s), or $R^1$ and $R^2$ may form, together with the adjacent nitrogen atom, a nitrogen-containing heterocycle optionally having substituent(s);
Y is a divalent hydrocarbon group optionally having substituent(s) (except CO);
$R^3$ is a hydrogen atom or a hydrocarbon group optionally having substituent(s); and
ring A and ring B may further have substituent(s), and when ring B further has a substituent, the substituent may be linked to $R^1$ to form a ring (see WO03/35624).

7) A compound represented by the formula

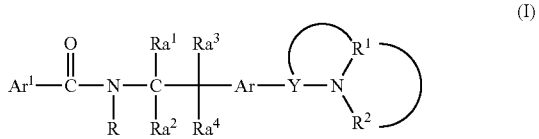

wherein
$Ar^1$ is a cyclic group optionally having substituent(s);
R is a hydrogen atom, an optionally halogenated $C_{1-6}$ alkyl, a phenyl optionally having substituent(s) or a pyridyl optionally having substituent(s);
$Ra^1$, $Ra^2$, $Ra^3$ and $Ra^4$ are the same or different and each is a hydrogen atom, an optionally halogenated $C_{1-6}$ alkyl, a phenyl optionally having substituent(s), a halogen atom, a pyridyl optionally having substituent(s), a cyano, an optionally halogenated $C_{1-6}$ alkoxy, an optionally halogenated $C_{1-6}$ alkylthio, an amino, a mono- or di-$C_{1-6}$ alkylamino, a formyl, an optionally halogenated $C_{1-6}$ alkylcarbonyl or an optionally halogenated $C_{1-6}$ alkylsulfonyl;
Ar is a monocyclic aromatic ring optionally having substituent(s);
Y is an optionally halogenated alkylene group; and
$R^1$ and $R^2$ are (1) the same or different and each is a hydrogen atom or a $C_{1-6}$ alkyl, (2) $R^1$ and $R^2$ form a nitrogen-containing heterocycle optionally having substituent(s) together with the adjacent nitrogen atom, or (3) $R^1$ and Y form a nitrogen-containing heterocycle optionally having substituent(s) together with the adjacent nitrogen atom, and $R^2$ is a hydrogen atom or a $C_{1-6}$ alkyl;
provided that when the nitrogen-containing heterocycle formed by $R^1$ and $R^2$ together with the adjacent nitrogen atom is a piperazine, or when R is a $C_{1-4}$ alkyl, $Ar^1$ is a cyclic group having substituent(s) (see WO2004/072018).

However, the compound of the present invention has not been reported.

DISCLOSURE OF THE INVENTION

There is a demand for the development of a compound having superior melanin-concentrating hormone receptor antagonistic action, which is useful as an agent for the prophylaxis or treatment of obesity and lower toxic.

The present inventors have conducted intensive studies of compounds having an MCH receptor antagonistic action and, as a result, have found that a compound represented by the formula:

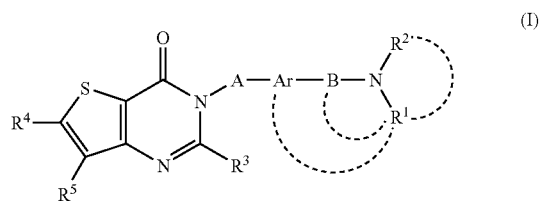

wherein
Ar is an optionally substituted ring;
A is a spacer having a main chain of 1 to 4 atoms;
B is a bond, a $C_{1-10}$ alkylene group or an oxygen atom;
$R^3$ and $R^5$ are each independently a hydrogen atom or a substituent;
$R^4$ is an optionally substituted cyclic group or an optionally substituted $C_{1-10}$ alkyl group; and
$R^1$ and $R^2$ are each independently a hydrogen atom or a substituent, or
$R^1$ and $R^2$ or $R^1$ and B are bonded to form an optionally substituted nitrogen-containing heterocycle, or
$R^1$ and Ar are bonded to form an optionally substituted nitrogen-containing fused heterocycle, or a salt thereof [hereinafter sometimes to be abbreviated as compound (I)] has a superior MCH receptor antagonistic action, which resulted in the completion of the present invention.

Accordingly, the present invention relates to
1) compound (I);
2) compound (I) wherein Ar is benzene or indane;
3) compound (I) wherein A is a $C_{1-4}$ alkylene group optionally substituted by 1 or 2 substituents selected from an oxo group and a hydroxy group;
4) compound (I) wherein B is a bond or a $C_{1-10}$ alkylene group;
5) compound (I) wherein $R^3$ is a hydrogen atom;
6) compound (I) wherein $R^5$ is a hydrogen atom;
7) compound (I) wherein $R^4$ is a phenyl group optionally substituted by 1 to 3 substituents selected from a halogen atom and a hydroxy group;
8) compound (I) wherein $R^1$ and $R^2$ are each independently
(1) a hydrogen atom;
(2) a $C_{1-6}$ alkyl group optionally substituted by 1 to 3 substituents selected from halogen atom, carboxy group, hydroxy group, $C_{1-6}$ alkoxy-carbonyl group, and carbamoyl group optionally mono- or di-substituted by $C_{1-6}$ alkyl group;
(3) an amino group optionally substituted by 1 or 2 substituents selected from $C_{1-6}$ alkyl group, $C_{1-6}$ alkyl-carbonyl group, $C_{1-6}$ alkoxy-carbonyl group, $C_{6-14}$ aryl-carbonyl group, $C_{7-13}$ aralkyl-carbonyl group, $C_{1-6}$ alkylsulfonyl group, $C_{6-14}$ arylsulfonyl group and $C_{7-13}$ aralkylsulfonyl group;
(4) a $C_{1-6}$ alkyl-carbonyl group optionally substituted by 1 to 3 substituents selected from halogen atom, and amino group optionally mono- or di-substituted by $C_{1-6}$ alkyl group;

(5) a $C_{3-10}$ cycloalkyl-carbonyl group;
(6) a $C_{1-6}$ alkoxy-carbonyl group optionally substituted by 1 to 3 halogen atoms;
(7) a $C_{1-6}$ alkylsulfonyl group optionally substituted by 1 to 3 halogen atoms;
(8) a carbamoyl group optionally substituted by 1 or 2 substituents selected from $C_{1-6}$ alkyl group optionally substituted by 1 to 3 halogen atoms, $C_{6-14}$ aryl group and $C_{7-13}$ aralkyl group; or
(9) a thiocarbamoyl group optionally mono- or di-substituted by $C_{1-6}$ alkyl group optionally substituted by 1 to 3 halogen atoms;
9) compound (I) wherein $R^1$ and $R^2$ are bonded to form piperidine, piperazine or pyrrolidine each optionally having 1 to 3 substituents selected from
(1) a halogen atom;
(2) a hydroxy group;
(3) an oxo group;
(4) a $C_{1-6}$ alkyl group optionally substituted by 1 to 3 substituents selected from halogen atom, carboxy group, hydroxy group, $C_{1-6}$ alkoxy-carbonyl group, and carbamoyl group optionally mono- or di-substituted by $C_{1-6}$ alkyl group;
(5) an amino group optionally substituted by 1 or 2 substituents selected from $C_{1-6}$ alkyl group, $C_{1-6}$ alkyl-carbonyl group, $C_{1-6}$ alkoxy-carbonyl group, $C_{6-14}$ aryl-carbonyl group, $C_{7-13}$ aralkyl-carbonyl group, $C_{1-6}$ alkylsulfonyl group, $C_{6-14}$ arylsulfonyl group and $C_{7-13}$ aralkylsulfonyl group;
(6) a $C_{1-6}$ alkyl-carbonyl group optionally substituted by 1 to 3 substituents selected from halogen atom, and amino group optionally mono- or di-substituted by $C_{1-6}$ alkyl group; and
(7) a $C_{1-6}$ alkoxy-carbonyl group optionally substituted by 1 to 3 halogen atoms;
10) compound (I) which is
N-(4-{2-[6-(4-chlorophenyl)-4-oxothieno[3,2-d]pyrimidin-3(4H)-yl]ethyl}benzyl)-N-methylacetamide;
N-(4-{2-[6-(4-chlorophenyl)-4-oxothieno[3,2-d]pyrimidin-3(4H)-yl]ethyl}benzyl)-N,N',N'-trimethylthiourea;
6-(4-chlorophenyl)-3-[2-(4-{[(3S)-3-fluoropyrrolidin-1-yl]methyl}phenyl)ethyl]thieno[3,2-d]pyrimidin-4(3H)-one;
N'-[4-[2-[6-(4-chlorophenyl)-4-oxothieno[3,2-d]pyrimidin-3(4H)-yl]ethyl]phenyl]-N,N'-dimethylacetohydrazide; or
$N^2$-(4-{2-[6-(4-chlorophenyl)-4-oxothieno[3,2-d]pyrimidin-3(4H)-yl]ethyl}benzyl)-$N^2$-methylglycinamide,
or a salt thereof;
11) a prodrug of compound (I);
12) a pharmaceutical agent which comprises compound (I) or a prodrug thereof;
13) the pharmaceutical agent of the aforementioned 12), which is a melanin-concentrating hormone receptor antagonist;
14) the pharmaceutical agent of the aforementioned 12), which is an agent for the prophylaxis or treatment of a disease caused by a melanin-concentrating hormone;
15) the pharmaceutical agent of the aforementioned 12), which is an agent for the prophylaxis or treatment of obesity;
16) the pharmaceutical agent of the aforementioned 12), which is a feeding deterrent;
17) use of compound (I) or a prodrug thereof for the production of a melanin-concentrating hormone receptor antagonist;
18) a method for antagonizing a melanin-concentrating hormone receptor in a mammal, which comprises administering an effective amount of compound (I) or a prodrug thereof to said mammal;
19) use of compound (I) or a prodrug thereof for the production of an agent for the prophylaxis or treatment of a disease caused by a melanin-concentrating hormone;
20) a method for preventing or treating a disease caused by a melanin-concentrating hormone in a mammal, which comprises administering an effective amount of compound (I) or a prodrug thereof to said mammal;
21) use of compound (I) or a prodrug thereof for the production of an agent for the prophylaxis or treatment of obesity;
22) a method for preventing or treating obesity in a mammal, which comprises administering an effective amount of compound (I) or a prodrug thereof to said mammal;
23) use of compound (I) or a prodrug thereof for the production of a feeding deterrent;
24) a method for suppressing food intake by a mammal, which comprises administering an effective amount of compound (I) or a prodrug thereof to said mammal;
and the like.

The compound of the present invention has a superior MCH receptor antagonistic action, is useful as an agent for the prophylaxis or treatment of obesity and the like, and is of lower toxicity.

BEST MODE FOR EMBODYING THE INVENTION

The "halogen atom" in the present specification means, unless otherwise specified, fluorine atom, chlorine atom, is bromine atom or iodine atom.

The "$C_{1-3}$ alkylenedioxy group" in the present specification means, unless otherwise specified, methylenedioxy, ethylenedioxy and the like.

The "$C_{1-6}$ alkyl group" in the present specification means, unless otherwise specified, methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl and the like.

The "$C_{1-6}$ alkoxy group" in the present specification means, unless otherwise specified, methoxy, ethoxy, propoxy, isopropoxy, butoxy, isobutoxy, sec-butoxy, tert-butoxy and the like.

The "$C_{1-6}$ alkylthio group" in the present specification means, unless otherwise specified, methylthio, ethylthio, propylthio, isopropylthio, butylthio, isobutylthio, sec-butylthio, tert-butylthio and the like.

The "$C_{1-6}$ alkoxy-carbonyl group" in the present specification means, unless otherwise specified, methoxycarbonyl, ethoxycarbonyl, propoxycarbonyl, tert-butoxycarbonyl and the like.

The "$C_{1-6}$ alkyl-carbonyl group" in the present specification means, unless otherwise specified, acetyl, propanoyl, butanoyl, isobutanoyl, pentaoyl, isopentanoyl, hexanoyl, 3,3-dimethylbutanoyl and the like.

The "$C_{1-6}$ alkylsulfonyl group" in the present specification means, unless otherwise specified, methylsulfonyl, ethylsulfonyl, isopropylsulfonyl and the like.

The definition of each substituent of compound (I) is explained in detail in the following.

As the "ring" of the "optionally substituted ring" for Ar, for example, "aromatic hydrocarbon", "non-aromatic cyclic hydrocarbon", "aromatic heterocycle", "non-aromatic heterocycle" and the like can be mentioned.

As the aforementioned "aromatic hydrocarbon", for example, $C_{6-14}$ aromatic hydrocarbon can be mentioned. As the $C_{6-14}$ aromatic hydrocarbon, for example, benzene, naphthalene, anthracene, phenanthrene, acenaphthylene and the like can be mentioned.

As the aforementioned "non-aromatic cyclic hydrocarbon", for example, $C_{3-10}$ cycloalkane, $C_{3-10}$ cycloalkene, $C_{4-10}$ cycloalkadiene and the like, each of which is optionally condensed with a benzene ring, can be mentioned.

As the $C_{3-10}$ cycloalkane, for example, cyclopropane, cyclobutane, cyclopentane, cyclohexane, cycloheptane, cyclooctane and the like can be mentioned.

As the $C_{3-10}$ cycloalkene, for example, cyclopentene, cyclohexene and the like can be mentioned.

As the $C_{4-10}$ cycloalkadiene, for example, cyclopentadiene, cyclohexadiene and the like can be mentioned.

The above-mentioned $C_{3-10}$ cycloalkane, $C_{3-10}$ cycloalkene and $C_{4-10}$ cycloalkadiene are each optionally condensed with a benzene ring. As the fused ring, for example, indane (dihydroindene), dihydronaphthalene, tetrahydronaphthalene, fluorene and the like can be mentioned.

As the aforementioned "aromatic heterocycle", for example, a 5- to 10-membered monocyclic or bicyclic aromatic heterocycle containing, as a ring-constituting atom besides carbon atom, 1 to 4 hetero atoms selected from an oxygen atom, a sulfur atom and a nitrogen atom can be mentioned.

As preferable examples of the "aromatic heterocycle", a 5- to 7-membered monocyclic aromatic heterocycle such as furan, thiophene, pyridine, pyrimidine, pyridazine, pyrazine, pyrrole, imidazole, pyrazole, thiazole, isothiazole, oxazole, isoxazole, oxadiazole, thiadiazole, triazole, tetrazole, triazine and the like;

a 8- to 10-membered bicyclic aromatic heterocycle such as quinoline, isoquinoline, quinazoline, quinoxaline, benzofuran, benzothiophene, benzoxazole, benzisoxazole, benzothiazole, benzimidazole, benzotriazole, indole, indazole, pyrrolopyrazine, imidazopyridine, imidazopyrazine, pyrazolopyridine, pyrazolothiophene, pyrazolotriazine and the like; and the like can be mentioned.

As the aforementioned "non-aromatic heterocycle", for example, a 5- to 12-membered monocyclic or bicyclic non-aromatic heterocycle containing, as a ring-constituting atom besides carbon atom, 1 to 4 hetero atoms selected from an oxygen atom, a sulfur atom and a nitrogen atom can be mentioned.

As preferable examples of the non-aromatic heterocycle, a 5- to 7-membered monocyclic non-aromatic heterocycle such as pyrrolidine, piperidine, morpholine, thiomorpholine, piperazine, hexamethyleneimine, oxazolidine, thiazolidine, imidazolidine, oxazoline, thiazoline, imidazoline, dioxole, dioxolane, dihydrooxadiazole, pyran, tetrahydropyran, thiopyran, tetrahydrothiopyran, pyrazolidine, tetrahydropyrimidine and the like;

a 8- to 12-membered bicyclic non-aromatic heterocycle such as dihydroindole, dihydroisoindole, dihydrobenzodioxane, dihydrobenzodioxepine, dihydrobenzofuran, tetrahydrobenzofuran, chromene, dihydroquinoline, tetrahydroquinoline, dihydroisoquinoline, tetrahydroisoquinoline, dihydrophthalazine, benzazepane and the like; and the like can be mentioned.

The "ring" of the "optionally substituted ring" for Ar is preferably benzene, indane (dihydroindene) or the like.

The "ring" of the "optionally substituted ring" for Ar optionally has 1 to 3 substituents at substitutable position(s). As such substituent, for example, (1) halogen atom;
(2) cyano group;
(3) azido group;
(4) amidino group;
(5) nitro group;
(6) nitroso group;
(7) oxo group;
(8) $C_{1-3}$ alkylenedioxy group;
(9) $C_{1-6}$ alkyl group optionally substituted by 1 to 3 substituents selected from halogen atom, carboxy group, hydroxy group, $C_{1-6}$ alkoxy-carbonyl group, and carbamoyl group optionally mono- or di-substituted by $C_{1-6}$ alkyl group;
(10) $C_{2-6}$ alkenyl group (e.g., ethenyl, 1-propenyl) optionally substituted by 1 to 3 substituents selected from halogen atom, carboxy group, hydroxy group, $C_{1-6}$ alkoxy-carbonyl group and carbamoyl group;
(11) $C_{7-13}$ aralkyl group (e.g., benzyl) optionally substituted by 1 to 3 substituents selected from $C_{1-6}$ alkyl group optionally substituted by 1 to 3 halogen atoms, hydroxy group, $C_{1-6}$ alkoxy group and halogen atom;
(12) $C_{3-10}$ cycloalkyl group (e.g., cyclopropyl, cyclohexyl);
(13) $C_{6-14}$ aryl group (e.g., phenyl, naphthyl) optionally substituted by 1 to 3 substituents selected from $C_{1-6}$ alkyl group optionally substituted by 1 to 3 halogen atoms, hydroxy group, $C_{1-6}$ alkoxy group and halogen atom;
(14) aromatic heterocyclic group (e.g., thienyl, furyl, pyridyl, oxazolyl, thiazolyl, tetrazolyl, oxadiazolyl, pyrazinyl, quinolyl, indolyl) optionally substituted by 1 to 3 substituents selected from $C_{1-6}$ alkyl group optionally substituted by 1 to 3 halogen atoms, hydroxy group, $C_{1-6}$ alkoxy group and halogen atom;
(15) non-aromatic heterocyclic group (e.g., tetrahydrofuryl, morpholinyl, thiomorpholinyl, piperidinyl, pyrrolidinyl, piperazinyl, dioxolyl, dioxolanyl, 1,3-dihydro-2-benzofuranyl, thiazolidinyl) optionally substituted by 1 to 3 substituents selected from $C_{1-6}$ alkyl group optionally substituted by 1 to 3 halogen atoms, hydroxy group, $C_{1-6}$ alkoxy group, oxo group and halogen atom;
(16) amino group optionally substituted by 1 or 2 substituents selected from $C_{1-6}$ alkyl group, $C_{1-6}$ alkyl-carbonyl group, $C_{1-6}$ alkoxy-carbonyl group, $C_{6-14}$ aryl-carbonyl group (e.g., benzoyl), $C_{7-13}$ aralkyl-carbonyl group (e.g., benzylcarbonyl, phenethylcarbonyl), $C_{1-6}$ alkylsulfonyl group, $C_{6-14}$ arylsulfonyl group (e.g., benzenesulfonyl, toluenesulfonyl, 1-naphthalenesulfonyl, 2-naphthalenesulfonyl) and $C_{7-13}$ aralkylsulfonyl group (e.g., benzylsulfonyl);
(17) $C_{1-6}$ alkyl-carbonyl group optionally substituted by 1 to 3 substituents selected from halogen atom, and amino group optionally mono- or di-substituted by $C_{1-6}$ alkyl group;
(18) $C_{3-10}$ cycloalkyl-carbonyl group (e.g., cyclopropylcarbonyl, cyclohexylcarbonyl);
(19) carboxy group;
(20) $C_{1-6}$ alkoxy-carbonyl group optionally substituted by 1 to 3 halogen atoms;
(21) sulfo group;
(22) $C_{1-6}$ alkylsulfonyl group optionally substituted by 1 to 3 halogen atoms;
(23) carbamoyl group optionally substituted by 1 or 2 substituents selected from $C_{1-6}$ alkyl group optionally substituted by 1 to 3 halogen atoms, $C_{6-14}$ aryl group (e.g., phenyl) and $C_{7-13}$ aralkyl group (e.g., benzyl);
(24) thiocarbamoyl group optionally mono- or di-substituted by $C_{1-6}$ alkyl group optionally substituted by 1 to 3 halogen atoms;

(25) sulfamoyl group optionally mono- or di-substituted by $C_{1-6}$ alkyl group optionally substituted by 1 to 3 halogen atoms;
(26) hydroxy group;
(27) $C_{1-6}$ alkoxy group optionally substituted by 1 to 3 substituents selected from halogen atom, carboxy group, $C_{1-6}$ alkoxy group and $C_{1-6}$ alkoxy-carbonyl group;
(28) $C_{2-6}$ alkenyloxy group (e.g., ethenyloxy) optionally substituted by 1 to 3 halogen atoms;
(29) $C_{3-10}$ cycloalkyloxy group (e.g., cyclohexyloxy);
(30) $C_{3-10}$ cycloalkyl-$C_{1-6}$ alkoxy group (e.g., cyclopropylmethoxy, cyclopropylethoxy);
(31) $C_{7-13}$ aralkyloxy group (e.g., benzyloxy) optionally is substituted by 1 to 3 halogen atoms;
(32) $C_{6-14}$ aryloxy group (e.g., phenyloxy, naphthyloxy);
(33) $C_{1-6}$ alkyl-carbonyloxy group (e.g., acetyloxy, tert-butylcarbonyloxy);
(34) thiol group;
(35) $C_{1-6}$ alkylthio group optionally substituted by 1 to 3 halogen atoms;
(36) $C_{7-20}$ aralkylthio group (e.g., benzylthio, tritylthio);
(37) $C_{6-14}$ arylthio group (e.g., phenylthio, naphthylthio);
(38) $C_{1-6}$ alkylsulfinyl group (e.g., methylsulfinyl); and the like can be mentioned.

As the "spacer having a main chain of 1 to 4 atoms" for A, for example, a divalent group with main chain of 1 to 4 atoms which consists of 1 to 3 selected from —O—, —S—, —SO—, —SO$_2$—, —NR$^6$— (R$^6$ is a hydrogen atom or a substituent) and optionally substituted $C_{1-6}$ alkylene group can be mentioned. Here, the "number of atoms of the main chain" is counted so that the number of atoms of the main chain will be minimum.

Here, as the substituent for R$^6$, those recited as examples of the substituent of the "optionally substituted ring" for Ar can be mentioned.

As the "$C_{1-6}$ alkylene group" of the aforementioned "optionally substituted $C_{1-6}$ alkylene group", for example, —CH$_2$—, —(CH$_2$)$_2$—, —(CH$_2$)$_3$—, —(CH$_2$)$_4$—, —CH(CH$_3$)—, —CH(C$_2$H$_5$)—, —CH(CH(CH$_3$)$_2$)—, —C(CH$_3$)$_2$, —CH$_2$—CH(CH$_3$)—, —CH(CH$_3$)—CH$_2$—, —(CH(CH$_3$))$_2$—, —(CH$_2$)$_2$C(CH$_3$)$_2$—, —(CH$_2$)$_3$C(CH$_3$)$_2$— and the like can be mentioned.

The "$C_{1-6}$ alkylene group" optionally has 1 to 3 substituents at substitutable position(s). As such substituent, for example, those recited as examples of the substituent of the "optionally substituted ring" for Ar can be mentioned. Of those, oxo group, hydroxy group and the like are preferably, and oxo group is particularly preferable.

As specific examples of the "spacer having a main chain of 1 to 4 atoms" for A,
(1) a $C_{1-4}$ alkylene group (preferably —(CH$_2$)$_2$—, —CH$_2$—CH(CH$_3$)—, —CH(CH$_3$)—CH$_2$— and the like) optionally substituted by 1 or 2 substituents selected from an oxo group and a hydroxy group;
(2) —CO—NR$^6$— or —NR$^6$—CO— (R$^6$ is as defined above) and the like can be mentioned.

The "spacer having a main chain of 1 to 4 atoms" for A is preferably a $C_{1-4}$ alkylene group (preferably —(CH$_2$)$_2$—, —CH$_2$—CH(CH$_3$)—, —CH(CH$_3$)—CH$_2$— and the like) optionally substituted by 1 or 2 substituents selected from an oxo group and a hydroxy group, —NHCO—, —CONH— and the like, more preferably a $C_{1-4}$ alkylene group (preferably —(CH$_2$)$_2$—, —CH$_2$—CH(CH$_3$)—, —CH(CH$_3$)—CH$_2$— and the like) optionally substituted by 1 or 2 substituents selected from an oxo group and a hydroxy group, and still more preferably a $C_{1-4}$ alkylene group (preferably —(CH$_2$)$_2$—, —CH$_2$—CH(CH$_3$)—, —CH(CH$_3$)—CH$_2$— and the like) optionally substituted by oxo group.

As the "$C_{1-10}$ alkylene group" for B, for example, —CH$_2$—, —(CH$_2$)$_2$—, —(CH$_2$)$_3$—, —(CH$_2$)$_4$—, —(CH$_2$)$_5$—, —(CH$_2$)$_6$—, —(CH$_2$)$_7$—, —(CH$_2$)$_8$—, —(CH$_2$)$_9$—, —(CH$_2$)$_{10}$—, —CH(CH$_3$)—, —CH(C$_2$H$_5$)—, —CH(CH(CH$_3$)$_2$)—, —C(CH$_3$)$_2$—, —CH$_2$—CH(CH$_3$)—, —CH(CH$_3$)—CH$_2$—, —(CH(CH$_3$))$_2$—, —(CH$_2$)$_2$C(CH$_3$)$_2$—, —(CH$_2$)$_3$C(CH$_3$)$_2$— and the like can be mentioned.

B is preferably a bond or a $C_{1-10}$ alkylene group, more preferably a bond, —CH$_2$—, —(CH$_2$)$_2$—, —CH(CH$_3$)— and the like.

As the substituent for R$^3$ or R$^5$, those recited as examples of the substituent of the "optionally substituted ring" for Ar can be mentioned.

R$^3$ is preferably a hydrogen atom or a hydroxy group, more preferably a hydrogen atom.

R$^5$ is preferably a hydrogen atom.

As the "cyclic group" of the "optionally substituted cyclic group" for R$^4$, for example, "aromatic hydrocarbon group", "non-aromatic cyclic hydrocarbon group", "aromatic heterocyclic group", "non-aromatic heterocyclic group" and the like can be mentioned.

As the aforementioned "aromatic hydrocarbon group", for example, $C_{6-14}$ aromatic hydrocarbon group can be mentioned. As the $C_{6-14}$ aromatic hydrocarbon group, for example, phenyl, naphthyl, anthracenyl, pheranthrenyl, acenaphthylenyl and the like can be mentioned.

As the aforementioned "non-aromatic cyclic hydrocarbon group", for example, $C_{3-10}$ cycloalkyl group, $C_{3-10}$ cycloalkenyl group, $C_{4-10}$ cycloalkadienyl group and the like, each of which is optionally condensed with a benzene ring, can be mentioned.

As the $C_{3-10}$ cycloalkyl group, for example, cyclopropyl, cyclobutyl, cyclopentyl, cyclohexyl, cycloheptyl, cyclooctyl and the like can be mentioned.

As the $C_{3-10}$ cycloalkenyl group, for example, 2-cyclopenten-1-yl, 3-cyclopenten-1-yl, 2-cyclohexen-1-yl, 3-cyclohexen-1-yl and the like can be mentioned.

As the $C_{4-10}$ cycloalkadienyl group, for example, 2,4-cyclopentadien-1-yl, 2,4-cyclohexadien-1-yl, 2,5-cyclohexadien-1-yl and the like can be mentioned.

The above-mentioned $C_{3-10}$ cycloalkyl group, $C_{3-10}$ cycloalkenyl group and $C_{4-10}$ cycloalkadienyl group are each optionally condensed with a benzene ring. As the fused ring group, for example, indanyl, dihydronaphthyl, tetrahydronaphthyl, fluorenyl and the like can be mentioned.

As the aforementioned "aromatic heterocyclic group", for example, a 5- to 10-membered monocyclic or bicyclic aromatic heterocyclic group containing, as a ring-constituting atom besides carbon atom, 1 to 4 hetero atoms selected from an oxygen atom, a sulfur atom and a nitrogen atom can be mentioned.

As preferable examples of the "aromatic heterocyclic group",
a 5- to 7-membered monocyclic aromatic heterocyclic group such as furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl,), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 4-isothiazolyl), oxazolyl (e.g., 2-oxazolyl, 4-oxazolyl, 5-oxazolyl), isoxazolyl, oxadiazolyl (e.g., 1,2,4-oxadiazol-3-yl, 1,2,4-oxadiazol-5-yl, 1,3,4-oxadiazol-2-yl), thiadiazolyl (e.g., 1,3,4-thiadiazol-2-yl, 1,2,4-thiadiazol-3-yl, 1,2,4-thiadiazol-5-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,2,4-triazin-1-yl, 1,2,4-triazin-3-yl, 1,2,4-triazin-5-yl, 1,2,4-triazin-6-yl) and the like;

a 8- to 10-membered bicyclic aromatic heterocyclic group such as quinolyl (e.g., 2-quinolyl, 3-quinolyl, 4-quinolyl, 6-quinolyl), isoquinolyl (e.g., 3-isoquinolyl), quinazolyl (e.g., 2-quinazolyl, 4-quinazolyl), quinoxalyl (e.g., 2-quinoxalyl, 6-quinoxalyl), benzofuryl (e.g., 2-benzofuryl, 3-benzofuryl), benzothienyl (e.g., 2-benzothienyl, 3-benzothienyl), benzoxazolyl (e.g., 2-benzoxazolyl), benzisoxazolyl (e.g., 7-benzisoxazolyl), benzothiazolyl (e.g., 2-benzothiazolyl), benzimidazolyl (e.g., benzimidazol-1-yl, benzimidazol-2-yl, benzimidazol-5-yl), benzotriazolyl (e.g., 1H-1,2,3-benzotriazol-5-yl), indolyl (e.g., indol-1-yl, indol-2-yl, indol-3-yl, indol-5-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridinyl (e.g., 1H-imidazo[4,5-b]pyridin-2-yl, 1H-imidazo[4,5-c]pyridin-2-yl, 2H-imidazo[1,2-a]pyridin-3-yl), imidazopyrazinyl (e.g., 1H-imidazo[4,5-b]pyrazin-2-yl), pyrazolopyridinyl (e.g., 1H-pyrazolo[4,3-c]pyridin-3-yl), pyrazolothienyl (e.g., 2H-pyrazolo[3,4-b]thiophen-2-yl), pyrazolotriazinyl (e.g., pyrazolo[5,1-c][1,2,4]triazin-3-yl) and the like; and the like can be mentioned.

As the aforementioned "non-aromatic heterocyclic group", for example, a 5- to 12-membered monocyclic or bicyclic non-aromatic heterocyclic group containing, as a ring-constituting atom besides carbon atom, 1 to 4 hetero atoms selected from an oxygen atom, a sulfur atom and a nitrogen atom can be mentioned.

As preferable examples of the "non-aromatic heterocyclic group",
a 5- to 7-membered monocyclic non-aromatic heterocyclic group such as pyrrolidinyl (e.g., 1-pyrrolidinyl), piperidinyl (e.g., piperidino, 2-piperidinyl, 3-piperidinyl, 4-piperidinyl), morpholinyl (e.g., morpholino), thiomorpholinyl (e.g., thiomorpholino), piperazinyl (e.g., 1-piperazinyl, 2-piperazinyl, 3-piperazinyl), hexamethyleneiminyl (e.g., hexamethyleneimin-1-yl), oxazolidinyl (e.g., oxazolidin-2-yl), thiazolidinyl (e.g., thiazolidin-2-yl), imidazolidinyl (e.g., imidazolidin-2-yl, imidazolidin-3-yl), oxazolinyl (e.g., oxazolin-2-yl), thiazolinyl (e.g., thiazolin-2-yl), imidazolinyl (e.g., imidazolin-2-yl, imidazolin-3-yl), dioxolyl (e.g., 1,3-dioxol-4-yl), dioxolanyl (e.g., 1,3-dioxolan-4-yl), dihydrooxadiazolyl (e.g., 4,5-dihydro-1,2,4-oxadiazol-3-yl), pyranyl (e.g., 4-pyranyl), tetrahydropyranyl (e.g., 4-tetrahydropyranyl), thiopyranyl (e.g., 4-thiopyranyl), tetrahydrothiopyranyl (e.g., 4-tetrahydrothiopyranyl), pyrazolidinyl (e.g., pyrazolidin-1-yl), tetrahydropyrimidinyl and the like;
a 8- to 12-membered bicyclic non-aromatic heterocyclic group such as dihydroindolyl (e.g., 2,3-dihydro-1H-indol-1-yl), dihydroisoindolyl (e.g., 1,3-dihydro-2H-isoindol-2-yl), dihydrobenzodioxinyl (e.g., 2,3-dihydro-1,4-benzodioxinyl), dihydrobenzodioxepinyl (e.g., 3,4-dihydro-2H-1,5-benzodioxepinyl), dihydrobenzofuranyl (e.g., 2,3-dihydro-1-benzofuran-5-yl), tetrahydrobenzofuranyl (e.g., 4,5,6,7-tetrahydro-1-benzofuran-3-yl), chromenyl (e.g., 4H-chromen-2-yl, 2H-chromen-3-yl), dihydroquinolinyl (e.g., 1,2-dihydroquinolin-4-yl), tetrahydroquinolinyl (e.g., 1,2,3,4-tetrahydroquinolin-4-yl), dihydroisoquinolinyl (e.g., 1,2-dihydroisoquinolin-4-yl), tetrahydroisoquinolinyl (e.g., 1,2,3,4-tetrahydroisoquinolin-4-yl), dihydrophthalazinyl (e.g., 1,4-dihydrophthalazin-4-yl), benzazepanyl and the like; and the like can be mentioned.

The "cyclic group" of the "optionally substituted cyclic group" for $R^4$ is preferably a phenyl group.

The "cyclic group" of the "optionally substituted cyclic group" for $R^4$ is optionally has 1 to 3 substituents at substitutable position(s). As such substituent, for example, those recited as examples of the substituent of the "optionally substituted ring" for Ar can be mentioned.

The "optionally substituted cyclic group" for $R^4$ is preferably a phenyl group optionally substituted by 1 to 3 substituents selected from halogen atom, hydroxy group and the like, more preferably a phenyl group substituted by halogen atom.

As the "$C_{1-10}$ alkyl group" of the "optionally substituted $C_{1-10}$ alkyl group" for $R^4$, for example, methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl and the like) can be mentioned.

The "$C_{1-10}$ alkyl group" optionally has 1 to 3 substituents at substitutable position(s). As such substituent, for example,
(1) halogen atom;
(2) cyano group;
(3) azido group;
(4) amidino group;
(5) nitro group;
(6) nitroso group;
(7) $C_{1-3}$ alkylenedioxy group;
(8) $C_{3-10}$ cycloalkyl group (e.g., cyclopropyl, cyclohexyl);
(9) $C_{6-14}$ aryl group (e.g., phenyl, naphthyl) optionally substituted by 1 to 3 substituents selected from $C_{1-6}$ alkyl group optionally substituted by 1 to 3 halogen atoms, hydroxy group, $C_{1-6}$ alkoxy group and halogen atom;
(10) aromatic heterocyclic group (e.g., thienyl, furyl, pyridyl, oxazolyl, thiazolyl, tetrazolyl, oxadiazolyl, pyrazinyl, quinolyl, indolyl) optionally substituted by 1 to 3 substituents selected from $C_{1-6}$ alkyl group optionally substituted by 1 to 3 halogen atoms, hydroxy group, $C_{1-6}$ alkoxy group and halogen atom;
(11) non-aromatic heterocyclic group (e.g., tetrahydrofuryl, morpholinyl, thiomorpholinyl, piperidinyl, pyrrolidinyl, piperazinyl, dioxolyl, dioxolanyl, 1,3-dihydro-2-benzofuranyl, thiazolidinyl) optionally substituted by 1 to 3 substituents selected from $C_{1-6}$ alkyl group optionally substituted by 1 to 3 halogen atoms, hydroxy group, $C_{1-6}$ alkoxy group, oxo group and halogen atom;
(12) amino group optionally substituted by 1 or 2 substituents selected from $C_{1-6}$ alkyl group, $C_{1-6}$ alkyl-carbonyl group, $C_{1-6}$ alkoxy-carbonyl group, $C_{6-14}$ aryl-carbonyl group (e.g., benzoyl), $C_{7-13}$ aralkyl-carbonyl group (e.g., benzylcarbonyl, phenethylcarbonyl), $C_{1-6}$ alkylsulfonyl group, $C_{6-14}$ arylsulfonyl group (e.g., benzenesulfonyl, toluenesulfonyl, naphthalenesulfonyl, 2-naphthalenesulfonyl) and $C_{7-13}$ aralkylsulfonyl group (e.g., benzylsulfonyl);
(13) $C_{1-6}$ alkyl-carbonyl group optionally substituted by 1 to 3 halogen atoms;
(14) $C_{3-10}$ cycloalkyl-carbonyl group (e.g., cyclopropylcarbonyl, cyclohexylcarbonyl);
(15) carboxy group;
(16) $C_{1-6}$ alkoxy-carbonyl group optionally substituted by 1 to 3 halogen atoms;
(17) sulfo group;
(18) $C_{1-6}$ alkylsulfonyl group optionally substituted by 1 to 3 halogen atoms;
(19) carbamoyl group optionally substituted by 1 or 2 substituents selected from $C_{1-6}$ alkyl group optionally substituted by 1 to 3 halogen atoms, $C_{6-14}$ aryl group (e.g., phenyl) and $C_{7-13}$ aralkyl group (e.g., benzyl);
(20) thiocarbamoyl group optionally mono- or di-substituted by $C_{1-6}$ alkyl group optionally substituted by 1 to 3 halogen atoms;
(21) sulfamoyl group optionally mono- or di-substituted by $C_{1-6}$ alkyl group optionally substituted by 1 to 3 halogen atoms;
(22) hydroxy group;
(23) $C_{1-6}$ alkoxy group optionally substituted by 1 to 3 substituents selected from halogen atom, carboxy group, $C_{1-6}$ alkoxy group and $C_{1-6}$ alkoxy-carbonyl group;
(24) $C_{2-6}$ alkenyloxy group (e.g., ethenyloxy) optionally substituted by 1 to 3 halogen atoms;
(25) $C_{3-10}$ cycloalkyloxy group (e.g., cyclohexyloxy);
(26) $C_{3-10}$ cycloalkyl-$C_{1-6}$ alkoxy group (e.g., cyclopropylmethoxy, cyclopropylethoxy);
(27) $C_{7-13}$ aralkyloxy group (e.g., benzyloxy) optionally substituted by 1 to 3 halogen atoms;
(28) $C_{6-14}$ aryloxy group (e.g., phenyloxy, naphthyloxy);
(29) $C_{1-6}$ alkyl-carbonyloxy group (e.g., acetyloxy, tert-butylcarbonyloxy);
(30) thiol group;
(31) $C_{1-6}$ alkylthio group optionally substituted by 1 to 3 halogen atoms;
(32) $C_{7-20}$ aralkylthio group (e.g., benzylthio, tritylthio);
(33) $C_{6-14}$ arylthio group (e.g., phenylthio, naphthylthio);
(34) $C_{1-6}$ alkylsulfinyl group (e.g., methylsulfinyl); and the like can be mentioned.

As the substituent for $R^1$ or $R^2$, those recited as examples of the substituent of the "optionally substituted ring" for Ar can be mentioned.
Of these,
(1) $C_{1-6}$ alkyl group optionally substituted by 1 to 3 substituents selected from halogen atom, carboxy group, hydroxy group, $C_{1-6}$ alkoxy-carbonyl group, and carbamoyl group optionally mono- or di-substituted by $C_{1-6}$ alkyl group;
(2) amino group optionally substituted by 1 or 2 substituents selected from $C_{1-6}$ alkyl group, $C_{1-6}$ alkyl-carbonyl group, $C_{1-6}$ alkoxy-carbonyl group, $C_{6-14}$ aryl-carbonyl group (e.g., benzoyl), $C_{7-13}$ aralkyl-carbonyl group (e.g., benzylcarbonyl, phenethylcarbonyl), $C_{1-6}$ alkylsulfonyl group, $C_{6-14}$ arylsulfonyl group (e.g., benzenesulfonyl, toluenesulfonyl, 1-naphthalenesulfonyl, 2-naphthalenesulfonyl) and $C_{7-13}$ aralkylsulfonyl group (e.g., benzylsulfonyl);
(3) $C_{1-6}$ alkyl-carbonyl group optionally substituted by 1 to 3 substituents selected from halogen atom, and an amino group optionally mono- or di-substituted by $C_{1-6}$ alkyl group;
(4) $C_{3-10}$ cycloalkyl-carbonyl group (e.g., cyclopropylcarbonyl, cyclohexylcarbonyl);
(5) $C_{1-6}$ alkoxy-carbonyl group optionally substituted by 1 to 3 halogen atoms;
(6) $C_{1-6}$ alkylsulfonyl group optionally substituted by 1 to 3 halogen atoms;
(7) carbamoyl group optionally substituted by 1 or 2 substituents selected from $C_{1-6}$ alkyl group optionally substituted by 1 to 3 halogen atoms, $C_{6-14}$ aryl group (e.g., phenyl) and $C_{7-13}$ aralkyl group (e.g., benzyl);
(8) thiocarbamoyl group optionally mono- or di-substituted by $C_{1-6}$ alkyl group optionally substituted by 1 to 3 halogen atoms; and the like are preferable.

As the "nitrogen-containing heterocycle" of the "optionally substituted nitrogen-containing heterocycle" formed by $R^1$ bonded to $R^2$ or B, together with the adjacent nitrogen atom, for example, 3- to 10-membered monocyclic nitrogen-containing non-aromatic heterocyclic group containing at least one nitrogen atom as a ring-constituting atom besides carbon atom, which optionally further contains 1 to 3 hetero atoms selected from an oxygen atom, a sulfur atom and a nitrogen atom, can be mentioned.

As specific examples of the "nitrogen-containing heterocycle", aziridine, azetidine, morpholine, thiomorpholine, piperidine, piperazine, pyrrolidine, hexamethyleneimine (azepane), heptamethyleneimine, hexahydropyrimidine, 1,4-diazepane, thiazolidine, oxazolidine, imidazolidine, tetrahydropyridine, dihydroimidazole and the like can be mentioned. Of these, piperidine, piperazine, pyrrolidine and the like are preferable.

The "nitrogen-containing heterocycle" optionally has 1 to 3 substituents at substitutable position(s). As such substituent, for example, those recited as examples of the substituent of the "optionally substituted ring" for Ar can be mentioned. Particularly,
(1) halogen atom;
(2) hydroxy group;
(3) oxo group;
(4) $C_{1-6}$ alkyl group optionally substituted by 1 to 3 substituents selected from halogen atom, carboxy group, hydroxy group, $C_{1-6}$ alkoxy-carbonyl group, and carbamoyl group optionally mono- or di-substituted by $C_{1-6}$ alkyl group;
(5) amino group optionally substituted by 1 or 2 substituents selected from $C_{1-6}$ alkyl group, $C_{1-6}$ alkyl-carbonyl group, $C_{1-6}$ alkoxy-carbonyl group, $C_{6-14}$ aryl-carbonyl group, $C_{7-13}$ aralkyl-carbonyl group, $C_{1-6}$ alkylsulfonyl group, $C_{6-14}$ arylsulfonyl group and $C_{7-13}$ aralkylsulfonyl group;
(6) $C_{1-6}$ alkyl-carbonyl group optionally substituted by 1 to 3 substituents selected from halogen atom, and an amino group optionally mono- or di-substituted by $C_{1-6}$ alkyl group;
(7) $C_{1-6}$ alkoxy-carbonyl group optionally substituted by 1 to 3 halogen atoms; and the like are preferable.

As the "nitrogen-containing fused heterocycle" of the "optionally substituted nitrogen-containing fused heterocycle" is formed by $R^1$ bonded to Ar, together with the nitrogen atom adjacent to $R^1$ and B adjacent to Ar, for example, 8- to 12-membered bicyclic nitrogen-containing non-aromatic heterocyclic group containing at least one nitrogen atom as a ring-constituting atom besides carbon atom, which optionally further contains 1 to 3 hetero atoms selected from an oxygen atom, a sulfur atom and a nitrogen atom, can be mentioned.

As specific examples of the "nitrogen-containing fused heterocycle", benzazepane, dihydroindole, dihydroisoindole, dihydroquinoline, tetrahydroquinoline, dihydroisoquinoline, tetrahydroisoquinoline and the like can be mentioned. Of these, benzazepane and the like are preferable.

The "nitrogen-containing fused heterocycle" optionally has 1 to 3 substituents at substitutable position(s). As such substituent, for example, those recited as examples of the substituent of the "optionally substituted ring" for Ar can be mentioned.

As preferable examples of compound (I), the following compounds or a salt thereof can be mentioned.
[Compound A]
A compound wherein Ar is benzene or indane (dihydroindene);
A is $C_{1-4}$ alkylene group (preferably —$(CH_2)_2$—, —$CH_2$—$CH(CH_3)$—, —$CH(CH_3)$—$CH_2$— and the like) optionally substituted by 1 or 2 substituents selected from an oxo group and a hydroxy group, —NHCO— or —CONH—;
B is a bond or a $C_{1-10}$ alkylene group (preferably —$CH_2$—, —$(CH_2)_2$—, —$CH(CH_3)$— and the like);

$R^3$ and $R^5$ are hydrogen atoms;

$R^4$ is a phenyl group optionally substituted by 1 to 3 substituents selected from halogen atom, hydroxy group and the like; and $R^1$ and $R^2$ are each independently (1) hydrogen atom;

(2) $C_{1-6}$ alkyl group optionally substituted by 1 to 3 substituents selected from halogen atom, carboxy group, hydroxy group, $C_{1-6}$ alkoxy-carbonyl group and carbamoyl group;

(3) amino group optionally substituted by 1 or 2 substituents selected from $C_{1-6}$ alkyl group, $C_{1-6}$ alkyl-carbonyl group, $C_{1-6}$ alkoxy-carbonyl group, $C_{6-14}$ aryl-carbonyl group (e.g., benzoyl), $C_{7-13}$ aralkyl-carbonyl group (e.g., benzylcarbonyl, phenethylcarbonyl), $C_{1-6}$ alkylsulfonyl group, $C_{6-14}$ arylsulfonyl group (e.g., benzenesulfonyl, toluenesulfonyl, 1-naphthalenesulfonyl, 2-naphthalenesulfonyl) and $C_{7-13}$ aralkylsulfonyl group (e.g., benzylsulfonyl);

(4) $C_{1-6}$ alkyl-carbonyl group optionally substituted by 1 to 3 halogen atoms;

(5) $C_{3-10}$ cycloalkyl-carbonyl group (e.g., cyclopropylcarbonyl, cyclohexylcarbonyl);

(6) $C_{1-6}$ alkoxy-carbonyl group optionally substituted by 1 to 3 halogen atoms;

(7) $C_{1-6}$ alkylsulfonyl group optionally substituted by 1 to 3 halogen atoms;

(8) carbamoyl group optionally substituted by 1 or 2 substituents selected from $C_{1-6}$ alkyl group optionally substituted by 1 to 3 halogen atoms, $C_{6-14}$ aryl group (e.g., phenyl) and $C_{7-13}$ aralkyl group (e.g., benzyl); or (9) thiocarbamoyl group optionally mono- or di-substituted by $C_{1-6}$ alkyl group optionally substituted by 1 to 3 halogen atoms; or $R^1$ and $R^2$ or $R^1$ and B are bonded to form piperidine, piperazine or pyrrolidine each optionally having 1 to 3 substituents selected from halogen atom, hydroxy group and oxo group.

[Compound B]

A compound wherein Ar is benzene or indane (dihydroindene);

A is $C_{1-4}$ alkylene group (preferably —$(CH_2)_2$—, —$CH_2$—$CH(CH_3)$—, —$CH(CH_3)$—$CH_2$— and the like) optionally substituted by 1 or 2 substituents selected from an oxo group and a hydroxy group;

B is a bond or a $C_{1-10}$ alkylene group (preferably —$CH_2$—, —$(CH_2)_2$—, —$CH(CH_3)$— and the like);

$R^3$ is a hydrogen atom or a hydroxy group;

$R^5$ is a hydrogen atom;

$R^4$ is a phenyl group optionally substituted by 1 to 3 substituents selected from halogen atom, hydroxy group and the like; and $R^1$ and $R^2$ are each independently (1) hydrogen atom;

(2) $C_{1-6}$ alkyl group optionally substituted by 1 to 3 substituents selected from halogen atom, carboxy group, hydroxy group, $C_{1-6}$ alkoxy-carbonyl group, and carbamoyl group optionally mono- or di-substituted by $C_{1-6}$ alkyl group;

(3) amino group optionally substituted by 1 or 2 substituents selected from $C_{1-6}$ alkyl group, $C_{1-6}$ alkyl-carbonyl group, $C_{1-6}$ alkoxy-carbonyl group, $C_{6-14}$ aryl-carbonyl group (e.g., benzoyl), $C_{7-13}$ aralkyl-carbonyl group (e.g., benzylcarbonyl, phenethylcarbonyl), $C_{1-6}$ alkylsulfonyl group, $C_{6-14}$ arylsulfonyl group (e.g., benzenesulfonyl, toluenesulfonyl, 1-naphthalenesulfonyl, 2-naphthalenesulfonyl) and $C_{7-13}$ aralkylsulfonyl group (e.g., benzylsulfonyl);

(4) $C_{1-6}$ alkyl-carbonyl group optionally substituted by 1 to 3 substituents selected from halogen atom, and amino group optionally mono- or di-substituted by $C_{1-6}$ alkyl group;

(5) $C_{3-10}$ cycloalkyl-carbonyl group (e.g., cyclopropylcarbonyl, cyclohexylcarbonyl);

(6) $C_{1-6}$ alkoxy-carbonyl group optionally substituted by 1 to 3 halogen atoms;

(7) $C_{1-6}$ alkylsulfonyl group optionally substituted by 1 to 3 halogen atoms;

(8) carbamoyl group optionally substituted by 1 or 2 substituents selected from $C_{1-6}$ alkyl group optionally substituted by 1 to 3 halogen atoms, $C_{6-14}$ aryl group (e.g., phenyl) and $C_{7-13}$ aralkyl group (e.g., benzyl); or (9) thiocarbamoyl group optionally mono- or di-substituted by $C_{1-6}$ alkyl group optionally substituted by 1 to 3 halogen atoms.

[Compound C]

A compound wherein Ar is benzene or indane (dihydroindene);

A is $C_{1-4}$ alkylene group (preferably —$(CH_2)_2$—, —$CH_2$—$CH(CH_3)$—, —$CH(CH_3)$—$CH_2$— and the like) optionally substituted by 1 or 2 substituents selected from an oxo group and a hydroxy group;

B is a bond or a $C_{1-10}$ alkylene group (preferably —$CH_2$—, —$(CH_2)_2$—, —$CH(CH_3)$— and the like);

$R^3$ is a hydrogen atom or a hydroxy group;

$R^5$ is a hydrogen atom;

$R^4$ is a phenyl group optionally substituted by 1 to 3 substituents selected from halogen atom, hydroxy group and the like; and $R^1$ and $R^2$ are bonded to form piperidine, piperazine or pyrrolidine each optionally having 1 to 3 substituents selected from (1) halogen atom;

(2) hydroxy group;

(3) oxo group;

(4) $C_{1-6}$ alkyl group optionally substituted by 1 to 3 substituents selected from halogen atom, carboxy group, hydroxy group, $C_{1-6}$ alkoxy-carbonyl group, and carbamoyl group optionally mono- or di-substituted by $C_{1-6}$ alkyl group;

(5) amino group optionally substituted by 1 or 2 substituents selected from $C_{1-6}$ alkyl group, $C_{1-6}$ alkyl-carbonyl group, $C_{1-6}$ alkoxy-carbonyl group, $C_{6-14}$ aryl-carbonyl group, $C_{7-13}$ aralkyl-carbonyl group, $C_{1-6}$ alkylsulfonyl group, $C_{6-14}$ arylsulfonyl group and $C_{7-13}$ aralkylsulfonyl group;

(6) $C_{1-6}$ alkyl-carbonyl group optionally substituted by 1 to 3 substituents selected from halogen atom, and amino group optionally mono- or di-substituted by $C_{1-6}$ alkyl group; and (7) $C_{1-6}$ alkoxy-carbonyl group optionally substituted by 1 to 3 halogen atoms.

[Compound D]

N-(4-{2-[6-(4-chlorophenyl)-4-oxothieno[3,2-d]pyrimidin-3(4H)-yl]ethyl}benzyl)-N-methylacetamide (Example 6);

N-(4-{2-[6-(4-chlorophenyl)-4-oxothieno[3,2-d]pyrimidin-3(4H)-yl]ethyl}benzyl)-N,N',N'-trimethylthiourea (Example 9);

6-(4-chlorophenyl)-3-[2-(4-{[(3S)-3-fluoropyrrolidin-1-yl]methyl}phenyl)ethyl]thieno[3,2-d]pyrimidin-4(3H)-one (Example 18);

N'-[4-[2-[6-(4-chlorophenyl)-4-oxothieno[3,2-d]pyrimidin-3(4H)-yl]ethyl]phenyl]-N,N'-dimethylacetohydrazide (Example 22); or $N^2$-(4-{2-[6-(4-chlorophenyl)-4-oxothieno[3,2-d]pyrimidin-3(4H)-yl]ethyl}benzyl)-$N^2$-methylglycinamide (Example 32).

When compound (I) is in the form of a salt, concrete examples thereof include salts with inorganic bases, ammonium salts, salts with organic bases, salts with inorganic acids, salts with organic acids, salts with basic or acidic amino acids and the like.

Preferable examples of the salts with inorganic bases include alkali metal salts such as sodium salt, potassium salt, and the like; alkaline earth metal salts such as calcium salts, magnesium salts, barium salts, and the like; aluminum salts, and the like.

Preferable examples of the salts with organic bases include salts with trimethylamine, triethylamine, pyridine, picoline, ethanolamine, diethanolamine, triethanolamine, dicyclohexylamine, N,N'-dibenzylethylenediamine, and the like.

Preferable examples of the salts with inorganic acids include salts with hydrochloric acid, hydrobromic acid, nitric acid, sulfuric acid, phosphoric acid, and the like.

Preferable examples of the salts with organic acids include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, and the like.

Preferable examples of the salts with basic amino acids include salts with arginine, lysine, ornithine, and the like.

Preferable examples of the salts with acidic amino acids include salts with aspartic acid, glutamic acid, and the like.

Of these, pharmaceutically acceptable salts are preferable.

Compound (I) may be an anhydrate or a hydrate. When it is a hydrate, it may contain 0.5 to 3 water molecules.

Moreover, compound (I) may be labeled with an isotope (e.g., $^3$H, $^{14}$C, $^{35}$S, etc.).

When compound (I) contains an optical isomer, a stereoisomer, a regioisomer or a rotamer, these are also encompassed in compound (I), and can be obtained as a single product according to synthesis and separation methods known per se. For example, when compound (I) has an optical isomer, an optical isomer resolved from this compound is also encompassed in compound (I).

In compound (I), when $R^3$ is a hydroxy group, tautomers represented by the following formula can be present, and such tautomers are also encompassed in compound (I).

A prodrug of compound (I) means a compound which is converted to compound (I) with a reaction due to an enzyme, an gastric acid, etc. under the physiological condition in the living body, that is, a compound which is converted to compound (I) with oxidation, reduction, hydrolysis, etc. according to an enzyme; a compound which is converted to compound (I) by hydrolysis etc. due to gastric acid, etc. A prodrug for compound (I) may be a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation and tert-butylation, etc.); a compound obtained by subjecting a hydroxy group in compound (I) to an acylation, alkylation, phosphorylation or boration (e.g., a compound obtained by subjecting a hydroxy group in compound (I) to an acetylation, palmitoylation, propanoylation, pivaloylation, succinylation, fumarylation, alanylation, dimethylaminomethylcarbonylation, etc.); a compound obtained by subjecting a carboxyl group in compound (I) to an esterification or amidation (e.g., a compound obtained by subjecting a carboxyl group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification and methylamidation, etc.) and the like. Any of these compounds can be produced from compound (I) by a method known per se.

A prodrug of compound (I) may also be one which is converted into compound (I) under a physiological condition, such as those described in IYAKUHIN no KAIHATSU (Development of Pharmaceuticals), Vol. 7, Design of Molecules, p. 163-198, published by HIROKAWA SHOTEN (1990).

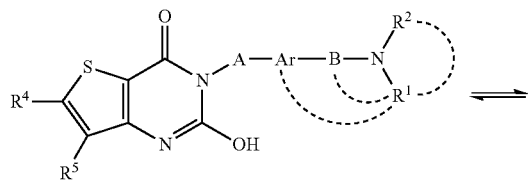 ⇌ 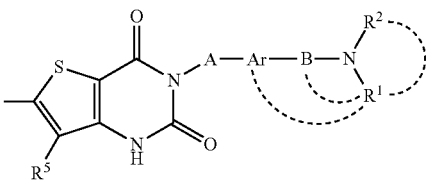

Compound (I) may be a crystal.

The crystal of compound (I) (hereinafter sometimes to be abbreviated as the crystal of the present invention) can be produced by crystallizing compound (I) by a crystallization method known per se.

In the present specification, the melting point means that measured using, for example, a micromelting point apparatus (Yanako, MP-500D or Buchi, B-545) or a DSC (differential scanning calorimetry) device (SEIKO, EXSTAR6000) and the like.

In general, the melting points may vary depending on the measurement apparatuses, the measurement conditions and the like. The crystal in the present specification may show is different values from the melting point described in the present specification, as long as they are within each of a general error range.

The crystal of the present invention is superior in physicochemical properties (e.g., melting point, solubility, stability) and biological properties (e.g., pharmacokinetics (absorption, distribution, metabolism, excretion), efficacy expression), and thus it is extremely useful as a medicament.

For example, compound (I) can be produced according to [Production Method 1] to [Production Method 3], which are described in detail below, or an analogous method thereto.

In the following [Production Method 1] to [Production Method 3], the compounds for the starting material compound may be used in the form of a salt, respectively. As such salt, those exemplified as the salt of the aforementioned compound (I) can be used.

In the following production methods, when alkylation reaction, hydrolysis reaction, amination reaction, esterification reaction, amidation reaction, etherification reaction, oxidation reaction, reduction reaction etc. are to be conducted, these reactions are carried out according to methods known per se, for example, those described in Organic Functional Group Preparations, 2nd Ed., Academic Press Inc., 1989; Comprehensive Organic Transformations, VCH Publishers Inc., 1989; and the like.

[Production Method 1]

Of compounds (I), compound (Ia) wherein $R^3$ is a hydrogen atom can be produced, for example, by reacting compound (II) with compound (III).

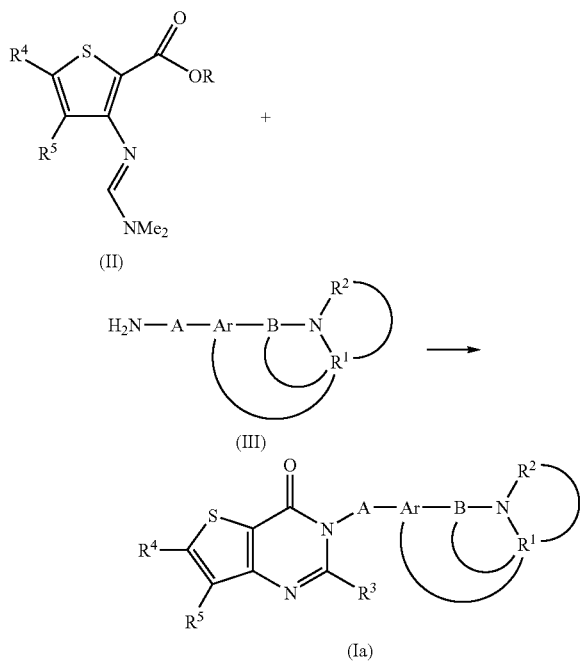

(II)

(III)

(Ia)

wherein R is $C_{1-6}$ alkyl group, and other symbols are as defined above.

This reaction is generally performed in an inert solvent.

As the "inert solvent", for example, alcohol solvents, ether solvents, halogenated hydrocarbon solvents, aromatic solvents, nitrile solvents, amide solvents, sulfoxide solvents and the like can be mentioned. These may be used in a mixture of two or more kinds thereof at an appropriate ratio. Of these, ethanol, tetrahydrofuran (THF), N,N-dimethylformamide (DMF), dimethyl sulfoxide and the like are preferable.

This reaction may be performed in the copresence of a base as necessary.

As the "base", for example;
1) strong bases such as alkali metal or alkaline earth metal hydrides (e.g., lithium hydride, sodium hydride, potassium hydride, calcium hydride), alkali metal or alkaline earth metal amides (e.g., lithium amide, sodium amide, lithium diisopropylamide, lithium dicyclohexylamide, lithium hexamethyldisilazide, sodium hexamethyldisilazide, potassium hexamethyldisilazide), alkali metal or alkaline earth metal $C_{1-6}$ alkoxides (e.g., sodium methoxide, sodium ethoxide, potassium tert-butoxide), and the like;
2) inorganic bases such as alkali metal or alkaline earth metal hydroxides (e.g., sodium hydroxide, potassium hydroxide, lithium hydroxide, barium hydroxide), alkali metal or alkaline earth metal carbonates (e.g., sodium carbonate, potassium carbonate, cesium carbonate), alkali metal hydrogen carbonates (e.g., sodium hydrogen carbonate, potassium hydrogen carbonate) and the like;
3) organic bases such as amines (e.g., triethylamine, N,N-diisopropylethylamine, N-methylmorpholine, 4-dimethylaminopyridine, DBU (1,8-diazabicyclo[5.4.0]undec-7-ene), DBN (1,5-diazabicyclo[4.3.0]non-5-ene)), basic heterocyclic compounds (e.g., pyridine, imidazole, 2,6-lutidine) and the like; and the like can be mentioned.

Of the above-mentioned base, triethylamine, N,N-diisopropylethylamine, pyridine and the like are preferable.

The amount of the base to be used is, for example, from catalytic amount to 5 mol, per 1 mol of compound (II).

The amount of compound (III) to be used is generally 1 to 10 mol per 1 mol of compound (II).

The reaction temperature is generally −20° C. to 200° C., preferably room temperature (1 to 30° C., hereinafter the same) to 100° C. The reaction time is, for example, 1 to 24 hr.

The aforementioned compound (II) can be produced by a method known per se, for example, the method described in WO 2004/092181 or a method analogous thereto.

The aforementioned compound (III) can be produced by a method known per se, for example, the method described in WO 2004/072018 or a method analogous thereto.

[Production Method 2]

Compound (I) can also be produced, for example, by subjecting compound (IV) and compound (III) to an amidation reaction, and subjecting the obtained compound (V) to a cyclization reaction.

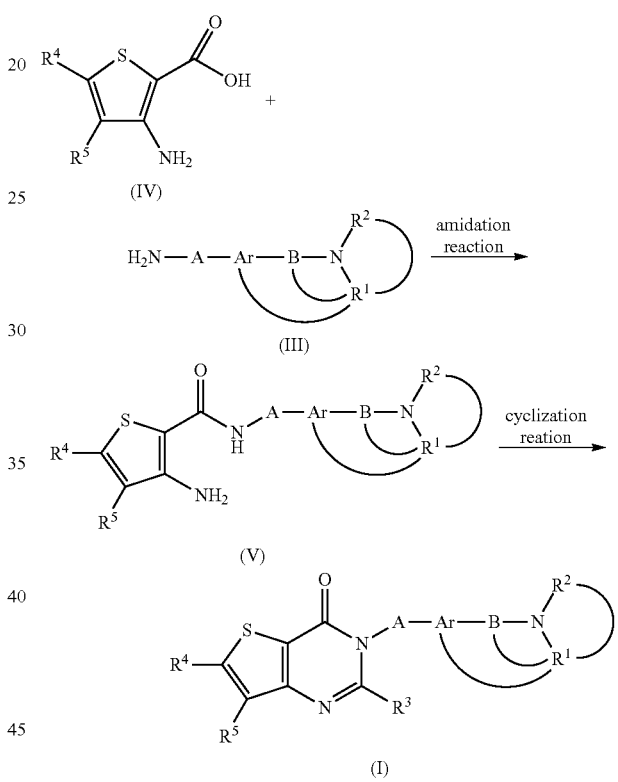

(IV)

(III)

(V)

(I)

wherein the symbols in the formula are as defined above.

The "amidation reaction" includes "a method using a dehydration condensing agent" and "a method using a reactive derivative of carboxy group" described below.

i) Method Using a Dehydration Condensing Agent

In this method, compound (IV), compound (III) and a dehydration condensing agent are reacted in an inert solvent.

As the "dehydration condensing agent", for example, dicyclohexylcarbodiimide (DCC), 1-ethyl-3-(3-dimethylaminopropyl)carbodiimide hydrochloride (WSC) and the is like can be mentioned. Of these, WSC is preferable.

The amount of the dehydration condensing agent to be used is, for example, 1 to 2 mol per 1 mol of compound (IV).

As the "inert solvent", for example, nitrile solvent (preferably acetonitrile), amide solvent (preferably DMF), halogenated hydrocarbon solvent (preferably dichloromethane), ether solvent (preferably THF) and the like can be mentioned. These may be used in a mixture of two or more kinds thereof at an appropriate ratio.

This reaction may be performed in the copresence of 1-hydroxybenzotriazole (HOBt) and (or) a base as necessary.

As the "base", those exemplified for the aforementioned Production Method 1 can be used. Particularly, triethylamine, N,N-diisopropylethylamine, 4-dimethylaminopyridine and the like are preferable.

The amount of each of HOBt and the base to be used is, for example, from catalytic amount to 5 mol, per 1 mol of compound (IV).

The amount of compound (III) to be used is generally 1 to 5 mol per 1 mol of compound (IV).

The reaction temperature is generally −20° C. to 50° C., preferably 0° C. to room temperature (1 to 30° C.). The reaction time is, for example, 1 to 24 hr.

ii) Method Using a Reactive Derivative of Carboxy Group

In this method, reactive derivative of compound (IV) and compound (III) are reacted in an inert solvent.

As the "reactive derivative" of compound (IV), for example, acid halide (e.g., acid chloride, acid bromide), mixed acid anhydride (e.g., acid anhydride with $C_{1-6}$ alkyl-carboxylic acid, $C_{6-10}$ aryl-carboxylic acid or $C_{1-6}$ alkyl-carbonic acid), activated ester (e.g., ester with phenol optionally having substituent(s), 1-hydroxybenzotriazole or N-hydroxysuccinimide) and the like can be mentioned.

As the "substituent" of the "phenol optionally having substituent(s)", for example, halogen atom, nitro group, $C_{1-6}$ alkyl group optionally substituted by 1 to 3 halogen atoms, $C_{1-6}$ alkoxy group optionally substituted by 1 to 3 halogen atoms and the like can be mentioned. The number of the substituents is, for example, 1 to 5.

As specific examples of "phenol optionally having substituent(s)", for example, phenol, pentachlorophenol, pentafluorophenol, p-nitrophenol and the like can be mentioned. The reactive derivative is preferably an acid halide.

As the "inert solvent", for example, ether solvent, halogenated hydrocarbon solvent, aromatic solvent, nitrile solvent, amide solvent, ketone solvent, sulfoxide solvent, water and the like can be mentioned. These may be used in a mixture of two or more kinds thereof at an appropriate ratio. Particularly, acetonitrile, THF, dichloromethane, chloroform and the like are preferable.

This reaction may be performed in the copresence of a base as necessary. As the "base", those exemplified for the aforementioned Production Method 1 can be used. Particularly, sodium hydride, potassium carbonate, sodium carbonate, sodium hydroxide, potassium hydroxide, sodium hydrogen carbonate, potassium hydrogen carbonate, triethylamine, pyridine and the like are preferable.

The amount of the base to be used is generally 1 to 10 mol, preferably 1 to 3 mol, per 1 mol of compound (IV).

The amount of compound (III) to be used is generally 1 to 5 mol, preferably 1 to 3 mol, per 1 mol of compound (IV).

The reaction temperature is generally −20° C. to 50° C., preferably 0° C. to room temperature. The reaction time is generally 5 min to 40 hr, preferably 1 to 18 hr.

The aforementioned compound (IV) can be produced by a method known per se, for example, the method described in WO 2001/058890 or a method analogous thereto.

The "cyclization reaction" is performed by reacting, for example, compound (V) with compound (VI) represented by the formula: $R^3$—COOH($R^3$ is as defined above).

Compound (VI) may be used as a corresponding acid anhydride, and further, compound (VI) may be used as a mixture of an acid anhydride corresponding to compound (VI) and compound (VI) at an appropriate ratio.

This reaction may be performed in an inert solvent where necessary. As the "inert solvent", for example, alcohol solvent, ether solvent, halogenated hydrocarbon solvent, aromatic solvent, nitrile solvent, amide solvent, sulfoxide solvent and the like can be mentioned. These may be used in a mixture of two or more kinds thereof at an appropriate ratio. Particularly, ethanol, THF, N,N-dimethylformamide, dimethyl sulfoxide and the like are preferable.

The amount of compound (VI) to be used is generally 1 to 10 mol per 1 mol of compound (V). In addition, using compound (VI) in large excess, a reaction using compound (VI) itself as a solvent can also be performed.

The reaction temperature is generally −20° C. to 200° C., preferably room temperature to 100° C. The reaction time is, for example, 1 to 48 hr.

The aforementioned compound (VI) can be produced by a method known per se.

[Production Method 3]

Of compounds (I), compound (Ib) wherein $R^3$ is a hydroxy group can be produced, for example, by subjecting compound (VII) to a cyclization reaction.

$$R^4 \underset{R^5}{\overset{S}{\diagdown}} \underset{NH_2}{\overset{O}{\diagdown}} N-A-Ar-B-N\underset{R^1}{\overset{R^2}{\diagdown}} \xrightarrow{\text{cyclization reaction}}$$

(VII)

$$R^4 \underset{R^5}{\overset{S}{\diagdown}} \underset{N}{\overset{O}{\diagdown}} N-A-Ar-B-N\underset{R^1}{\overset{R^2}{\diagdown}}$$
$$\phantom{xxxxxx} OH$$

(Ib)

wherein the symbols in the formula are as defined above.

The "cyclization reaction" can be performed, for example, is by reacting compound (VII) and phosgene in an inert solvent.

As the "phosgene", for example, phosgene, trichloromethyl chloroformate, triphosgene and the like can be mentioned.

The amount of the "phosgene" to be used is generally 0.3 to 5 mol per 1 mol of compound (VII).

As the "inert solvent", for example, alcohol solvent, ether solvent, halogenated hydrocarbon solvent, aromatic solvent, nitrile solvent, amide solvent, sulfoxide solvent and the like can be mentioned. These may be used in a mixture of two or more kinds thereof at an appropriate ratio. Particularly, 1,2-dichloroethane, THF, acetonitrile and the like are preferable.

This reaction may be performed in the copresence of a base as necessary. As the "base", those exemplified for the aforementioned Production Method 1 can be used. Particularly, triethylamine, N,N-diisopropylethylamine, pyridine and the like are preferable. The amount of the base to be used is, for example, from catalytic amount to 5 mol, per 1 mol of compound (VII).

The reaction temperature is generally −78° C. to 100° C., preferably −20° C. to room temperature. The reaction time is, for example, 0.5 to 24 hr.

As the aforementioned "alcohol solvent", for example, methanol, ethanol, isopropanol, tert-butanol and the like can be used.

As the aforementioned "ether solvent", for example, diethyl ether, tetrahydrofuran (THF), 1,4-dioxane, 1,2-dimethoxyethane and the like can be used.

As the aforementioned "halogenated hydrocarbon solvent", for example, dichloromethane, chloroform, 1,2-dichloroethane, carbon tetrachloride and the like can be used.

As the aforementioned "aromatic solvent", for example, benzene, toluene, xylene, pyridine and the like can be used.

As the aforementioned "hydrocarbon solvent", for example, hexane, pentane, cyclohexane and the like can be used.

As the aforementioned "amide solvent", for example, N,N-dimethylformamide (DMF), N,N-dimethylacetamide, N-methylpyrrolidone and the like can be used.

As the aforementioned "ketone solvent", for example, acetone, methyl ethyl ketone and the like can be used.

As the aforementioned "sulfoxide solvent", for example, dimethyl sulfoxide (DMSO) and the like can be used.

As the aforementioned "nitrile solvent", for example, acetonitrile, propionitrile and the like can be used.

In compound (I) thus obtained, the functional group in a molecule can also be converted to the object functional group by combining chemical reactions known per se. As the examples of such chemical reaction, oxidation reaction, reduction reaction, alkylation reaction, hydrolysis reaction, amination reaction, esterification reaction, aryl-coupling reaction, deprotection reaction and the like can be mentioned.

In each of the aforementioned reactions, when the starting compound has amino group, carboxyl group, hydroxy group or carbonyl group as a substituent, a protecting group generally used in peptide chemistry and the like may be introduced into these groups. By removing the protecting group as necessary after the reaction, the objective compound can be obtained.

As the amino-protecting group, for example, formyl group, $C_{1-6}$ alkyl-carbonyl group (e.g., acetyl, propionyl), $C_{1-6}$ alkoxy-carbonyl group (e.g., methoxycarbonyl, ethoxycarbonyl, tert-butoxycarbonyl), benzoyl group, $C_{7-10}$ aralkyl-carbonyl group (e.g., benzylcarbonyl), $C_{7-14}$ aralkyloxy-carbonyl group (e.g., benzyloxycarbonyl, 9-fluorenylmethoxycarbonyl), trityl group, phthaloyl group, N,N-dimethylaminomethylene group, substituted silyl group (e.g., trimethylsilyl, triethylsilyl, dimethylphenylsilyl, tert-butyldimethylsilyl, tert-butyldiethylsilyl), $C_{2-6}$ alkenyl group (e.g., 1-allyl) and the like can be used. These groups are optionally substituted by 1 to 3 substituents selected from halogen atom, $C_{1-6}$ alkoxy group and nitro group.

As the carboxyl-protecting group, for example, $C_{1-6}$ alkyl group, $C_{7-11}$ aralkyl group (e.g., benzyl), phenyl group, trityl group, substituted silyl group (e.g., trimethylsilyl, triethylsilyl, dimethylphenylsilyl, tert-butyldimethylsilyl, tert-butyldiethylsilyl), $C_{2-6}$ alkenyl group (e.g., 1-allyl) and the like can be used. These groups are optionally substituted by 1 to 3 substituents selected from halogen atom, $C_{1-6}$ alkoxy group and nitro group.

As the hydroxy-protecting group, for example, $C_{1-6}$ alkyl group, phenyl group, trityl group, $C_{7-10}$ aralkyl group (e.g., benzyl), formyl group, $C_{1-6}$ alkyl-carbonyl group (e.g., acetyl, propionyl), benzoyl group, $C_{7-10}$ aralkyl-carbonyl group (e.g., benzylcarbonyl), 2-tetrahydropyranyl group, 2-tetrahydrofuranyl group, substituted silyl group (e.g., trimethylsilyl, triethylsilyl, dimethylphenylsilyl, tert-butyldimethylsilyl, tert-butyldiethylsilyl), $C_{2-6}$ alkenyl group (e.g., 1-allyl) and the like can be used. These groups are optionally substituted by 1 to 3 substituents selected from halogen atom, $C_{1-6}$ alkoxy group and nitro group.

As the carbonyl-protecting group, for example, cyclic acetal (e.g., 1,3-dioxane), acyclic acetal (e.g., di-$C_{1-6}$ alkyl acetal) and the like can be used.

Removal of the above protecting groups can be carried out in accordance with methods known per se such as those described in Protective Groups in Organic Synthesis, published by John Wiley and Sons (1980) and the like. For instance, the methods using acid, base, ultraviolet light, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide, etc.) and the like, a reduction method and the like can be used.

The compound (I) can be isolated and purified by methods known per se such as solvent extraction, changing of liquid properties, transdissolution, crystallization, recrystallization, chromatography, and the like. It is also possible to isolate and purify the starting material compounds of a compound (I), or their salts using the same known methods as above, but they can also be used as starting materials in the next process as a reaction mixture without being isolated.

Inasmuch as compound (I) and a prodrug thereof (hereinafter abbreviated as the compound of the present invention) has a superior MCH receptor antagonistic action, it is useful as an agent for the prophylaxis or treatment of diseases caused by MCH. In addition, the compound of the present invention shows low toxicity (e.g., acute toxicity, chronic toxicity, genetic toxicity, reproductive toxicity, cardiac toxicity (e.g., human ether-a-go-go related gene (HERG) inhibitory activity), drug interaction, carcinogenicity, phototoxicity), and superior oral absorption performance and transfer into the brain.

Accordingly, the compound of the present invention is safely administered as an agent for the prophylaxis or treatment of diseases caused by MCH to mammals (e.g., rat, mouse, guinea pig, rabbit, sheep, horse, pig, cow, monkey, human).

The diseases caused by MCH include, for example, obesity [e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity and the like], hyperphagia, emotional disorder, sexual dysfunction, depression, anxiety and the like.

The compound of the present invention is useful as an is agent for the prophylaxis or treatment of diabetes (e.g., type 1 diabetes, type 2 diabetes, gestational diabetes, obesity type diabetes), diabetic complications (e.g., diabetic retinopathy, diabetic neuropathy, diabetic nephropathy, macroangiopathy, osteopenia), hyperlipidemia (e.g., hypertriglyceridemia, hypercholesterolemia, hypo-high density lipoproteinemia, postprandial hyperlipidemia), arteriosclerosis, impaired glucose tolerance, glucose metabolism disorder, lipid metabolism disorder, insulin resistance syndrome, syndrome X, metabolic syndrome (e.g., a state having at least one of type 2 diabetes, impaired glucose tolerance and insulin resistance and at least two of obesity, lipid metabolism disorder, hypertension and microalbuminuria), inflammatory disease (e.g., chronic rheumatoid arthritis, spondylitis deformans, osteoarthritis, lumbago, gout, neuralgia, pharyngolaryngitis, cystitis, hepatitis (including nonalcoholic steatohepatitis), pneumonia, pancreatitis, inflammatory colitis, ulcerative colitis, coxitis) and the like.

Furthermore, the compound of the present invention is also useful as a feeding deterrent.

The compound of the present invention can also be concurrently used with diet therapy (e.g., diet therapy for diabetes), or an exercise therapy.

The compound of the present invention can be used for the prophylaxis or treatment of pigmentation disorder based on abnormality of melanin or melanocyte. Here, as the pigmentation disorder, pigment proliferation, pigment decrease and the like can be mentioned. As the pigment proliferation, drug pigmentation caused by antitumor agent and the like; chromatosis and incompetence of pigment associated with diseases such as endocrine metabolism disorder (e.g., Addison's disease), genetic diseases, chronic hepatopathy, kidney failure, acanthosis nigricans, systemic scleroderma and the like; and the like can be mentioned. As the pigment decrease, phenylketonuria, systemic or localized albinism, foliaceous leukoderma or leukoderma vulgaris associated with tuberous sclerosis; depigmentation associated with systemic scleroderma and the like can be mentioned.

The compound of the present invention can be used for the prophylaxis or treatment of depigmentation due to chloasma, ephelides, sunburn and the like; and further, hyperpigmentation or hypopigmentation for cosmetic purposes.

The compound of the present invention has low toxicity, and can be used as an agent for the prophylaxis or treatment of the aforementioned various diseases directly as it is or as a pharmaceutical composition containing a pharmacologically acceptable carrier and the like for a mammal (e.g., human, mouse, rat, rabbit, dog, cat, bovine, horse, swine, monkey).

As the pharmacologically acceptable carrier, various organic or inorganic carrier substances conventionally used as a preparation material can be mentioned. For example, excipient, lubricant, binder and disintegrant for solid preparations; solvent, solubilizing agent, suspending agent, isotonicity agent, buffer and soothing agent for liquid preparations and the like can be added. Where necessary, preparation additives such as preservatives, antioxidants, coloring agents, sweetening agents and the like can be used.

As preferable examples of the excipient, lactose, saccharose, D-mannitol, D-sorbitol, starch, pregelatinized starch, dextrin, crystalline cellulose, low-substituted hydroxypropylcellulose, sodium carboxymethylcellulose, gum arabic, pullulan, light anhydrous silicic acid, synthetic aluminum silicate, magnesium aluminometasilicate and the like can be mentioned.

As preferable examples of the lubricant, magnesium stearate, calcium stearate, talc, colloidal silica and the like can be mentioned.

As preferable examples of the binder, pregelatinized starch, sucrose, gelatin, gum arabic, methylcellulose, carboxymethylcellulose, sodium carboxymethylcellulose, crystalline cellulose, saccharose, D-mannitol, trehalose, dextrin, pullulan, hydroxypropylcellulose, hydroxypropylmethylcellulose, polyvinylpyrrolidone and the like can be mentioned.

As preferable examples of the disintegrant, lactose, saccharose, starch, carboxymethylcellulose, calcium carboxymethylcellulose, croscarmellose sodium, sodium carboxymethyl starch, light anhydrous silicic acid, low-substituted hydroxypropylcellulose and the like can be mentioned.

As preferable examples of the solvent, water for injection, physiological saline, Ringer's solution, alcohol, propylene glycol, polyethylene glycol, sesame oil, corn oil, olive oil, cottonseed oil and the like can be mentioned.

As preferable examples of the solubilizing agent, polyethylene glycol, propylene glycol, D-mannitol, trehalose, benzyl benzoate, ethanol, trisaminomethane, cholesterol, triethanolamine, sodium carbonate, sodium citrate, sodium salicylate, sodium acetate and the like can be mentioned.

As preferable examples of the suspending agent, surfactant such as stearyltriethanolamine, sodium lauryl sulfate, lauryl aminopropionate, lecithin, benzalkonium chloride, benzethonium chloride, glyceryl monostearate and the like; for example, hydrophilic polymer such as polyvinyl alcohol, polyvinylpyrrolidone, sodium carboxymethylcellulose, methylcellulose, hydroxymethylcellulose, hydroxyethylcellulose, hydroxypropylcellulose and the like; polysorbates, polyoxyethylene hydrogenated castor oil and the like can be mentioned.

As preferable examples of the isotonicity agent, sodium chloride, glycerol, D-mannitol, D-sorbitol, glucose and the like can be mentioned.

As preferable examples of the buffer, buffers such as phosphate, acetate, carbonate, citrate and the like, and the like can be mentioned.

As preferable examples of the soothing agent, benzyl alcohol and the like can be mentioned.

As preferable examples of the preservative, p-hydroxybenzoates, chlorobutanol, benzyl alcohol, phenethyl alcohol, dehydroacetic acid, sorbic acid and the like can be mentioned.

As preferable examples of the antioxidant, sulfite, ascorbic acid salt and the like can be mentioned.

As preferable examples of the coloring agent, water-soluble food tar color (e.g., food colors such as Food Color Red No. 2 and No. 3, Food Color Yellow No. 4 and No. 5, Food Color Blue No. 1 and No. 2 and the like), water-insoluble lake dye (e.g., aluminum salt of the aforementioned water-soluble food tar color), natural dye (e.g., β-carotene, chlorophyll, red iron oxide) and the like can be mentioned.

As preferable examples of the sweetening agent, saccharin sodium, dipotassium glycyrrhizinate, aspartame, stevia and the like can be mentioned.

As the dosage form of the aforementioned pharmaceutical composition, for example, oral preparations such as tablet (including sublingual tablet, orally disintegrating tablet), capsule (including soft capsule, microcapsule), granule, powder, troche, syrup, emulsion, suspension and the like; and parenteral preparations such as injection (e.g., subcutaneous injection, intravenous injection, intramuscular injection, intraperitoneal injection, drip infusion), external preparation (e.g., percutaneous preparation, ointment), suppository (e.g., rectal suppository, vaginal suppository), pellet, transnasal preparation, pulmonary preparation (inhalant), eye drop and the like can be mentioned, which can be orally or parenterally administered safely.

These preparations may be controlled-release preparation (e.g., sustained-release microcapsule) such as immediate-release preparation, sustained-release preparation and the like.

The pharmaceutical composition can be produced by a method conventionally used in the technical field of pharmaceutical preparation such as the method described in the Japanese Pharmacopoeia. Specific production methods of the preparation are described in detail below.

While the content of the compound of the present invention in the pharmaceutical composition varies depending on the dosage form, dose of the compound of the present invention and the like, it is, for example, about 0.1 to 100 wt. %.

The dose of the compound of the present invention is appropriately determined according to the subject of administration, administration route, disease and the like.

For example, the daily dose of the compound of the present invention for oral administration to an adult patient (body weight about 60 kg) with obesity is about 0.1 to about 500 mg, preferably about 1 to about 100 mg, more preferably about 5 to about 100 mg. This amount can be administered at once or in several portions for one day.

The compound of the present invention can be used in combination with a concomitant drug that does not adversely influence the compound of the present invention for the purpose of, for example, enhancing the MCH receptor antagonistic action of the compound of the present invention, reduction of the amount of the compound of the present invention to be used and the like. As such concomitant drug, for example, "agent for treating diabetes", "agent for treating diabetic complication", "antiobesity agent other than MCH receptor antagonist", "agent for treating hypertension", "agent for treating hyperlipidemia", "agent for treating arthritis", "antianxiety agent", "antidepressant", "antithrombotic agent", "agent for treating osteoporosis" and the like can be mentioned. Two or more kinds of these concomitant drugs may be used in combination at an appropriate ratio.

As the above-mentioned "agent for treating diabetes", insulin preparations (e.g., animal insulin preparations extracted from pancreas of bovine and swine; human insulin preparations genetically synthesized using *Escherichia coli* or yeast; zinc insulin; protamine zinc insulin; fragment or derivative of insulin (e.g., INS-1), oral insulin preparation and the like), insulin sensitizers (e.g., pioglitazone or a salt thereof (preferably hydrochloride), rosiglitazone or a salt thereof (preferably maleate), Reglixane (JTT-501), Netoglitazone (MCC-555), DRF-2593, Edaglitazone (BM-13.1258), KRP-297, Rivoglitazone (CS-011), FK-614, compounds described in WO99/58510 (e.g., (E)-4-[4-(5-methyl-2-phenyl-4-oxazolylmethoxy)benzyloxyimino]-4-phenylbutyric acid), compounds described in WO01/38325, Tesaglitazar (AZ-242), Ragaglitazar (N,N-622), Muraglitazar (BMS-298585), ONO-5816, LM-4156, MBX-102, Naveglitazar (LY-519818), MX-6054, LY-510929, Balaglitazone (N,N-2344), T-131 or a salt thereof, THR-0921), PPARγ agonists, PPARγ antagonists, PPARγ/α dual agonists, α-glucosidase inhibitors (e.g., voglibose, acarbose, miglitol, emiglitate), biguanides (e.g., phenformin, metformin, buformin or a salt thereof (e.g., hydrochloride, fumarate, succinate)), insulin secretagogues [sulfonylurea (e.g., tolbutamide, glibenclamide, gliclazide, chlorpropamide, tolazamide, acetohexamide, glyclopyramide, glimepiride, glipizide, glybuzole), repaglinide, senaglinide, nateglinide, mitiglinide or calcium salt hydrate thereof], GPR40 agonists, GLP-1 receptor agonists [e.g., GLP-1, GLP-1MR agent, N,N-2211, AC -2993 (exendin-4), BIM-51077, Aib(8,35)hGLP-1 (7,37)NH$_2$, CJC-1131], amylin agonists (e.g., pramlintide), phosphotyrosine phosphatase inhibitors (e.g., sodium vanadate), dipeptidyl peptidase IV inhibitors (e.g., NVP-DPP-278, PT-100, P32/98, Vidagliptin (LAF-237), P93/01, TS-021, Sitagliptin (MK-431), Saxagliptin (BMS-477118), Denagliptin (823093), T-6666), β3 agonists (e.g., AJ-9677), gluconeogenesis inhibitors (e.g., glycogen phosphorylase inhibitors, glucose-6-phosphatase inhibitors, glucagon antagonists), SGLT (sodium-glucose cotransporter) inhibitors (e.g., T-1095), 11β-HSD1 inhibitors (e.g., BVT-3498), adiponectin or agonists thereof, IKK inhibitors (e.g., AS-2868), leptin resistance improving drugs, somatostatin receptor agonists (e.g., compounds described in WO01/25228, WO03/42204, WO98/44921, WO98/45285, WO99/22735) and the like can be mentioned.

As the above-mentioned "agent for treating diabetic complication", for example, aldose reductase inhibitors (e.g., tolrestat, epalrestat, zenarestat, zopolrestat, minalrestat, fidarestat, CT-112), neurotrophic factors and enhancers thereof (e.g., NGF, NT-3, BDNF, neurotrophin production/secretion promoting agents described in WO01/14372 (e.g., 4-(4-chlorophenyl)-2-(2-methyl-1-imidazolyl)-5-[3-(2-methylphenoxy)propyl]oxazole)), nerve regeneration promoting agents (e.g., Y-128), protein kinase (PK) C inhibitors (e.g., ruboxistaurin mesylate), AGE inhibitors (e.g., ALT946, pimagedine, N-phenacylthiazolium bromide (ALT766), pimagedline (ALT-711), EXO-226, Pyridorin, pyridoxamine), active oxygen scavengers (e.g., thioctic acid), cerebral vasodilators (e.g., tiapride, mexiletine), somatostatin receptor agonists (e.g., BIM23190), apoptosis signal regulating kinase-1 (ASK-1) inhibitors can be mentioned.

As the above-mentioned "antiobesity agent other than MCH receptor antagonist", for example, central nervous system antiobesity agents [e.g., dexfenfluramine, fenfluramine, phentermine, sibutramine, anfepramone, dexamphetamine, mazindol, phenylpropanolamine, clobenzorex; neuropeptide Y antagonists (e.g., CP-422935); cannabinoid receptor antagonists (e.g., SR-141716, SR-147778); ghrelin antagonists], pancreatic lipase inhibitors (e.g., orlistat, ATL-962), β3 agonists (e.g., AJ-9677), anorectic peptides (e.g., leptin, CNTF (ciliary neurotrophic factor)), cholecystokinin agonists (e.g., lintitript, FPL-15849), feeding deterrents (e.g., P-57) and the like can be mentioned.

As the above-mentioned "agent for treating hypertension", for example, angiotensin converting enzyme inhibitors (e.g., captopril, enalapril, alacepril, delapril (hydrochloride), lisinopril, imidapril, benazepril, cilazapril, temocapril, trandolapril), angiotensin II receptor antagonists (e.g., candesartan cilexetil, losartan, eprosartan, valsartan, telmisartan, irbesartan, tasosartan, 1-[[2'-(2,5-dihydro-5-oxo-4H-1,2,4-oxadiazol-3-yl)biphenyl-4-yl]methyl]-2-ethoxy -1H-benzimidazole -7-carboxylic acid), calcium antagonists (e.g., manidipine, nifedipine, amlodipine, efonidipine, nicardipine), potassium channel openers (e.g., levcromakalim, L-27152, AL 0671, NIP-121), clonidine and the like can be mentioned.

As the above-mentioned "agent for treating hyperlipidemia", for example, HMG-CoA reductase inhibitors (e.g., pravastatin, simvastatin, lovastatin, atorvastatin, fluvastatin, pitavastatin, rosuvastatin or a salt thereof (e.g., sodium salt, calcium salt)), squalene synthase inhibitors (e.g., compounds described in WO97/10224, for example, N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidine-4-acetic acid), fibrate compounds (e.g., bezafibrate, clofibrate, simfibrate, clinofibrate), ACAT inhibitors (e.g., Avasimibe, Eflucimibe), anion exchange resins (e.g., colestyramine), probucol, nicotinic acid drugs (e.g., nicomol, niceritrol), ethyl icosapentate, phytosterols (e.g., soysterol, γ-oryzanol) and the like can be mentioned.

As the above-mentioned "agent for treating arthritis", for example, ibuprofen and the like can be mentioned.

As the above-mentioned "antianxiety agent", for example, chlordiazepoxide, diazepam, oxazolam, medazepam, cloxazolam, bromazepam, lorazepam, alprazolam, fludiazepam and the like can be mentioned.

As the above-mentioned "antidepressant", for example, fluoxetine, fluvoxamine, imipramine, paroxetine, sertraline and the like can be mentioned.

As the above-mentioned "antithrombotic agent", for example, heparin (e.g., heparin sodium, heparin calcium, dalteparin sodium), warfarin (e.g., warfarin potassium), antithrombin drugs (e.g., argatroban), thrombolytic agents (e.g., urokinase, tisokinase, alteplase, nateplase, monteplase, pamiteplase), platelet aggregation inhibitors (e.g., ticlopidine hydrochloride, cilostazol, ethyl icosapentate, beraprost sodium, sarpogrelate hydrochloride) and the like can be mentioned.

As the above-mentioned "agent for treating osteoporosis", for example, alfacalcidol, calcitriol, elcatonin, calcitonin salmon, estriol, ipriflavone, risedronate disodium, pamidronate disodium, alendronate sodium hydrate, incadronate disodium and the like can be mentioned.

The administration time of the aforementioned concomitant drug is not limited, and the compound of the present invention and the concomitant drug can be administered to an administration subject simultaneously, or may be administered at staggered times. The dosage of the concomitant drug may be determined according to the dose clinically used, and can be appropriately selected depending on an administration subject, administration route, disease, combination and the like.

The administration mode of the concomitant drug is not particularly limited, and the compound of the present invention and the concomitant drug only need to be combined on administration. Examples of such administration mode include the following:
(1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (for example, administration in the order of the compound of the present invention and the concomitant drug, or in the reverse order) and the like.

The compounding ratio of the compound of the present invention to the concomitant drug can be appropriately selected depending on the administration subject, administration route, diseases and the like. For example, when the subject of administration is human, 0.01 to 100 parts by weight of the concomitant drug can be used per 1 part by weight of the compound of the present invention.

The present invention is described in detail by way of the following Reference Examples, Examples, Formulation Example and Experimental Example. These are not intended to restrict the present invention, and may be modified within the range not deviating from the scope of this invention.

EXAMPLES

The "room temperature" in the following Reference Examples and Examples means a temperature of 1° C. to 30° C. For drying an organic layer, anhydrous magnesium sulfate or anhydrous sodium sulfate was employed. Unless otherwise specifically indicated, "%" means percent by weight.

The infrared absorption spectrum was measured using Fourier transform infrared spectrophotometer by diffuse reflectance method.

FABMS (pos) is mass spectrum measured by the (+) method in the Fast Atom Bombardment Mass Spectrometry.

The abbreviations used in the present specification mean the following.
Ac: acetyl
Me: methyl
Et: ethyl
$Bu^t$: tert-butyl
Boc: tert-butoxycarbonyl
s: singlet
d: doublet
t: triplet
q: quartet
dd: double doublet
dt: double triplet
m: multiplet
br: broad
J: coupling constant
Hz: Hertz
$CDCl_3$: deuterated chloroform
THF: tetrahydrofuran
DMF: N,N-dimethylformamide
DMSO: dimethyl sulfoxide
$^1$H-NMR: proton nuclear magnetic resonance
IR: infrared absorption spectrum Reference Example 1

2-chloro-1-[3-(trifluoroacetyl)-2,3,4,5-tetrahydro-1H-3-benzazepin-7-yl]ethanone

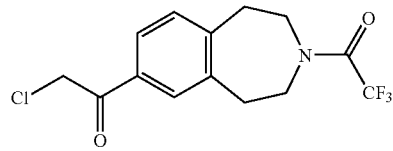

To a solution of chloroacetyl chloride (7.0 g) in dichloroethane (50 ml) was added aluminum chloride (8.2 g) at room temperature, and then a solution of 3-(trifluoroacetyl)-2,3,4,5-tetrahydro-1H-3-benzazepine (3.0 g) in dichloroethane (50 ml) was added. The obtained mixture was stirred at room temperature for 3 hr, and poured into ice-cooled 1N is hydrochloric acid (80 ml). Dichloroethane was evaporated under reduced pressure, and the residue was extracted with ethyl acetate. The extract was washed with saturated brine, dried over anhydrous sodium sulfate, and concentrated under reduced pressure. The residue was recrystallized from ethyl acetate-hexane (1:1, volume ratio) to give the title compound (3.5 g) as a colorless powder.
melting point 170-172° C.
Elemental analysis ($C_{14}H_{13}ClF_3NO_2$)
Calcd.: C, 52.60; H, 4.10; N, 4.38.
Found: C, 52.53; H, 4.02; N, 4.19.

Reference Example 2

2-diformylamino-1-[3-(trifluoroacetyl)-2,3,4,5-tetrahydro-1H-3-benzazepin-7-yl]ethanone

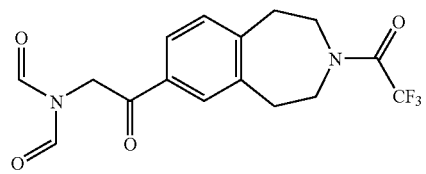

The compound (1 g) obtained in Reference Example 1, sodium diformylamide (0.3 g), tetrahydrofuran (5 ml) and acetonitrile (10 ml) were stirred overnight at 60° C. The reaction mixture was diluted with ethyl acetate (100 ml), washed with water and saturated brine, dried over anhydrous sodium sulfate, and concentrated under reduced pressure. The residue was purified by column chromatography [developing solvent:ethyl acetate-hexane (1:1, volume ratio)] to give the title compound (0.64 g) as a colorless powder.

melting point 152-153° C.

Elemental analysis ($C_{16}H_{15}F_3N_2O_4$)

Calcd.: C, 53.94; H, 4.24; N, 7.86.

Found: C, 53.92; H, 4.21; N, 7.80.

Reference Example 3

2-amino-1-[3-(trifluoroacetyl)-2,3,4,5-tetrahydro-1H-3-benzazepin-7-yl]ethanone hydrochloride

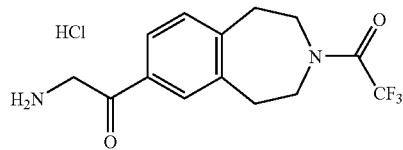

The compound (0.6 g) obtained in Reference Example 2 and a solution (10%) of hydrogen chloride in methanol were stirred at room temperature for 2 hr. The solvent was evaporated under reduced pressure, and the residue was washed with ethyl acetate to give the title compound (0.5 g) as a colorless powder.

melting point 270-275° C.

Elemental analysis ($C_{14}H_{16}ClF_3N_2O_2 \cdot 0.2H_2O$)

Calcd.: C, 49.41; H, 4.86; N, 8.23.

Found: C, 49.28; H, 4.92; N, 8.11.

Reference Example 4

N-benzyl-2,2,2-trifluoro-N-methylacetamide

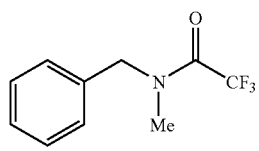

A mixture of N-methylbenzylamine (5 g) and trifluoroacetic anhydride (15 ml) was stirred under ice-cooling for 30 min. The reaction mixture was poured into ice water, and the precipitate was collected by filtration to give the title compound (8.2 g) as a colorless oil.

IR $\nu_{max}$(KBr) cm$^{-1}$: 1697 (C=O).

$^1$H-NMR (CDCl$_3$) δ: 2.92 (⅓×3H, s), 3.05 (⅔×3H, q, J=1.5 Hz), 4.63-4.64 (2H, m), 7.20-7.27 (2H, m), 7.32-7.39 (3H, m).

Reference Example 5

N-[4-(chloroacetyl)benzyl]-2,2,2-trifluoro-N-methylacetamide

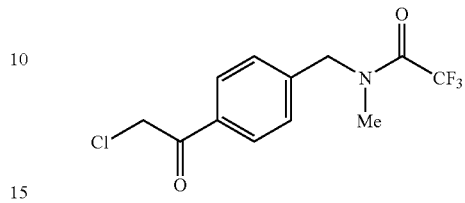

To a solution of chloroacetyl chloride (12.8 g) in methylene chloride (110 ml) was added aluminum chloride (15.2 g) at room temperature, and then a solution of the compound (8.2 g) obtained in Reference Example 4 in methylene chloride (50 ml) was added. The obtained mixture was stirred at 40° C. for 1 hr, and poured into ice water. Methylene chloride was evaporated under reduced pressure, and the residue was extracted with ethyl acetate. The extract was washed with saturated brine, dried over anhydrous sodium sulfate, and concentrated under reduced pressure. The residue was purified by column chromatography [developing solvent:ethyl acetate-hexane (1:3, volume ratio)] to give the title compound (7.2 g) as a pale-yellow oil.

IR $\nu_{max}$(KBr) cm$^{-1}$: 1695 (C=O).

$^1$H-NMR (CDCl$_3$) δ: 2.97 (⅓×3H, s), 3.10 (⅔×3H, q, J=1.5 Hz), 4.69 (⅔×2H, s), 4.70 (⅓×2H, s), 4.71 (2H, s), 7.33-7.40 (2H, m), 7.96-8.01 (2H, m).

Reference Example 6

N-[4-(N,N-diformylglycyl)benzyl]-2,2,2-trifluoro-N-methylacetamide

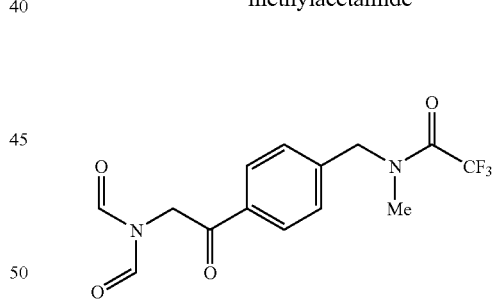

The compound (7.2 g) obtained in Reference Example 5, sodium diformylamide (2.5 g) and acetonitrile (70 ml) were stirred overnight at 60° C. The reaction mixture was diluted with ethyl acetate (100 ml), washed with water and saturated brine, dried over anhydrous sodium sulfate, and concentrated under reduced pressure. The residue was purified by column chromatography [developing solvent:ethyl acetate-hexane (3:2, volume ratio)] to give the title compound (5.5 g) as a colorless powder.

IR $\nu_{max}$(KBr) cm$^{-1}$: 1692 (C=O).

$^1$H-NMR (CDCl$_3$) δ: 2.96 (⅓×3H, s), 3.09 (⅔×3H, q, J=1.5 Hz), 4.70 (⅓×2H, s), 4.71 (⅔×2H, s), 5.08 (⅔×2H, s), 5.09 (⅓×2H, s), 7.34-7.41 (2H, m), 7.96-8.02 (2H, m), 9.04 (2H, s).

Reference Example 7

2,2,2-trifluoro-N-(4-glycylbenzyl)-N-methylacetamide hydrochloride

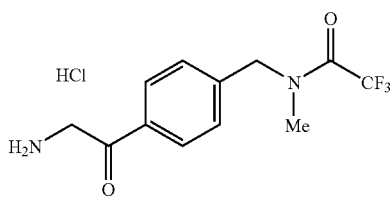

The compound (3 g) obtained in Reference Example 6 and a solution (10%, 30 ml) of hydrogen chloride in methanol were stirred overnight at room temperature. The solvent was evaporated under reduced pressure, and the residue was washed with ethyl acetate to give the title compound (1.6 g) as a colorless powder.
melting point 201-205° C.
$^1$H-NMR (CD$_3$OD) δ: 2.76 (⅓×3H, s), 3.16 (⅔×3H, q, J=1.5 Hz), 4.59-4.76 (4H, m), 7.45-7.50 (2H, m), 8.03-8.15 (2H, m).

Reference Example 8

N-(2,3-dihydro-1H-inden-2-yl)-2,2,2-trifluoroacetamide

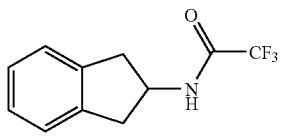

A mixture of 2-aminoindane (5 g) and trifluoroacetic anhydride (15 ml) was stirred under ice-cooling for 30 min. The reaction mixture was poured into ice water, and the precipitate was collected by filtration to give the title compound (4.9 g) as a colorless oil.
melting point 160° C.
Elemental analysis (C$_{11}$H$_{10}$F$_3$NO)
Calcd.: C, 57.64; H, 4.40; N, 6.11.
Found: C, 57.49; H, 4.34; N, 6.07.

Reference Example 9

N-(2,3-dihydro-1H-inden-2-yl)-2,2,2-trifluoro-N-methylacetamide

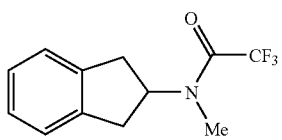

A mixture of the compound (0.5 g, 2.18 mmol) obtained in Reference Example 8, sodium hydride (58 mg, 2.40 mmol), iodomethane (0.37 g, 2.62 mmol) and N,N-dimethylformamide (5 ml) was stirred at room temperature for 1 hr. The reaction was quenched by adding 1N hydrochloric acid (3 ml) to the reaction mixture, and the mixture was extracted with ethyl acetate. The organic layer was washed with 5% aqueous potassium hydrogen sulfate solution, saturated aqueous sodium hydrogen carbonate solution and saturated brine. The organic layer was dried over magnesium sulfate and concentrated under reduced pressure to give the title compound (0.58 g) as a pale-yellow oil.
$^1$H-NMR (300 MHz, CDCl$_3$) δ: 2.89 (½×3H, s), 2.94 (½×3H, q, J=1.8 Hz), 3.00 (½×2H, dd, J=5.7, 16.8 Hz), 3.099 (½×2H, dd, J=6.3, 16.8 Hz), 3.27 (½×2H, dd, J=8.4, 16.8 Hz), 3.30 (½×2H, dd, J=9.0, 16.8 Hz), 4.91-5.01 (½×1H, m), 5.43-5.53 (½×1H, m), 7.18-7.24 (4H, m).

Reference Example 10

N-[5-(chloroacetyl)-2,3-dihydro-1H-inden-2-yl]-2,2,2-trifluoro-N-methylacetamide

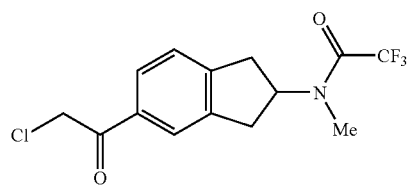

To a solution of chloroacetyl chloride (11.2 g) in methylene chloride (50 ml) was added aluminum chloride (6.1 g) at room temperature, and then a solution of the compound (5 g) obtained in Reference Example 9 in methylene chloride (50 ml) was added. The obtained mixture was stirred at room temperature for 1 hr, and poured into ice water. Methylene chloride was evaporated under reduced pressure and the residue was extracted with ethyl acetate. The extract was washed with saturated brine, dried over anhydrous sodium sulfate, and concentrated under reduced pressure. The residue was purified by recrystallization from ethyl acetate-hexane (1:1, volume ratio) to give the title compound (4.1 g) as a colorless powder.
melting point 130-131° C.
Elemental analysis (C$_{14}$H$_{13}$ClF$_3$NO$_2$)
Calcd.: C, 52.60; H, 4.10; N, 4.38.
Found: C, 52.47; H, 3.92; N, 4.34.

Reference Example 11

N-[5-(N,N-diformylglycyl)-2,3-dihydro-1H-inden-2-yl]-2,2,2-trifluoro-N-methylacetamide

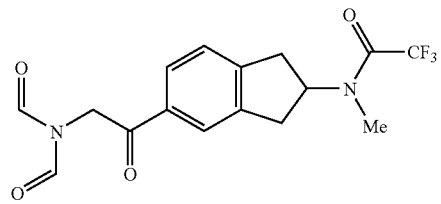

The compound (1.5 g) obtained in Reference Example 10, sodium diformylamide (0.42 g), acetonitrile (15 ml) and tetrahydrofuran (5 ml) were stirred overnight at 60° C. The reaction mixture was diluted with ethyl acetate (100 ml), washed with water and saturated brine, dried over anhydrous sodium sulfate, and concentrated under reduced pressure. The residue was purified by column chromatography [developing solvent:ethyl acetate-hexane (1:1, volume ratio)] to give the title compound (1.2 g) as a colorless powder.

IR $v_{max}$ (KBr) cm$^{-1}$: 1693 (C=O).
$^1$H-NMR (300 MHz, CDCl$_3$) δ: 2.87 (½×3H, s), 2.94 (½×3H, q, J=1.5 Hz), 3.07 (½×2H, dd, J=5.4, 17.1 Hz), 3.15 (½×2H, dd, J=6.0, 17.1 Hz), 3.36 (2H, dd, J=8.1, 17.1 Hz), 4.99-5.04 (½×1H, m), 5.07 (2H, s), 5.44-5.54 (½×1H, m), 7.37 (1H, d, J=8.1 Hz), 7.82-7.85 (2H, m), 9.04 (2H, s).

Reference Example 12

2,2,2-trifluoro-N-(5-glycyl-2,3-dihydro-1H-inden-2-yl)-N -methylacetamide hydrochloride

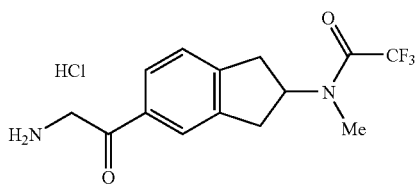

The compound (1.1 g) obtained in Reference Example 11 and a solution (10%, 20 ml) of hydrogen chloride in methanol were stirred overnight at room temperature. The solvent was evaporated under reduced pressure, and the residue was washed with ethyl acetate to give the title compound (0.63 g) as a colorless powder.
melting point 179-182° C.
Elemental analysis (C$_{14}$H$_{16}$ClF$_3$N$_2$O$_2$)
Calcd.: C, 49.94; H, 4.79; N, 8.32.
Found: C, 49.81; H, 4.92; N, 8.62.

Reference Example 13 tert-butyl[2-(4-{[(3S)-3-fluoropyrrolidin-1-yl]methyl}phenyl)ethyl]carbamate

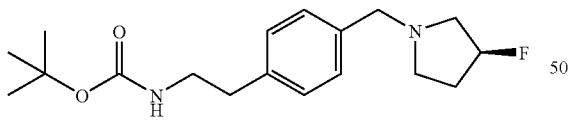

To a solution of tert-butyl{2-[4-(bromomethyl)phenyl]ethyl}carbamate (450 mg, 1.43 mmol) in DMF (4 ml) were added N,N-diisopropylethylamine (0.749 ml, 4.30 mmol) and (3S)-3-fluoropyrrolidine hydrochloride (180 mg, 1.43 mmol), and the mixture was stirred at room temperature for 22 hr. Ethyl acetate was added to the reaction mixture, and the mixture was washed with aqueous sodium hydrogen carbonate solution and brine. The solvent was evaporated under reduced pressure, and the residue was purified by NH-silica gel chromatography (developing solvent; ethyl acetate), and then silica gel chromatography (developing solvent; hexane: ethyl acetate=1:1 (volume ratio)→ethyl acetate:methanol=9:1 (volume ratio)) to give the title compound (364 mg, 1.13 mmol) as a colorless liquid.

$^1$H-NMR (CDCl$_3$) δ: 1.44 (s, 9H), 1.93-2.28 (m, 2H), 2.40-2.51 (m, 1H), 2.64-2.92 (m, 5H), 3.37 (q, J=6.5 Hz, 2H), 3.60 (d, J=13.0 Hz, 1H), 3.66 (d, J=13.0 Hz, 1H), 4.53 (s, 1H), 5.04-5.29 (m, 1H), 7.12-7.17 (m, 2H), 7.24-7.29 (m, 2H).

Reference Example 14 tert-butyl 1-[4-(ethoxycarbonyl)phenyl]hydrazinecarboxylate

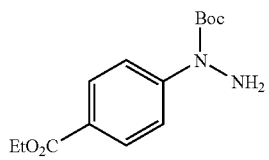

Ethyl 4-bromobenzoate (25.0 g), tert-butyl hydrazinecarboxylate (28.8 g), tris(dibenzylideneacetone)dipalladium(0) (1.00 g), 1,1'-bis(diphenylphosphino)ferrocene (1.82 g) and cesium carbonate (35.6 g) were added to toluene (220 ml) under an argon atmosphere, and the mixture was stirred at 100° C. for 18 hr. The reaction mixture was filtered through celite, and the residue was washed with dichloromethane. The filtrate was concentrated under reduced pressure and the residue was purified by silica gel column chromatography (hexane:ethyl acetate=4:1, volume ratio) to give the title compound (29.9 g). A part of the compound was recrystallized from ethyl acetate-diisopropyl ether to give a colorless crystal.
melting point 74° C.
$^1$H-NMR (300 MHz, CDCl$_3$) δ: 1.39 (3H, t, J=7.1 Hz), 1.53 (9H, s), 4.36 (2H, q, J=7.2 Hz), 4.42 (2H, s), 7.63 (2H, d, J=58.9 Hz), 7.98 (2H, d, J=9.0 Hz).
Elemental analysis (C$_{14}$H$_{20}$N$_2$O$_4$)
Calcd.: C, 59.99; H, 7.19; N, 9.99.
Found: C, 60.03; H, 7.31; N, 9.96.

Reference Example 15 tert-butyl 2-acetyl-1-[4-(ethoxycarbonyl)phenyl]hydrazinecarboxylate

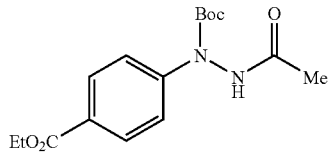

tert-Butyl 1-[4-(ethoxycarbonyl)phenyl]hydrazinecarboxylate (5.60 g) and acetic anhydride (10 ml) were mixed, and the mixture was stirred at 90° C. for 1 hr. The reaction mixture was neutralized with 1N aqueous sodium hydroxide solution, and washed with water and saturated brine. The organic layer was dried over sodium sulfate, and the solvent was evaporated under reduced pressure. The residue was purified by silica gel column chromatography (hexane:ethyl acetate=19:1 (volume ratio)→1:1 (volume ratio)), and further recrystallized from ethyl acetate-hexane to give the title compound (4.42 g) as colorless crystals.
melting point 105-108° C.
$^1$H-NMR (300 MHz, CDCl$_3$) δ ppm rotamer 4:1, 1.38 (2.4H, t, J=7.2 Hz), 1.39 (0.6H, t, J=7.1 Hz), 1.50 (7.2H, s), 1.55 (1.8H, s), 1.96 (0.6H, s), 2.10 (2.4H, s), 4.36 (1.6H, q, J=7.1 Hz), 4.38 (0.4H, q, J=7.1 Hz), 7.32 (0.2H, s), 7.45 (1.6H, d, J=8.9 Hz), 7.56 (0.4H, d, J=8.9 Hz), 7.59 (0.8H, s), 7.98 (1.6H, d, J=8.9 Hz), 8.04 (0.4H, d, J=8.9 Hz).

Elemental analysis ($C_{16}H_{22}N_2O_5$)
Calcd.: C, 59.61; H, 6.88; N, 8.69.
Found: C, 59.55; H, 6.82; N, 8.64.

Reference Example 16 tert-butyl 2-acetyl-1-[4-(ethoxycarbonyl)phenyl]-2-methylhydrazinecarboxylate

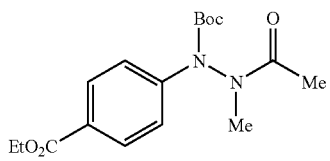

tert-Butyl 2-acetyl-1-[4-(ethoxycarbonyl)phenyl]hydrazinecarboxylate (606 mg) was dissolved in DMF (10 ml), and methyl iodide (0.14 ml) and then sodium hydride (60%, 83 mg) were added at 0° C. The mixture was stirred at room temperature for 3 hr. The reaction mixture was diluted with ethyl acetate, and washed with water and then saturated brine. The organic layer was dried over sodium sulfate, and the solvent was evaporated under reduced pressure. The residue was purified by silica gel column chromatography (hexane:ethyl acetate=19:1 (volume ratio)→1:1 (volume ratio)), and further recrystallized from ethyl acetate-hexane to give the title compound (608 mg) as colorless crystals.

melting point 82° C.
$^1$H-NMR (300 MHz, CDCl$_3$) δ: 1.40 (3H, t, J=7.2 Hz), 1.56 (9H, s), 1.99 (3H, s), 3.16 (3H, s), 4.38 (2H, q, J=7.2 Hz), 7.54 (2H, d, J=9.0 Hz), 8.04 (2H, d, J=9.0 Hz).

Elemental analysis ($C_{17}H_{24}N_2O_5$)
Calcd.: C, 60.70; H, 7.19; N, 8.33.
Found: C, 60.73; H, 7.29; N, 8.35.

Reference Example 17 tert-butyl 2-acetyl-1-[4-(hydroxymethyl)phenyl]-2-methylhydrazinecarboxylate

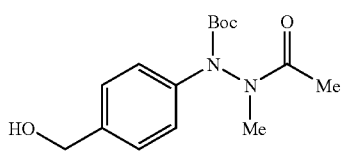

tert-Butyl 2-acetyl-1-[4-(ethoxycarbonyl)phenyl]-2-methylhydrazinecarboxylate (2.06 g) was dissolved in THF (60 ml), lithium borohydride (90%, 0.74 g) was added, and ethanol (15 ml) was slowly added dropwise. The obtained mixture was stirred at 80° C. for 3 hr. Acetone (6.0 ml) was added to the reaction mixture, and the mixture was concentrated under reduced pressure. Ethyl acetate was added to the residue, and the mixture was washed with water and then saturated brine. The organic layer was dried over sodium sulfate, and the solvent was evaporated under reduced pressure. The residue was purified by silica gel column chromatography (hexane: ethyl acetate=9:1 (volume ratio)→1:2 (volume ratio)), and further recrystallized from ethyl acetate to give the title compound (1.22 g) as colorless crystals.

melting point 122-123° C.
$^1$H-NMR (300 MHz, CDCl$_3$) δ ppm 1.54 (9H, s), 1.68 (1H, t, J=5.8 Hz), 2.04 (3H, s), 3.15 (3H, s), 4.69 (2H, d, J=6.0 Hz), 7.37 (2H, d, J=8.7 Hz), 7.43 (2H, d, J=9.0 Hz).

Elemental analysis ($C_{15}H_{22}N_2O_4$)
Calcd.: C, 61.21; H, 7.53; N, 9.52.
Found: C, 61.22; H, 7.64; N, 9.54.

Reference Example 18 tert-butyl 2-acetyl-1-[4-(cyanomethyl)phenyl]-2-methylhydrazinecarboxylate

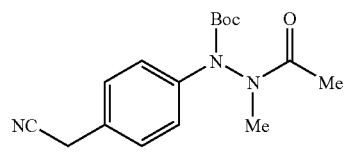

tert-Butyl 2-acetyl-1-[4-(hydroxymethyl)phenyl]-2-methylhydrazinecarboxylate (1.27 g), acetone cyanohydrin (550 mg) and 1,1'-(azodicarbonyl)dipiperidine (1.63 g) were dissolved in THF (60 ml), and tributylphosphine (1.31 g) was added at 0° C. The obtained mixture was stirred at room temperature for 18 hr, and concentrated under reduced pressure. Ethyl acetate was added to the residue, and the mixture was washed with water and then saturated brine. The organic layer was dried over sodium sulfate, and the solvent was evaporated under reduced pressure. The residue was purified by silica gel column chromatography (hexane:ethyl acetate=9:1 (volume ratio)→1:1 (volume ratio)), and further recrystallized from ethyl acetate-hexane to give the title compound (910 mg) as colorless crystals.

melting point 74-75° C.
$^1$H-NMR (300 MHz, CDCl$_3$) δ: 1.55 (9H, s), 2.02 (3H, s), 3.15 (3H, s), 3.74 (2H, s), 7.33 (2H, d, J=8.9 Hz), 7.47 (2H, d, J=8.7 Hz).

Elemental analysis ($C_{16}H_{21}N_3O_3$)
Calcd.: C, 63.35; H, 6.98; N, 13.85.
Found: C, 63.06; H, 7.04; N, 13.81.

Reference Example 19 tert-butyl{2-[4-(hydroxymethyl)phenyl]ethyl}carbamate

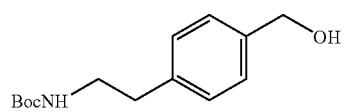

To a solution of ethyl 4-{2-[(tert-butoxycarbonyl)amino]ethyl}benzoate (4 g) in tetrahydrofuran (30 ml) was added lithium aluminum hydride (0.82 g), and the mixture was stirred at 0° C. for 30 min. Water (3.6 ml) and 1N aqueous sodium hydroxide solution (1 ml) were added to quench the reaction, and the precipitate was filtered off. The filtrate was dried over anhydrous sodium sulfate, and concentrated under reduced pressure to give the title compound (3.8 g) as a colorless oil.

IR vhd max (KBr) cm$^{-1}$: 3500-3200 (br, OH), 1693 (C=O).

$^1$H-NMR (300 MHz, CDCl$_3$) δ: 1.434 (9H, s), 2.794 (2H, t, J=7.2 Hz), 3.370 (2H, t, J=7.2 Hz), 4.46-4.56 (1H, br), 4.672 (2H, d, J=4.5 Hz), 7.189 (2H, d, J=8.4 Hz), 7.311 (2H, d, J=8.4 Hz).

Reference Example 20 tert-butyl{2-[4-(bromomethyl)phenyl]ethyl}carbamate

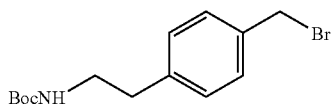

To a solution of the compound (3.8 g) obtained in Reference Example 19 and triphenylphosphine (5.3 g) in acetonitrile (25 ml) was added a solution of carbon tetrabromide (4.2 g) in acetonitrile (12 ml) and the mixture was stirred overnight at room temperature. The mixture was concentrated under reduced pressure and the residue was purified by column chromatography [developing solvent:ethyl acetate-hexane (1:5, volume ratio)] to give the title compound (2.1 g) as a colorless powder.

melting point 88-89° C.

$^1$H-NMR (300 MHz, CDCl$_3$) δ: 1.433 (9H, s), 2.789 (2H, t, J=7.0 Hz), 3.376 (2H, q, J=7.0 Hz), 4.488 (2H, s), 4.50-4.66 (1H, br), 7.168 (2H, d, J=8.1 Hz), 7.333 (2H, d, J=8.1 Hz).

Reference Example 21

1-[4-(2-aminoethyl)benzyl]piperidin-2-one hydrochloride

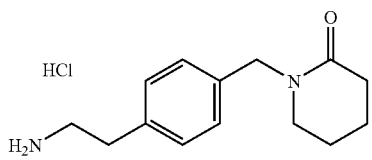

The compound (0.5 g) obtained in Reference Example 20, piperidone (0.17 g), sodium hydride (46 mg) and N,N-dimethylformamide (5 ml) were stirred at room temperature for 1 hr. The reaction mixture was diluted with ethyl acetate (100 ml), washed with 5% aqueous potassium hydrogen sulfate solution, saturated aqueous sodium hydrogen carbonate solution and saturated brine, dried over anhydrous sodium sulfate, and concentrated under reduced pressure. 4N Hydrogen chloride-ethyl acetate solution (10 ml) was added to the residue and the solvent was evaporated under reduced pressure. The residue was washed with tetrahydrofuran to give the title compound (0.36 g) as a colorless powder.

melting point 220-229° C.

Elemental analysis (C$_{14}$H$_{21}$ClN$_2$O.0.9H$_2$O)

Calcd.: C, 59.00; H, 8.06; N, 9.83.

Found: C, 59.06; H, 7.72; N, 9.57.

Reference Example 22 tert-butyl[2-(4-{[(4R)-4-hydroxy-2-oxopyrrolidin-1-yl]methyl}phenyl)ethyl]carbamate

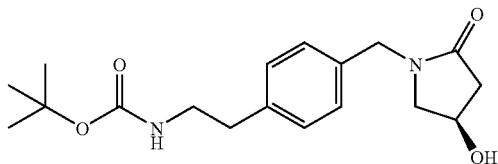

The compound (0.2 g) obtained in Reference Example 20, (4R)-4-hydroxypyrrolidin-2-one (70 mg), sodium hydride (19 mg) and N,N-dimethylformamide (2 ml) were stirred at room temperature for 1 hr. The reaction mixture was diluted with ethyl acetate (100 ml), washed with 5% aqueous potassium hydrogen sulfate solution, saturated aqueous sodium hydrogen carbonate solution and saturated brine, dried over anhydrous sodium sulfate, and concentrated under reduced pressure. The residue was purified by column chromatography [developing solvent:ethyl acetate-methanol (20:1, volume ratio)] to give the title compound (90 mg) as a colorless oil.

IR $v_{max}$ (KBr) cm$^{-1}$: 3500-3200 (br, OH, NH), 1685 (C=O).

$^1$H-NMR (300 MHz, CDCl$_3$) δ: 1.434 (9H, s), 2.445 (1H, dd, J=2.4, 17.4 Hz), 2.757 (1H, dd, J=6.6, 17.4 Hz), 2.774 (2H, t, J=6.6 Hz), 3.194 (1H, dd, J=2.1, 10.8 Hz), 3.32-3.38 (2H, m), 3.521 (1H, dd, J=5.7, 10.8 Hz), 4.428 (1H, d, J=14.4 Hz), 4.486 (1H, d, J=14.4 Hz), 4.48-4.55 (1H, m), 7.14-7.20 (4H, m).

Reference Example 23

(4R)-1-[4-(2-aminoethyl)benzyl]-4-hydroxypyrrolidin-2-one hydrochloride

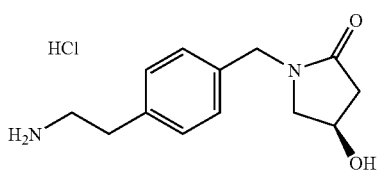

To the compound (90 mg) obtained in Reference Example 22 was added 4N hydrogen chloride-ethyl acetate solution (3 ml), and the mixture was stirred at room temperature for 1 hr. The solvent was evaporated under reduced pressure, and the residue was washed with ethyl acetate to give the title compound (55 mg) as a colorless powder.

melting point 215-217° C.

Elemental analysis (C$_{13}$H$_{19}$ClN$_2$O$_2$.0.3H$_2$O)

Calcd.: C, 56.54; H, 7.15; N, 10.14.

Found: C, 56.28; H, 7.05; N, 10.06.

Reference Example 24

1-[4-(2-aminoethyl)benzyl]-4-ethylpiperazine-2,3-dione hydrochloride

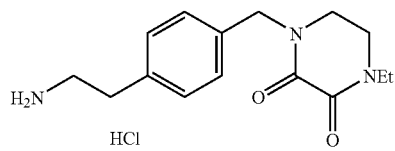

The compound (0.15 g) obtained in Reference Example 20, 1-ethylpiperazine-2,3-dione (75 mg), sodium hydride (14 mg) and N,N-dimethylformamide (1 ml) were stirred at room temperature for 1 hr. The reaction mixture was diluted with ethyl acetate (100 ml), washed with 5% aqueous potassium hydrogen sulfate solution, saturated aqueous sodium hydrogen carbonate solution and saturated brine, dried over anhydrous is sodium sulfate, and concentrated under reduced pressure. 4N Hydrogen chloride-ethyl acetate solution (10 ml) was added to the residue, and the mixture was stirred at room temperature for 1 hr. The solvent was evaporated under reduced pressure, and the residue was washed with ethyl acetate to give the title compound (72 mg) as a colorless powder.

melting point 264-271° C.
Elemental analysis ($C_{15}H_{22}ClN_3O_2 \cdot 0.1H_2O$)
Calcd.: C, 57.45; H, 7.13; N, 13.40.
Found: C, 57.19; H, 7.03; N, 13.40.

Reference Example 25

4-[4-(2-aminoethyl)benzyl]piperazin-2-one dihydrochloride

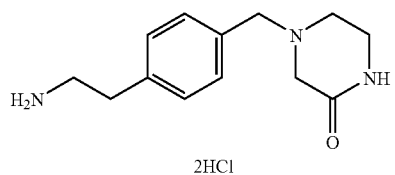

The compound (0.15 g) obtained in Reference Example 20, piperazin-2-one (57 mg), triethylamine (72 mg) and N,N-dimethylformamide (1 ml) were stirred at room temperature for 1 hr. The reaction mixture was diluted with ethyl acetate (100 ml), washed with 5% aqueous potassium hydrogen sulfate solution, saturated aqueous sodium hydrogen carbonate solution and saturated brine, dried over anhydrous sodium sulfate, and concentrated under reduced pressure. 4N Hydrogen chloride-ethyl acetate solution (5 ml) was added to the residue, and the mixture was stirred at room temperature for 2 hr. The solvent was evaporated under reduced pressure, and the residue was washed with ethyl acetate to give the title compound (77 mg) as a colorless powder.

melting point 237-243° C.
Elemental analysis ($C_{13}H_{21}Cl_2N_3O \cdot 1.2H_2O$)
Calcd.: C, 47.63; H, 7.19; N, 12.82.
Found: C, 47.53; H, 7.23; N, 12.75.

Reference Example 26

N-{1-[4-(2-aminoethyl)benzyl]pyrrolidin-3-yl}acetamide dihydrochloride

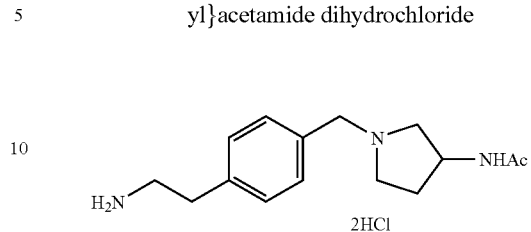

The compound (0.15 g) obtained in Reference Example 20, N-(1-pyrrolidin-3-yl)acetamide (73 mg), triethylamine (72 mg) and N,N-dimethylformamide (3 ml) were stirred overnight at room temperature. The reaction mixture was diluted with ethyl acetate (100 ml), washed with 5% aqueous potassium hydrogen sulfate solution, saturated aqueous sodium hydrogen carbonate solution and saturated brine, dried over anhydrous sodium sulfate, and concentrated under reduced pressure. 4N Hydrogen chloride-ethyl acetate solution (5 ml) was added to the residue, and the mixture was stirred at room temperature for 2 hr. The solvent was evaporated under reduced pressure, and the residue was washed with ethyl acetate to give the title compound (0.16 g) as a colorless amorphous solid.

$^1$H-NMR (300 MHz, $CD_3OD$) δ: 1.932 (3H, s), 1.97-2.02 (2H, m), 2.98-3.03 (2H, m), 3.17-3.22 (2H, m), 3.50-3.60 (1H, m), 3.70-3.78 (1H, m), 4.42-4.46 (3H, m), 4.814 (2H, s), 7.39-7.57 (4H, m).

Reference Example 27 benzyl{2-[4-(bromomethyl)phenyl]ethyl}carbamate

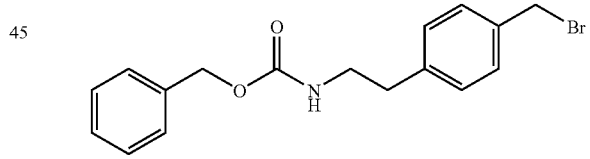

A solution of benzyl {2-[4-(hydroxymethyl)phenyl]ethyl}carbamate (1 g), triphenylphosphine (0.97 g) and carbon tetrabromide (1.2 g) in acetonitrile (1 ml) was stirred overnight at room temperature. The reaction mixture was diluted with ethyl acetate, washed with water and saturated brine, dried over magnesium sulfate, and concentrated under reduced pressure. The residue was purified by column chromatography [developing solvent:ethyl acetate-hexane (1:5, volume ratio)] and crystallized from hexane to give the title compound (0.96 g) as a colorless powder.

melting point 107-109° C.

$^1$H-NMR (300 MHz, $CDCl_3$) δ: 2.812 (2H, t, J=6.6 Hz), 3.450 (2H, q, J=6.6 Hz), 4.478 (2H, s), 4.72-4.78 (1H, br), 5.093 (2H, s), 7.151 (2H, d, J=7.5 Hz), 7.31-7.36 (7H, m).

Reference Example 28 tert-butyl 4-[4-(2-{[(benzyloxy)carbonyl]amino}ethyl)benzyl]-3-oxopiperazine-1-carboxylate

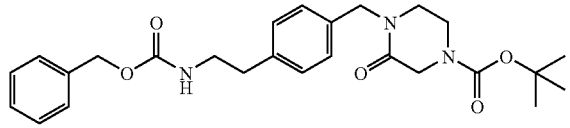

The compound (0.3 g) obtained in Reference Example 27, tert-butyl 3-oxopiperazine-1-carboxylate (0.19 g), sodium hydride (25 mg) and N,N-dimethylformamide (3 ml) were stirred at room temperature for 1 hr. The reaction mixture was diluted with ethyl acetate (50 ml), washed with 5% aqueous potassium hydrogen sulfate solution, saturated aqueous sodium hydrogen carbonate solution and saturated brine, dried over anhydrous sodium sulfate, and concentrated under reduced pressure. The residue was purified by column chromatography [developing solvent:ethyl acetate-hexane (1:1, volume, ratio)] to give the title compound (0.25 g) as a colorless oil.

IR $\nu_{max}$ (KBr) cm$^{-1}$: 3335 (br, NH), 1703, 1651 (C=O).

$^1$H-NMR (300 MHz, CD$_3$OD) δ: 1.461 (9H, s), 2.805 (2H, t, J=7.2 Hz), 3.247 (2H, t, J=5.4 Hz), 3.450 (2H, q, J=7.2 Hz), 3.581 (2H, t, J=5.4 Hz), 4.149 (2H, s), 4.583 (2H, s), 4.72-4.78 (1H, br), 5.093 (2H, s), 7.144 (2H, d, J=8.4 Hz), 7.192 (2H, d, J=8.4 Hz), 7.34-7.36 (5H, m).

Reference Example 29 tert-butyl 4-[4-(2-aminoethyl)benzyl]-3-oxopiperazine-1-carboxylate

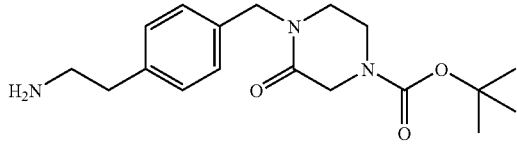

The compound (0.25 g) obtained in Reference Example 28, 10% palladium carbon (0.1 g) and ethanol (10 ml) were stirred under a hydrogen atmosphere at room temperature for 3 hr. The catalyst was filtered off, and the filtrate was concentrated under reduced pressure to give the title compound (0.14 g) as a colorless oil.

IR $\nu_{max}$ (KBr) cm$^{-1}$: 2976, 2930 (NH$_2$), 1697, 1651 (C=O).

$^1$H-NMR (300 MHz, CDCl$_3$) δ: 1.462 (9H, s), 2.760 (2H, t, J=6.6 Hz), 2.95-3.00 (2H, m), 3.254 (2H, t, J=5.6 Hz), 3.585 (2H, t, J=5.6 Hz), 4.150 (2H, s), 4.591 (2H, s), 7.165 (2H, d, J=8.4 Hz), 7.201 (2H, d, J=8.4 Hz).

Example 1

6-(4-chlorophenyl)-3-{2-[4-(pyrrolidin-1-ylmethyl)phenyl]ethyl}thieno[3,2-d]pyrimidin-4(3H)-one

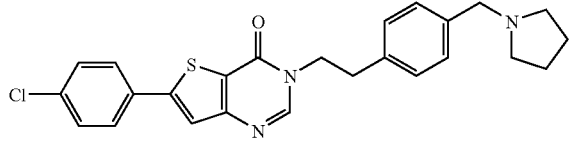

A mixture of methyl 5-(4-chlorophenyl)-3-(dimethylaminomethyleneamino)thiophene-2-carboxylate (0.2 g), 2-[4-(pyrrolidin-1-ylmethyl)phenyl]ethanamine dihydrochloride (0.17 g), N,N-diisopropylethylamine (0.20 g) and ethanol (4 ml) was heated under reflux overnight. The reaction mixture was allowed to cool, ethyl acetate was added, and the precipitate was collected by filtration to give the title compound (168 mg) as a colorless powder.

melting point 163-166° C.

Elemental analysis (C$_{25}$H$_{24}$ClN$_3$OS.0.1H$_2$O)

Calcd.: C, 66.46; H, 5.40; N, 9.30.

Found: C, 66.20; H, 5.30; N, 9.21.

Example 2

6-(4-chlorophenyl)-3-{2-[4-(1-piperidin-1-ylethyl)phenyl]ethyl}thieno[3,2-d]pyrimidin-4(3H)-one

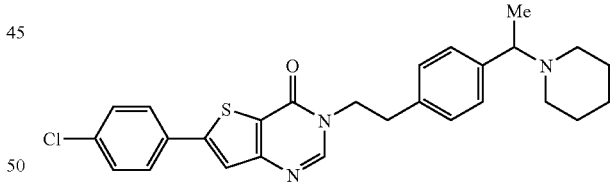

A mixture of methyl 5-(4-chlorophenyl)-3-(dimethylaminomethyleneamino)thiophene-2-carboxylate (0.2 g), 2-[4-(1-piperidin-1-ylethyl)phenyl]ethanamine dihydrochloride (0.19 g), N,N-diisopropylethylamine (0.20 g) and ethanol (4 ml) were stirred at 70° C. for 3 hr. The reaction mixture was allowed to cool, ethyl acetate was added, and the precipitate was collected by filtration to give the title compound (186 mg) as a colorless powder.

melting point 175-179° C.

Elemental analysis (C$_{27}$H$_{28}$ClN$_3$OS.0.1H$_2$O)

Calcd.: C, 67.58; H, 5.92; N, 8.76.

Found: C, 67.30; H, 5.71; N, 8.53.

Example 3 tert-butyl N-(4-{2-[6-(4-chlorophenyl)-4-oxothieno[3,2-d]pyrimidin-3(4H)-yl]ethyl}benzyl)-N-methyl-carbamate

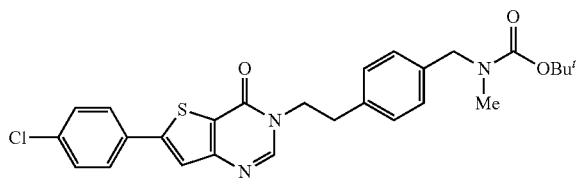

A mixture of methyl 5-(4-chlorophenyl)-3-(dimethylaminomethyleneamino)thiophene-2-carboxylate (0.2 g), 2-[4-(N-tert-butyloxycarbonyl-N-methylaminomethyl)phenyl]ethanamine (0.19 g) and ethanol (4 ml) were stirred at 70° C. for 3 hr. The reaction mixture was allowed to cool, ethyl acetate was added, and the precipitate was collected by filtration to give the title compound (160 mg) as a colorless powder.
melting point 206-209° C.
Elemental analysis ($C_{27}H_{28}ClN_3O_3S$)
Calcd.: C, 63.58; H, 5.53; N, 8.24.
Found: C, 63.57; H, 5.50; N, 8.20.

Example 4

6-(4-chlorophenyl)-3-(2-{4-[(methylamino)methyl]phenyl}ethyl)thieno[3,2-d]pyrimidin-4(3H)-one dihydrochloride

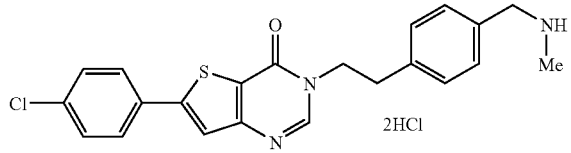

A mixture of the compound (0.18 g) obtained in Example 3 and 4N hydrogen chloride-ethyl acetate solution was stirred at room temperature for 1 hr. The solvent was evaporated under reduced pressure, and the residue was washed with ethyl acetate to give the title compound (0.17 g) as a colorless powder.
melting point >300° C.
Elemental analysis ($C_{22}H_{22}Cl_3N_3OS \cdot 0.1H_2O$)
Calcd.: C, 54.52; H, 4.62; N, 8.67.
Found: C, 54.28; H, 4.66; N, 8.47.

Example 5

N-(4-{2-[6-(4-chlorophenyl)-4-oxothieno[3,2-d]pyrimidin-3(4H)-yl]ethyl}benzyl)-N,3,3-trimethylbutanamide

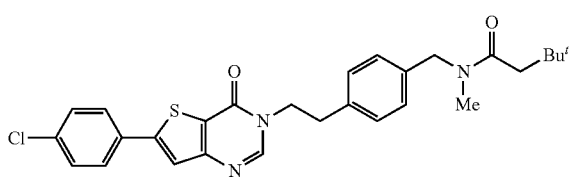

A mixture of the compound (85 mg) obtained in Example 4, 3,3-dimethylbutanoyl chloride (31 mg), triethylamine (53 mg) and tetrahydrofuran (2 ml) was stirred at 60° C. for 3 hr. The reaction mixture was diluted with ethyl acetate, and washed with water and saturated brine, dried over anhydrous sodium sulfate, and concentrated under reduced pressure. The residue was recrystallized from ethyl acetate-hexane (2:1, volume ratio) to give the title compound (70 mg) as a colorless powder.
melting point 181° C.
Elemental analysis ($C_{28}H_{30}ClN_3O_2S \cdot 0.1H_2O$)
Calcd.: C, 65.96; H, 5.97; N, 8.24.
Found: C, 65.67; H, 5.93; N, 8.26.

Example 6

N-(4-{2-[6-(4-chlorophenyl)-4-oxothieno[3,2-d]pyrimidin-3(4H)-yl]ethyl}benzyl)-N-methylacetamide

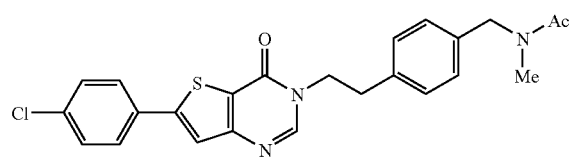

A mixture of the compound (85 mg) obtained in Example 4, acetyl chloride (18 mg), triethylamine (53 mg) and tetrahydrofuran (2 ml) was stirred at 60° C. for 3 hr. The reaction mixture was diluted with ethyl acetate, washed with water and saturated brine, dried over anhydrous sodium sulfate, and concentrated under reduced pressure. The residue was recrystallized from ethyl acetate-hexane (2:1, volume ratio) to give the title compound (60 mg) as a colorless powder.
melting point 176-178° C.
Elemental analysis ($C_{24}H_{22}ClN_3O_2S$)
Calcd.: C, 63.78; H, 4.91; N, 9.30.
Found: C, 63.38; H, 4.91; N, 9.21.

Example 7

N-(4-{2-[6-(4-chlorophenyl)-4-oxothieno[3,2-d]pyrimidin-3(4H)-yl]ethyl}benzyl)-N-methylcyclopropanecarboxamide

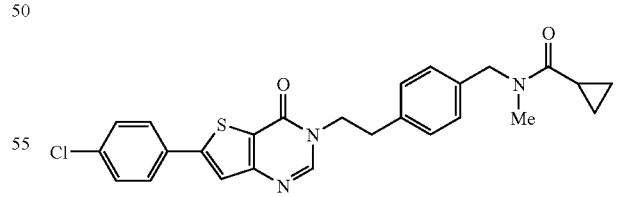

A mixture of the compound (0.1 g) obtained in Example 4, cyclopropylcarbonyl chloride (25 mg), triethylamine (76 mg) and tetrahydrofuran (2 ml) was stirred at 60° C. for 3 hr. The reaction mixture was diluted with ethyl acetate, washed with water and saturated brine, dried over anhydrous sodium sulfate, and concentrated under reduced pressure. The residue was recrystallized from ethyl acetate-hexane (1:1, volume ratio) to give the title compound (67 mg) as a colorless powder.

melting point 178° C.
Elemental analysis ($C_{26}H_{24}ClN_3O_2S$)
Calcd.: C, 65.33; H, 5.06; N, 8.79.
Found: C, 65.22; H, 5.00; N, 8.85.

Example 8

N-(4-{2-[6-(4-chlorophenyl)-4-oxothieno[3,2-d]pyrimidin-3(4H)-yl]ethyl}benzyl)-N,N',N'-trimethylurea

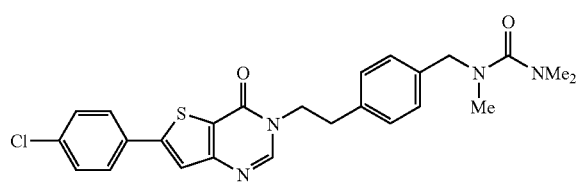

A mixture of the compound (0.1 g) obtained in Example 4, dimethylcarbamoyl chloride (25 mg), triethylamine (76 mg) and tetrahydrofuran (2 ml) was stirred at 60° C. for 3 hr. The reaction mixture was diluted with ethyl acetate, washed with water and saturated brine, dried over anhydrous sodium sulfate, and concentrated under reduced pressure. The residue was recrystallized from ethyl acetate-hexane (1:1, volume ratio) to give the title compound (70 mg) as a colorless powder.

melting point 160-165° C.
Elemental analysis ($C_{25}H_{25}ClN_4O_2S$)
Calcd.: C, 62.42; H, 5.24; N, 11.65.
Found: C, 62.15; H, 5.33; N, 11.68.

Example 9

N-(4-{2-[6-(4-chlorophenyl)-4-oxothieno[3,2-d]pyrimidin-3(4H)-yl]ethyl}benzyl)-N,N',N'-trimethylthiourea

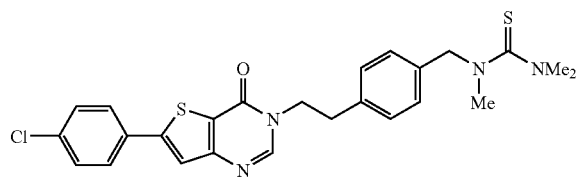

A mixture of the compound (0.1 g) obtained in Example 4, dimethylcarbamothioyl chloride (25 mg), triethylamine (76 mg) and N,N-dimethylformamide (2 ml) was stirred at 60° C. for 3 hr. The reaction mixture was diluted with ethyl acetate, 5% aqueous potassium hydrogen sulfate solution, washed with saturated aqueous sodium hydrogen carbonate solution and saturated brine, dried over anhydrous sodium sulfate, and is concentrated under reduced pressure. The residue was purified by column chromatography [developing solvent:ethyl acetate-hexane (3:1, volume ratio)], and recrystallized from ethyl acetate-hexane (1:1, volume ratio) to give the title compound (40 mg) as a colorless powder.

melting point 156-158° C.
Elemental analysis ($C_{25}H_{25}ClN_4OS_2 \cdot 0.1H_2O$)
Calcd.: C, 60.19; H, 5.09; N, 11.23.
Found: C, 59.89; H, 4.89; N, 11.14.

Example 10

6-(4-chlorophenyl)-3-{2-oxo-2-[3-(trifluoroacetyl)-2,3,4,5-tetrahydro-1H-3-benzazepin-7-yl]ethyl}thieno[3,2-d]pyrimidin-4(3H)-one

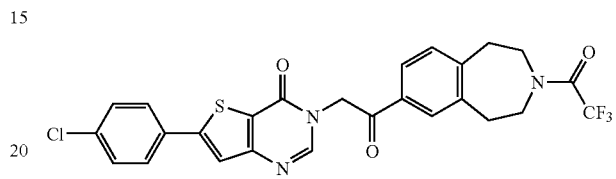

A mixture of methyl 5-(4-chlorophenyl)-3-(dimethylaminomethyleneamino)thiophene-2-carboxylate (0.3 g), the compound (0.34 g) obtained in Reference Example 3, N,N-diisopropylethylamine (126 mg) and ethanol (6 ml) was stirred overnight at 70° C. The reaction mixture was allowed to cool, ethyl acetate was added, and the precipitate was collected by filtration to give the title compound (100 mg) as a colorless powder.

melting point 285-287° C.
Elemental analysis ($C_{26}H_{19}ClF_3N_3O_3S$)
Calcd.: C, 57.20; H, 3.51; N, 7.70.
Found: C, 57.23; H, 3.57; N, 7.51.

Example 11

6-(4-chlorophenyl)-3-(2-{4-[(2-oxopyrrolidin-1-yl)methyl]phenyl}ethyl)thieno[3,2-d]pyrimidin-4(3H)-one

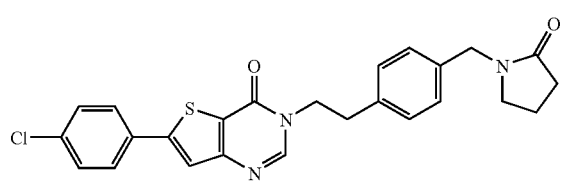

A mixture of methyl 5-(4-chlorophenyl)-3-(dimethylaminomethyleneamino)thiophene-2-carboxylate (0.1 g), 1-[4-(2-aminoethyl)benzyl]pyrrolidin-2-one hydrochloride (87 mg), N,N-diisopropylethylamine (44 mg) and ethanol (2 ml) was stirred at 70° C. for 3 hr. The reaction mixture was allowed to cool, ethyl acetate was added, and the precipitate was collected by filtration to give the title compound (109 mg) as a colorless powder.

melting point 218-221° C.
Elemental analysis ($C_{25}H_{22}ClN_3O_2S \cdot 0.1H_2O$)
Calcd.: C, 64.47; H, 4.80; N, 9.02.
Found: C, 64.31; H, 4.83; N, 8.79.

Example 12

N-(4-{[6-(4-chlorophenyl)-4-oxothieno[3,2-d]pyrimidin-3(4H)-yl]acetyl}benzyl)-2,2,2-trifluoro-N-methylacetamide

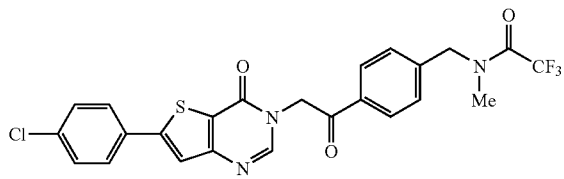

A mixture of methyl 5-(4-chlorophenyl)-3-(dimethylaminomethyleneamino)thiophene-2-carboxylate (0.47 g), the compound (0.5 g) obtained in Reference Example 7, N,N-diisopropylethylamine (198 mg) and ethanol (10 ml) was stirred overnight at 70° C. The reaction mixture was allowed to cool, ethyl acetate was added, and the precipitate was collected by filtration to give the title compound (0.54 g) as a colorless powder.
melting point 235-238° C.
Elemental analysis ($C_{24}H_{17}ClF_3N_3O_3S$)
Calcd.: C, 55.44; H, 3.30; N, 8.08.
Found: C, 55.39; H, 3.39; N, 8.12.

Example 13

6-(4-chlorophenyl)-3-(2-{4-[(methylamino)methyl]phenyl}-2-oxoethyl)thieno[3,2-d]pyrimidin-4(3H)-one

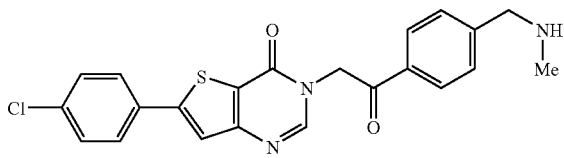

A mixture of the compound (0.49 g) obtained in Example 12, potassium carbonate (0.39 g), water (4 ml), methanol (8 ml) and tetrahydrofuran (8 ml) was stirred at 60° C. for 3 hr. The reaction mixture was diluted with water and extracted with ethyl acetate. The organic layer was washed with saturated brine, dried over magnesium sulfate, and concentrated under reduced pressure. The residue was crystallized from ethyl acetate to give the title compound (79 mg) as a colorless powder.
melting point 259-261° C.
$^1$H-NMR (CDCl$_3$) δ: 2.48 (3H, s), 3.86 (2H, s), 5.48 (2H, s), 7.44 (2H, d, J=8.4 Hz), 7.51 (2H, d, J=8.4 Hz), 7.53 (1H, s), 7.65 (2H, d, J=8.4 Hz), 8.00 (1H, s), 8.03 (2H, d, J=8.4 Hz).

Example 14

N-(4-{[6-(4-chlorophenyl)-4-oxothieno[3,2-d]pyrimidin-3(4H)-yl]acetyl}benzyl)-N-methylacetamide

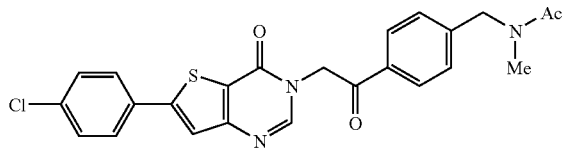

A mixture of the compound (50 mg) obtained in Example 13, acetyl chloride (10 mg), triethylamine (18 mg) and tetrahydrofuran (1 ml) was stirred at room temperature for 30 min. The reaction mixture was diluted with ethyl acetate and water, and the precipitate was collected by filtration to give the title compound (39 mg) as a colorless powder.
melting point 250-251° C.
Elemental analysis ($C_{24}H_{20}ClN_3O_3S \cdot 0.2H_2O$)
Calcd.: C, 61.39; H, 4.38; N, 8.95.
Found: C, 61.23; H, 4.32; N, 8.96.

Example 15

N-(5-{[6-(4-chlorophenyl)-4-oxothieno[3,2-d]pyrimidin-3(4H)-yl]acetyl}-2,3-dihydro-1H-inden-2-yl)-2,2,2-trifluoro-N-methylacetamide

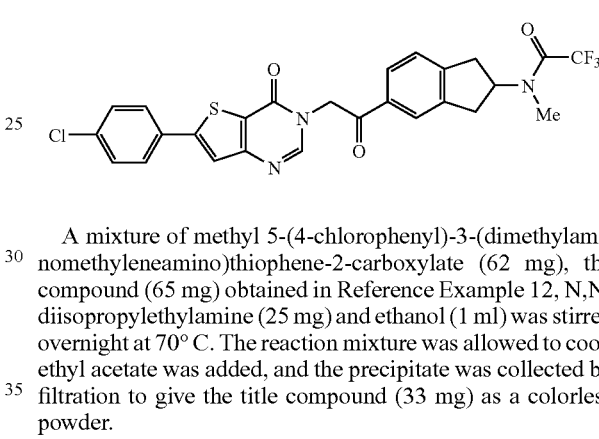

A mixture of methyl 5-(4-chlorophenyl)-3-(dimethylaminomethyleneamino)thiophene-2-carboxylate (62 mg), the compound (65 mg) obtained in Reference Example 12, N,N-diisopropylethylamine (25 mg) and ethanol (1 ml) was stirred overnight at 70° C. The reaction mixture was allowed to cool, ethyl acetate was added, and the precipitate was collected by filtration to give the title compound (33 mg) as a colorless powder.
melting point 245-248° C.
Elemental analysis ($C_{26}H_{19}ClF_3N_3O_3S$)
Calcd.: C, 57.20; H, 3.51; N, 7.70.
Found: C, 56.98; H, 3.44; N, 7.67.

Example 16

6-(4-chlorophenyl)-3-{2-[2-(methylamino)-2,3-dihydro-1H-inden-5-yl]-2-oxoethyl}thieno[3,2-d]pyrimidin-4(3H)-one

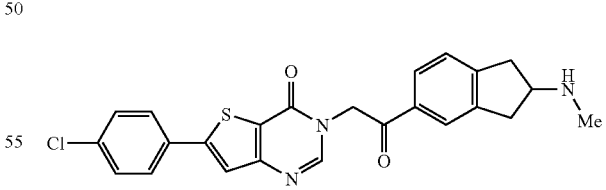

A mixture of the compound (70 mg) obtained in Example 15, potassium carbonate (53 mg), water (0.5 ml), methanol (1 ml) and tetrahydrofuran (1 ml) was stirred at 60° C. for 3 hr. The reaction mixture was diluted with water, and extracted with ethyl acetate. The organic layer was washed with saturated brine, dried over magnesium sulfate, and concentrated under reduced pressure. The residue was crystallized from ethyl acetate to give the title compound (60 mg) as a colorless powder.

melting point 226-229° C.
Elemental analysis ($C_{24}H_{20}ClN_3O_2S \cdot 1.2H_2O$)
Calcd.: C, 61.13; H, 4.79; N, 8.91.
Found: C, 60.78; H, 4.50; N, 8.75.

Example 17

N-(5-{[6-(4-chlorophenyl)-4-oxothieno[3,2-d]pyrimidin-3(4H)-yl]acetyl}-2,3-dihydro-1H-inden-2-yl)-N-methylacetamide

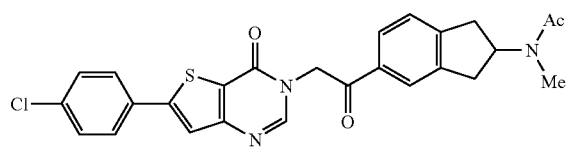

A mixture of the compound (27 mg) obtained in Example 16, acetyl chloride (5.2 mg), triethylamine (9.2 mg) and tetrahydrofuran (1 ml) was stirred at room temperature for 30 min. The reaction mixture was diluted with ethyl acetate and water, and the precipitate was collected by filtration to give the title compound (29 mg) as a colorless powder.
melting point 276° C.
$^1$H-NMR (300 MHz, CDCl$_3$) δ: 2.13 (⅔×3H, s), 2.23 (⅓×3H, s), 2.80 (⅓×3H, s), 2.84 (⅔×3H, s), 2.98 (⅔×2H, dd, J=6.6, 17.1 Hz), 3.13 (⅓×2H, dd, J=6.6, 17.1 Hz), 3.28 (2H, dd, J=8.4, 17.1 Hz), 4.83-4.88 (⅓×1H, m), 5.46 (2H, s), 5.62-5.72 (⅔×1H, m), 7.38 (1H, d, J=7.8 Hz), 7.44 (2H, d, J=8.4 Hz), 7.53 (1H, s), 7.65 (2H, d, J=8.4 Hz), 7.88-7.93 (2H, m), 8.01 (1H, s).

Example 18

6-(4-chlorophenyl)-3-[2-(4-{[(3S)-3-fluoropyrrolidin-1-yl]methyl}phenyl)ethyl]thieno[3,2-d]pyrimidin-4(3H)-one

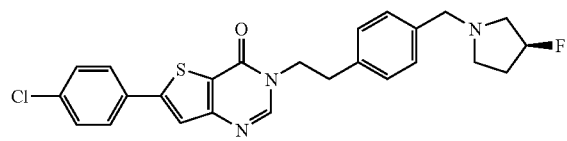

Trifluoroacetic acid (5 ml) was added to the compound (364 mg, 1.13 mmol) obtained in Reference Example 13, and the mixture was stirred at room temperature for 7 hr. The reaction mixture was concentrated under reduced pressure to give a colorless oil. To a solution of the colorless oil in ethanol (30 ml) were added N,N-diisopropylethylamine (983 ml, 5.65 mmol) and methyl 5-(4-chlorophenyl)-3-{[(1E)-(dimethylamino)methylene]amino}thiophene-2-carboxylate (365 mg, 1.13 mmol) and the mixture was stirred at 70° C. for 17 hr. Ethyl acetate was added to the reaction mixture, and the mixture was washed with saturated aqueous sodium hydrogen carbonate solution and saturated brine. The solvent was evaporated under reduced pressure and the residue was purified by silica gel chromatography (developing solvent; ethyl acetate:methanol=10:1 (volume ratio)→9:1 (volume ratio)). The precipitated crystals were washed with isopropyl ether, collected by filtration and dried to give the title compound (111 mg, 0.238 mmol) as colorless crystals.
$^1$H-NMR (CDCl$_3$) δ: 1.93-2.27 (m, 2H), 2.39-2.48 (m, 1H), 2.62-2.90 (m, 3H), 3.11 (t, J=7.0 Hz, 2H), 3.57-3.69 (m, 2H), 4.24 (t, J=7.0 Hz, 2H), 5.04-5.29 (m, 1H), 7.11 (d, J=8.1 Hz, 2H), 7.27 (d, J=7.9 Hz, 2H), 7.40-7.46 (m, 3H), 7.61-7.66 (m, 3H).

Example 19

6-(4-chlorophenyl)-3-[2-[4-[1-[(3S)-3-fluoropyrrolidin-1-yl]ethyl]phenyl]ethyl]thieno[3,2-d]pyrimidin-4(3H)-one

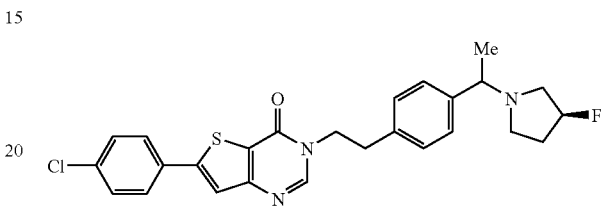

tert-Butyl [2-[4-(1-hydroxyethyl)phenyl]ethyl]carbamate (606 mg) was dissolved in dichloromethane (20 ml), triethylamine (0.38 ml) and then methanesulfonyl chloride (0.195 ml) were added at 0° C., and the mixture was stirred for 4 hr. The reaction mixture was diluted with dichloromethane, and washed with saturated aqueous sodium hydrogen carbonate solution and then saturated brine. The organic layer was dried over sodium sulfate, and the solvent was evaporated under reduced pressure to give 1-[4-[2-[(tert-butoxycarbonyl)amino]ethyl]phenyl]ethyl methanesulfonate. The obtained compound, (3S)-3-fluoropyrrolidine hydrochloride (287 mg) and N,N-diisopropylethylamine (1.18 g) were mixed with DMF (10 ml), and the mixture was stirred at 50° C. for 48 hr. The reaction mixture was diluted with ethyl acetate, and washed with water and then saturated brine. The organic layer was dried over sodium sulfate, and the solvent was evaporated under reduced pressure. The residue was purified by silica gel column chromatography (hexane:ethyl acetate=3:1 (volume ratio)→ethyl acetate→ethyl acetate:methanol=9:1 (volume ratio)) to give tert-butyl [2-[4-[1-[(3S)-3-fluoropyrrolidin-1-yl]ethyl]phenyl]ethyl]carbamate (133 mg) as a crude oil.
The crude oil was dissolved in dichloromethane (2.0 ml), and trifluoroacetic acid (2.0 ml) was added. The mixture was stirred at room temperature for 2 hr. The reaction mixture was concentrated under reduced pressure to give 2-[4-[1-[(3S)-3-fluoropyrrolidin-1-yl]ethyl]phenyl]ethylamine ditrifluoroacetate. The obtained compound and methyl 5-(4-chlorophenyl)-3-[[(1E)-(dimethylamino)methylene]amino]thiophene-2-carboxylate (119 mg) were mixed with ethanol (4.0 ml) and N,N-diisopropylethylamine (1.0 ml), and the mixture was stirred at 80° C. for 9 hr. The reaction mixture was concentrated under reduced pressure. The residue was purified by silica gel column chromatography (hexane:ethyl acetate=3:1 (volume ratio)→ethyl acetate), and further recrystallized from ethyl acetate-diisopropyl ether to give the title compound (80.6 mg) as colorless crystals.
melting point 160-163° C.
$^1$H-NMR (300 MHz, CDCl$_3$) δ: 1.41 (3H, br), 2.12 (3H, br), 2.70 (2H, br), 2.84-2.97 (1H, m), 3.11 (2H, t, J=7.0 Hz), 3.28 (1H, br), 4.25 (2H, t, J=7.1 Hz), 5.15 (1H, d, J=56.9 Hz), 7.13 (2H, d, J=7.7 Hz), 7.31 (2H, br), 7.41-7.47 (3H, m), 7.59-7.68 (3H, m).
Elemental analysis ($C_{26}H_{25}ClFN_3OS \cdot 0.5H_2O$)
Calcd.: C, 63.60; H, 5.34; N, 8.56.
Found: C, 63.60; H, 5.26; N, 8.54.

Example 20 tert-butyl 2-acetyl-1-[4-[2-[6-(4-chlorophenyl-4-oxothieno[3,2-d]pyrimidin-3(4H)-yl]ethyl]phenyl]-2-methylhydrazinecarboxylate

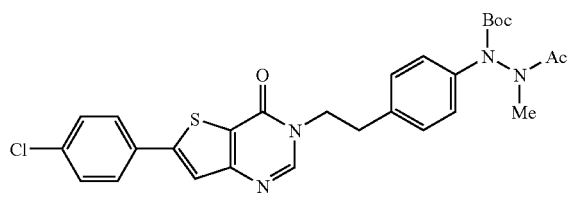

tert-Butyl 2-acetyl-1-[4-(cyanomethyl)phenyl]-2-methylhydrazinecarboxylate (607 mg) and cobalt chloride (520 mg) were dissolved in methanol (20 ml), and sodium borohydride (757 mg) was added by small portions at 0° C. The reaction mixture was stirred at room temperature for 2.5 hr, and diluted with ethyl acetate (200 ml). The obtained diluted solution was passed through basic silica gel (100 g) and washed with ethyl acetate:methanol=10:1 (volume ratio). The filtrate was concentrated under reduced pressure to give tert-butyl 2-acetyl-1-[4-(2-aminoethyl)phenyl]-2-methylhydrazinecarboxylate as a colorless oil.

The colorless oil and methyl 5-(4-chlorophenyl)-3-[[(1E)-(dimethylamino)methylene]amino]thiophene-2-carboxylate (581 mg) were added to ethanol (20 ml), and the mixture was stirred at 80° C. for 10 hr. The precipitated crystals were collected by filtration and dried to give the title compound (305 mg) as colorless crystals. The mother liquor was concentrated under reduced pressure and the residue was purified by silica gel column chromatography (hexane:ethyl acetate=4:1 (volume ratio)→ethyl acetate) to give the title compound (147 mg) as colorless crystals.

melting point 193-194° C.

$^1$H-NMR (300 MHz, CDCl$_3$) δ: 1.54 (9H, s), 2.02 (3H, s), 3.11 (2H, t, J=6.9 Hz), 3.13 (3H, s), 4.24 (2H, t, J=7.0 Hz), 7.16 (2H, d, J=8.7 Hz), 7.38 (2H, d, J=8.7 Hz), 7.44 (2H, d, J=8.7 Hz), 7.44 (1H, s), 7.64 (2H, d, J=8.5 Hz), 7.68 (1H, s).

Elemental analysis (C$_{28}$H$_{29}$ClN$_4$O$_4$S)

Calcd.: C, 60.81; H, 5.29; N, 10.13.
Found: C, 60.62; H, 5.30; N, 10.16.

Example 21

N'-[4-[2-[6-(4-chlorophenyl)-4-oxothieno[3,2-d]pyrimidin-3(4H)-yl]ethyl]phenyl]-N-methylacetohydrazide

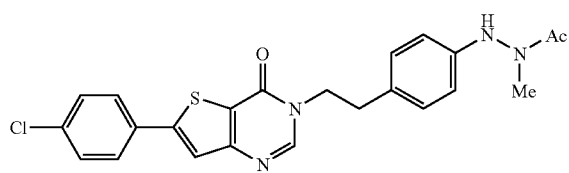

tert-Butyl 2-acetyl-1-[4-[2-[6-(4-chlorophenyl)-4-oxothieno[3,2-d]pyrimidin-3(4H)-yl]ethyl]phenyl]-2-methylhydrazinecarboxylate (356 mg) was dissolved in dichloromethane (6.5 ml), and trifluoroacetic acid (2.0 ml) was added. The reaction mixture was stirred at room temperature for 1.5 hr, and diluted with dichloromethane. The obtained diluted solution was washed with saturated aqueous sodium hydrogen carbonate solution, the organic layer was dried over sodium sulfate, and the solvent was evaporated under reduced pressure. The precipitated crystals were washed with ethyl acetate-diisopropyl ether to give the title compound (287 mg) as colorless crystals.

melting point 267-268° C.

$^1$H-NMR (300 MHz, CDCl$_3$) δ: 2.16 (3H, s), 3.06 (2H, t, J=7.0 Hz), 3.12 (3H, s), 4.22 (2H, t, J=7.0 Hz), 5.65 (1H, s), 6.64 (2H, d, J=8.5 Hz), 7.07 (2H, d, J=8.5 Hz), 7.44 (2H, d, J=8.7 Hz), 7.44 (1H, s), 7.64 (2H, d, J=8.7 Hz), 7.66 (1H, s).

Example 22

N'-[4-[2-[6-(4-chlorophenyl)-4-oxothieno[3,2-d]pyrimidin-3(4H)-yl]ethyl]phenyl]-N,N'-dimethylacetohydrazide

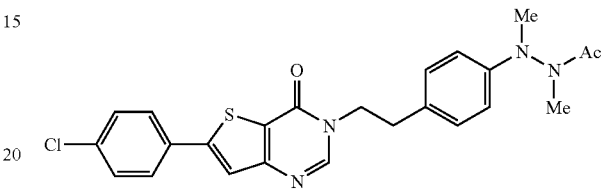

N'-[4-[2-[6-(4-Chlorophenyl)-4-oxothieno[3,2-d]pyrimidin-3(4H)-yl]ethyl]phenyl]-N-methylacetohydrazide (106 mg) was suspended in DMF (7.0 ml), and methyl iodide (17 μl) and then sodium hydride (60%, 10 mg) were added at 0° C. The obtained mixture was stirred at room temperature for 4.5 hr, and methyl iodide (17 μl) and then sodium hydride (60%, 10 mg) were added at 0° C. The obtained mixture was stirred at room temperature for 24 hr, diluted with chloroform, and washed with water and then saturated brine. The organic layer was dried over sodium sulfate, and the solvent was evaporated under reduced pressure. The residue was purified by silica gel column chromatography (chloroform→chloroform:methanol=50:1 (volume ratio)) and further washed with ethyl acetate to give the title compound (50.1 mg) as colorless crystals.

melting point 227-228° C.

$^1$H-NMR (300 MHz, CDCl$_3$) δ: 2.11 (3H, s), 2.95 (3H, s), 3.06 (2H, t, J=6.6 Hz), 3.09 (3H, s), 4.22 (2H, td, J=6.9, 2.1 Hz), 6.63 (2H, d, J=8.7 Hz), 7.08 (2H, d, J=8.7 Hz), 7.41-7.47 (3H, m), 7.61-7.67 (3H, m).

Example 23

6-(4-fluorophenyl)-3-{2-[4-(1-pyrrolidin-1-ylethyl)phenyl]ethyl}thieno[3,2-d]pyrimidine-2,4(1H,3H)-dione

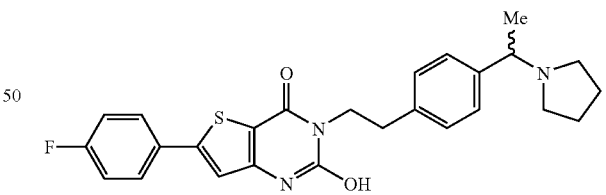

To a mixture of 3-amino-5-(4-fluorophenyl)thiophene-2-carboxylic acid (0.20 g), 2-[4-(1-pyrrolidin-1-ylethyl)phenyl]ethanamine dihydrochloride (0.22 g), 1-hydroxybenzotriazole (0.16 g), N,N-diisopropylethylamine (0.30 ml) and DMF (3.0 ml) was added 1-(3-dimethylaminopropyl)-3-ethylcarbodiimide hydrochloride (0.15 g), and the mixture was stirred overnight at room temperature. The reaction mixture was diluted with ethyl acetate, washed with water and saturated brine, dried over anhydrous sodium sulfate, and concentrated under reduced pressure. The residue was purified by column chromatography (hexane:ethyl acetate=9:1 (volume ratio)→1:2 (volume ratio)) using NH-silica gel to give 3-amino-5-(4-fluorophenyl)-N-{2-[4-(1-pyrrolidin-1-ylethyl)phenyl]ethyl}thiophene-2-carboxamide (0.15 g).

The obtained 3-amino-5-(4-fluorophenyl)-N-{2-[4-(1-pyrrolidin-1-ylethyl)phenyl]ethyl}thiophene-2-carboxamide (0.15 g) was suspended in 1,2-dichloroethane (5 ml), and triethylamine (0.067 ml) and triphosgene (0.080 g) were successively added with stirring. After 3 hr, pyrrolidine (0.8 ml) was added, and the reaction mixture was stirred overnight at room temperature. The reaction mixture was diluted with ethyl acetate, washed with water and saturated brine, dried over anhydrous sodium sulfate, and concentrated under reduced pressure. The residue was purified by column chromatography (hexane:ethyl acetate=9:1 (volume ratio)→1:2 (volume ratio)) using NH-silica gel, and further recrystallized from ethyl acetate to give the title compound (0.024 g) as pale-yellow crystals.

melting point 260-264° C.

$^1$H-NMR (300 MHz, CDCl$_3$) δ ppm 1.45 (br. d, J=4.90 Hz, 3H), 1.79 (br, 4H), 2.45 (br, 2H), 2.62 (br, 2H), 2.92-3.07 (m, 2H), 3.26 (br, 1H), 4.20-4.37 (m, 2H), 7.00 (s, 1H), 7.16 (t, J=8.57 Hz, 2H), 7.22-7.38 (m, 5H), 7.64 (dd, J=8.76, 5.18 Hz, 2H).

Example 24

N-(4-{2-[6-(4-chlorophenyl)-4-oxothieno[3,2-d]pyrimidin-3(4H)-yl]ethyl}benzyl)-N-methyl-methanesulfonamide

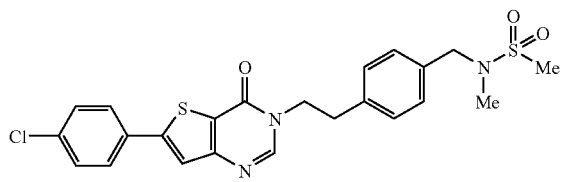

A mixture of the compound (100 mg) obtained in Example 4, methanesulfonyl chloride (30 mg), triethylamine (76 mg) and tetrahydrofuran (2 ml) was stirred at 0° C. for 1 hr. The reaction mixture was diluted with ethyl acetate, and washed with water. The precipitate was collected by filtration to give the title compound (32 mg) as a colorless powder.

melting point 230-232° C.

Elemental analysis (C$_{23}$H$_{22}$ClN$_3$O$_3$S$_2$.0.1H$_2$O)

Calcd.: C, 55.99; H, 4.62; N, 8.52.

Found: C, 55.69; H, 4.62; N, 8.43.

Example 25

6-(4-chlorophenyl)-3-(2-{4-[(2-oxopiperidin-1-yl)methyl]phenyl}ethyl)thieno[3,2-d]pyrimidin-4(3H)-one

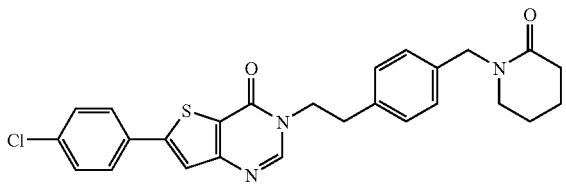

A mixture of methyl 5-(4-chlorophenyl)-3-(dimethylaminomethyleneamino)thiophene-2-carboxylate (0.2 g), the compound (0.17 g) obtained in Reference Example 21, N,N-diisopropylethylamine (88 mg) and ethanol (2 ml) was stirred overnight at 70° C. The reaction mixture was allowed to cool, ethyl acetate was added, and the precipitate was collected by filtration to give the title compound (170 mg) as a colorless powder.

melting point 199-201° C.

Elemental analysis (C$_{26}$H$_{24}$ClN$_3$O$_2$S.0.1H$_2$O)

Calcd.: C, 65.08; H, 5.08; N, 8.76.

Found: C, 64.75; H, 5.36; N, 8.77.

Example 26

6-(4-fluorophenyl)-3-(2-{4-[(2-oxopiperidin-1-yl)methyl]phenyl}ethyl)thieno[3,2-d]pyrimidin-4(3H)-one

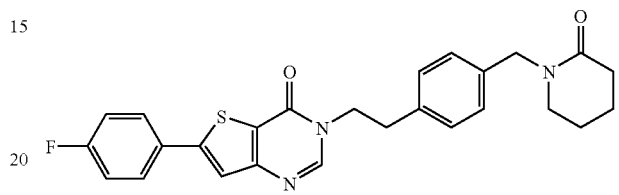

A mixture of methyl 5-(4-fluorophenyl)-3-(dimethylaminomethyleneamino)thiophene-2-carboxylate (0.1 g), the compound (88 mg) obtained in Reference Example 21, N,N-diisopropylethylamine (46 mg) and ethanol (1 ml) was stirred overnight at 70° C. The reaction mixture was allowed to cool, ethyl acetate was added, and the precipitate was collected by filtration to give the title compound (92 mg) as a colorless powder.

melting point 216-217° C.

Elemental analysis (C$_{26}$H$_{24}$FN$_3$O$_2$S.0.2H$_2$O)

Calcd.: C, 67.13; H, 5.29; N, 9.03.

Found: C, 66.99; H, 5.42; N, 9.08.

Example 27

2-chloro-N-(4-{2-[6-(4-chlorophenyl)-4-oxothieno[3,2-d]pyrimidin-3(4H)-yl]ethyl}benzyl)-N-methylacetamide

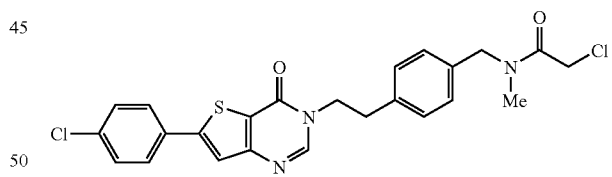

A mixture of the compound (200 mg) obtained in Example 4, chloroacetyl chloride (51 mg), triethylamine (146 mg) and tetrahydrofuran (2 ml) was stirred at 60° C. for 1 hr. The reaction mixture was diluted with ethyl acetate, washed with water and saturated brine, dried over anhydrous sodium sulfate, and concentrated under reduced pressure. The residue was purified by column chromatography [developing solvent: ethyl acetate-methanol (20:1, volume ratio)] and crystallized from hexane to give the title compound (130 mg) as a colorless powder.

melting point 162-165° C.

$^1$H-NMR (300 MHz, CDCl$_3$) δ: 2.950 (⅓×3H, s), 2.989 (⅔×3H, s), 3.08-3.16 (2H, m), 4.093 (⅓×2H, s), 4.137 (⅔×2H, s), 4.22-4.28 (2H, m), 4.571 (2H, s), 7.11-7.21 (4H, m), 7.433 (2H, d, J=8.4 Hz), 7.434 (1H, s), 7.634 (2H, d, J=8.4 Hz), 7.635 (1H, s).

Example 28

N-(4-{2-[6-(4-chlorophenyl)-4-oxothieno[3,2-d]
pyrimidin-3(4H)-yl]ethyl}benzyl)-N,$N^2$-dimethylg-
lycinamide

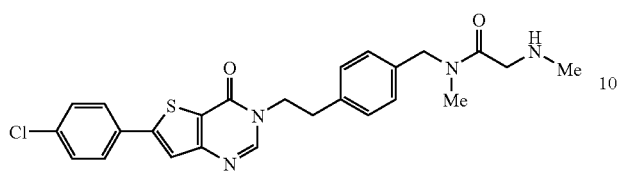

A mixture of the compound (0.12 g) obtained in Example 27, 40% methylamine in methanol solution (0.28 ml) and N,N-dimethylformamide (2 ml) was stirred at room temperature for 1 hr, diluted with ethyl acetate, washed with water and saturated brine, dried over anhydrous sodium sulfate, and concentrated under reduced pressure. The residue was recrystallized from ethyl acetate-hexane (1:1, volume ratio) to give the title compound (53 mg) as a colorless powder.
melting point 166-169° C.
Elemental analysis ($C_{25}H_{25}ClN_4O_2S$)
Calcd.: C, 62.42; H, 5.24; N, 11.65.
Found: C, 62.17; H, 5.13; N, 11.51.

Example 29

N-(4-{2-[6-(4-chlorophenyl)-4-oxothieno[3,2-d]
pyrimidin-3(4H)-yl]ethyl}benzyl)-N-methylglycine
tert-butyl ester

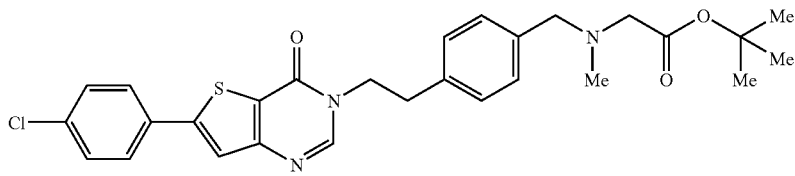

A mixture of the compound (200 mg) obtained in Example 4, tert-butyl bromoacetate (89 mg), triethylamine (146 mg) and N,N-dimethylformamide (3 ml) was stirred overnight at room temperature. The reaction mixture was diluted with ethyl acetate, washed with water and saturated brine, dried over anhydrous sodium sulfate, and concentrated under reduced pressure. The residue was purified by column chromatography [developing solvent:ethyl acetate-hexane (3:1, volume ratio)], and recrystallized from ethyl acetate-hexane (3:1, volume ratio) to give the title compound (156 mg) as a colorless powder.
melting point 130° C.
Elemental analysis ($C_{28}H_{30}ClN_3O_3S$)
Calcd.: C, 64.17; H, 5.77; N, 8.02.
Found: C, 63.96; H, 5.65; N, 8.11.

Example 30

N-(4-{2-[6-(4-chlorophenyl)-4-oxothieno[3,2-d]
pyrimidin-3(4H)-yl]ethyl}benzyl)-N-methylglycine
dihydrochloride

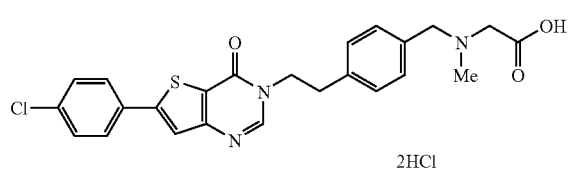

2HCl

A mixture of the compound (0.92 g) obtained in Example 29 and 4N hydrogen chloride-ethyl acetate solution was stirred at room temperature for 3 hr. The solvent was evaporated under reduced pressure, and the residue was washed with ethyl acetate to give the title compound (115 mg) as a colorless powder.
melting point 252-253° C.
Elemental analysis ($C_{24}H_{24}Cl_3N_3O_3S \cdot 0.1H_2O$)
Calcd.: C, 53.12; H, 4.49; N, 7.74.
Found: C, 52.82; H, 4.55; N, 7.52.

Example 31

$N^2$-(4-{2-[6-(4-chlorophenyl)-4-oxothieno[3,2-d]
pyrimidin-3(4H)-yl]ethyl}benzyl)-N,$N^2$-dimethylg-
lycinamide

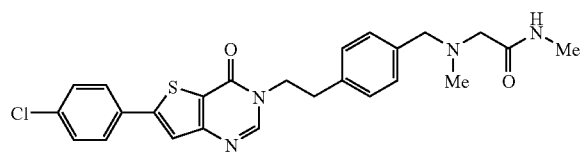

A mixture of the compound (70 mg) obtained in Example 30, 2N methylamine in tetrahydrofuran solution (0.65 ml), triethylamine (59 mg), bis(2-oxo-3-oxazolidinyl)phosphinoyl chloride (39 mg) and methylene chloride (5 ml) was stirred overnight at room temperature. The reaction mixture was diluted with ethyl acetate, washed with water and saturated brine, dried over anhydrous sodium sulfate, and concentrated is under reduced pressure. The residue was purified by column chromatography [developing solvent:ethyl acetate-methanol (10:1, volume ratio)] and recrystallized from ethyl acetate-hexane (1:1, volume ratio) to give the title compound (14 mg) as a colorless powder.
melting point 146-149° C.
Elemental analysis ($C_{25}H_{25}ClN_4O_2S \cdot 0.3H_2O$)
Calcd.: C, 61.73; H, 5.30; N, 11.52.
Found: C, 61.55; H, 5.14; N, 11.56.

Example 32

$N^2$-(4-{2-[6-(4-chlorophenyl)-4-oxothieno[3,2-d]
pyrimidin-3(4H)-yl]ethyl}benzyl)-$N^2$-methylglyci-
namide

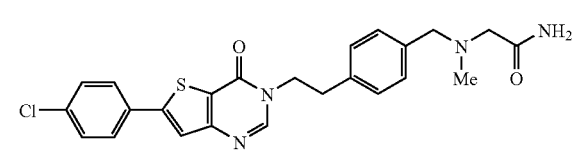

A mixture of the compound (100 mg) obtained in Example 4, bromoacetamide (31 mg), triethylamine (73 mg) and N,N-dimethylformamide (2 ml) was stirred overnight at room temperature. The reaction mixture was diluted with ethyl acetate, washed with water and saturated brine, dried over anhydrous sodium sulfate, and concentrated under reduced pressure. The residue was purified by column chromatography [developing solvent:ethyl acetate-methanol (10:1, volume ratio)] and recrystallized from ethyl acetate-hexane (1:1, volume ratio) to give the title compound (28 mg) as a colorless powder.
melting point 207-212° C.
Elemental analysis ($C_{24}H_{23}ClN_4O_2S \cdot 0.4H_2O$)
Calcd.: C, 60.79; H, 5.06; N, 11.82.
Found: C, 60.61; H, 4.90; N, 11.95.

Example 33

6-(4-chlorophenyl)-3-[2-(4-{[(4R)-4-hydroxy-2-oxopyrrolidin-1-yl]methyl}phenyl)ethyl]thieno[3,2-d]pyrimidin-4(3H)-one

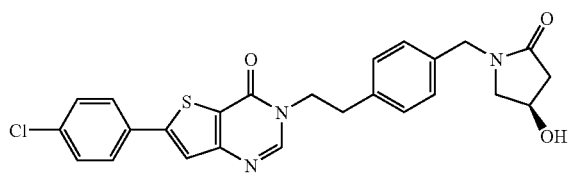

A mixture of methyl 5-(4-chlorophenyl)-3-(dimethylaminomethyleneamino)thiophene-2-carboxylate (54 mg), the compound (45 mg) obtained in Reference Example 23, N,N-diisopropylethylamine (24 mg) and ethanol (1 ml) was stirred overnight at 70° C. The reaction mixture was allowed to cool, ethyl acetate was added, and the precipitate was collected by filtration to give the title compound (69 mg) as a colorless powder.
melting point 243-246° C.
Elemental analysis ($C_{25}H_{22}ClN_3O_3S \cdot 0.1H_2O$)
Calcd.: C, 62.33; H, 4.64; N, 8.72.
Found: C, 62.09; H, 4.60; N, 8.75.

Example 34

1-(4-{2-[6-(4-chlorophenyl)-4-oxothieno[3,2-d]pyrimidin-3(4H)-yl]ethyl}benzyl)-4-ethylpiperazine-2,3-dione

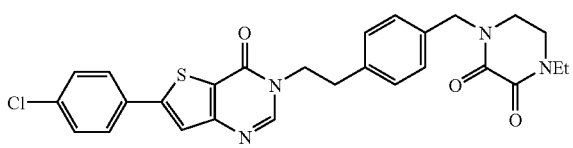

A mixture of methyl 5-(4-chlorophenyl)-3-(dimethylaminomethyleneamino)thiophene-2-carboxylate (62 mg), the compound (60 mg) obtained in Reference Example 24, N,N-diisopropylethylamine (25 mg) and ethanol (2 ml) was stirred overnight at 70° C. The reaction mixture was allowed to cool, ethyl acetate was added, and the precipitate was collected by filtration to give the title compound (82 mg) as a colorless powder.
melting point 285-288° C.
Elemental analysis ($C_{27}H_{25}ClN_4O_3S$)
Calcd.: C, 62.24; H, 4.84; N, 10.75.
Found: C, 62.16; H, 4.78; N, 10.90.

Example 35

6-(4-chlorophenyl)-3-(2-{4-[(3-oxopiperazin-1-yl)methyl]phenyl}ethyl)thieno[3,2-d]pyrimidin-4(3H)-one

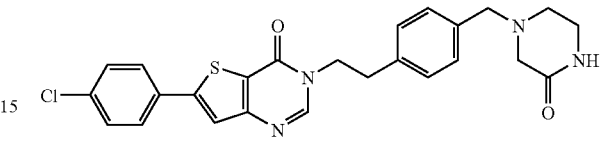

A mixture of methyl 5-(4-chlorophenyl)-3-(dimethylaminomethyleneamino)thiophene-2-carboxylate (69 mg), the compound (65 mg) obtained in Reference Example 25, N,N-diisopropylethylamine (60 mg) and ethanol (2 ml) was stirred overnight at 70° C. The reaction mixture was allowed to cool, ethyl acetate was added, and the precipitate was collected by filtration to give the title compound (89 mg) as a colorless powder.
melting point 232-234° C.
Elemental analysis ($C_{25}H_{23}ClN_4O_2S \cdot 0.4H_2O$)
Calcd.: C, 61.76; H, 4.93; N, 11.52.
Found: C, 61.48; H, 5.05; N, 11.67.

Example 36

N-[1-(4-{2-[6-(4-chlorophenyl)-4-oxothieno[3,2-d]pyrimidin-3(4H)-yl]ethyl}benzyl)pyrrolidin-3-yl]acetamide

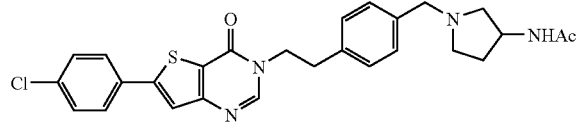

A mixture of methyl 5-(4-chlorophenyl)-3-(dimethylaminomethyleneamino)thiophene-2-carboxylate (0.15 g), the compound (0.16 g) obtained in Reference Example 26, N,N-diisopropylethylamine (0.19 g) and ethanol (3 ml) was stirred at 70° C. for 3 hr. The reaction mixture was allowed to cool, ethyl acetate was added, and the precipitate was collected by filtration to give the title compound (112 mg) as a colorless powder.
melting point 196-198° C.
Elemental analysis ($C_{27}H_{27}ClN_4O_2S$)
Calcd.: C, 63.96; H, 5.37; N, 11.05.
Found: C, 63.68; H, 5.34; N, 11.09.

Example 37 tert-butyl 4-(4-{2-[6-(4-chlorophenyl)-4-oxothieno[3,2-d]pyrimidin-3(4H)-yl]ethyl}benzyl)-3-oxopiperazine-1-carboxylate

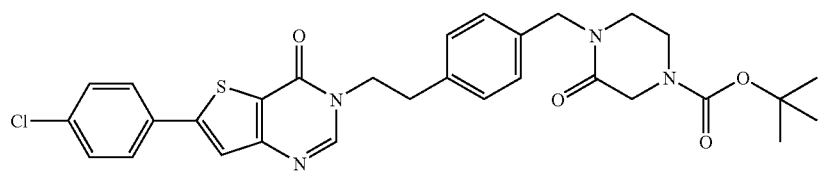

A mixture of methyl 5-(4-chlorophenyl)-3-(dimethylaminomethyleneamino)thiophene-2-carboxylate (136 mg), the compound (140 mg) obtained in Reference Example 29 and ethanol (3 ml) was stirred overnight at 60° C. The reaction mixture was allowed to cool, ethyl acetate was added, and the precipitate was collected by filtration to give the title compound (98 mg) as a colorless powder.

melting point 165-170° C.
Elemental analysis ($C_{30}H_{31}ClN_4O_4S \cdot 0.4H_2O$)
Calcd.: C, 61.46; H, 5.47; N, 9.56.
Found: C, 61.23; H, 5.31; N, 9.59.

Example 38

6-(4-chlorophenyl)-3-(2-{4-[(2-oxopiperazin-1-yl)methyl]phenyl}ethyl)thieno[3,2-d]pyrimidin-4(3H)-one dihydrochloride

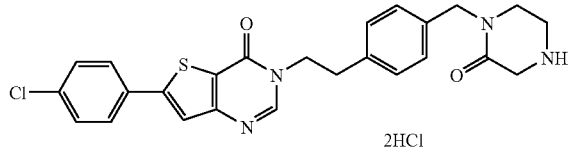

2HCl

4N Hydrogen chloride-ethyl acetate solution (6 ml) was added to the compound (75 mg) obtained in Example 37, and the mixture was stirred at room temperature for 1 hr. The solvent was evaporated under reduced pressure, and the residue was washed with ethyl acetate to give the title compound (72 mg) as a colorless powder.

melting point 271-278° C.
Elemental analysis ($C_{25}H_{25}Cl_3N_4O_2S \cdot 1.7H_2O$)
Calcd.: C, 51.55; H, 4.91; N, 9.62.
Found: C, 51.38; H, 5.06; N, 9.79.

Example 39

3-(2-{4-[(4-acetyl-2-oxopiperazin-1-yl)methyl]phenyl}ethyl)-6-(4-chlorophenyl)thieno[3,2-d]pyrimidin-4(3H)-one

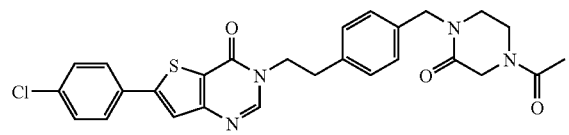

A mixture of the compound (30 mg) obtained in Example 38, acetyl chloride (4.7 mg), triethylamine (19 mg) and tetrahydrofuran (2 ml) was stirred at room temperature for 1 hr. The reaction mixture was diluted with ethyl acetate, washed with water and saturated brine, dried over anhydrous sodium sulfate, and concentrated under reduced pressure. The residue was recrystallized from ethyl acetate-hexane (1:1, volume ratio) to give the title compound (20 mg) as a colorless powder.

melting point 204-207° C.
Elemental analysis ($C_{27}H_{25}ClN_4O_3S \cdot 0.3H_2O$)
Calcd.: C, 61.60; H, 4.90; N, 10.64.
Found: C, 61.34; H, 4.89; N, 10.65.

Formulation Example 1

Production of Capsule

| | |
|---|---|
| 1) compound of Example 1 | 30 mg |
| 2) microcrystalline cellulose | 10 mg |
| 3) lactose | 19 mg |
| 4) magnesium stearate | 1 mg |
| Total | 60 mg |

The aforementioned 1), 2), 3) and 4) are mixed and filled in a gelatin capsule.

Formulation Example 2

Production of Tablet

| | |
|---|---|
| 1) compound of Example 1 | 30 g |
| 2) lactose | 50 g |
| 3) cornstarch | 15 g |
| 4) calcium carboxymethylcellulose | 44 g |
| 5) magnesium stearate | 1 g |
| 1000 tablets total | 140 g |

The total amount of the aforementioned 1), 2) and 3), and 30 g of 4) are kneaded with water and, after drying under reduced pressure, sized. The sized powder is mixed with 14 g of 4) and 1 g of 5), and punched out by a tabletting machine, whereby 1000 tablets containing 30 mg of the compound of Example 1 per tablet are obtained.

Experimental Example 1

Determination of Antagonistic Activity of Test Compound using GTPγS Binding Assay Using human SLC-1 expression CHO cell clone 57 and rat SLC-1 expression CHO cell clone 44 described in WO01/82925, SLC-1 expression CHO cell membrane fractions were prepared by the following method. In phosphate buffered saline (pH 7.4) supplemented with 5 mM EDTA (ethylenediaminetetraacetic acid) were suspended human and rat SLC-1 expression CHO cells ($1 \times 10^8$) and centrifuged. Homogenate buffer (10 ml, 10 mM $NaHCO_3$, 5 mM EDTA, pH 7.5) was added to the pellets of the cells and, using Polytron Homogenizer, the mixture was homogenated. The supernatant obtained after centrifugation at 400×g for 15 min was further centrifuged at 100,000×g for 1 hr to give precipitate of the membrane fraction. The precipitate was suspended in 2 ml of an assay buffer [50 mM Tris-HCl (pH 7.5), 1 mM EDTA, 0.1% BSA (bovine serum albumin), 10 mM $MgCl_2$, 100 mM NaCl, 1 μM GDP (guanosine 5'-diphosphate), 0.25 mM PMSF (phenylmethylsulfonyl fluoride), 1 mg/ml pepstatin, 20 mg/ml leupeptin, 10 mg/ml phosphoramidon] and centrifuged at 100,000×g for 1 hr. The membrane fraction recovered as precipitate was suspended again in 20 ml of an assay buffer, and after dispensing, preserved at −80° C. and used upon thawing each time when in use.

The antagonistic activity of the test compound was determined as follows. The SLC-1 expression CHO cell membrane fraction (171 μl) diluted with an assay buffer was dispensed to a polypropylene 96 well plate and $3 \times 10^{-10}$ M MCH (2 μl)

diluted with DMSO solution, test compound solution (2 μl) diluted to various concentrations and [$^{35}$S]-Guanosine 5'-(γ-thio)triphosphate (25 Daiichi Pure Chemicals Co., Ltd.) were respectively added (cell membrane final concentration: 20 μg/ml, [$^{35}$S]-Guanosine 5'-(γ-thio)triphosphate final concentration: 0.33 nM). The reaction mixture was reacted at 25° C. for 1 hr with stirring, suction filtered with a glass filter (GF-C) and washed 3 times with a wash solution (300 μl, 50 mM Tris-HCl buffer, pH 7.5). Liquid scintillator (50 ml) was added to the glass filter and the residual radioactivity was determined by a liquid scintillation counter.

Binding inhibition (%)=(radioactivity upon addition of test compound and MCH−radioactivity upon addition of DMSO solution)/(radioactivity upon addition of MCH−radioactivity upon addition of DMSO solution)×100

From the binding inhibition (%), IC$_{50}$ of the test compound was calculated.

The results are shown below.

| compound No. | inhibitory activity (IC$_{50}$: nM) |
|---|---|
| Example 1 | 0.3 |
| Example 2 | 0.4 |
| Example 4 | 0.4 |
| Example 6 | 4.8 |
| Example 9 | 4.7 |
| Example 11 | 3.2 |
| Example 18 | 1.2 |
| Example 22 | 10.0 |
| Example 32 | 5.0 |

INDUSTRIAL APPLICABILITY

The compound of the present invention has a superior MCH receptor antagonistic action, is useful as an agent for the prophylaxis or treatment of obesity and the like, and shows lower toxicity.

This application is based on a patent application No. 2005-132652 filed in Japan, the contents of which are incorporated in full herein by this reference.

The invention claimed is:

1. A compound represented by the formula:

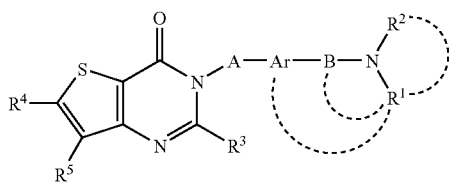

(I)

wherein
Ar is benzene or indane;
A is —(CH$_2$)$_2$—(CH$_2$)CO;
B is a bond, —CH$_2$—, —(CH$_2$)$_2$— or —CH(CH$_3$)—;
R$^3$ is a hydrogen atom or a hydroxy group;
R$^5$ is a hydrogen atom;
R$^4$ is 4-chlorophenyl or 4-fluorophenyl; and
R$^1$ and R$^2$ are each independently
(1) a hydrogen atom,
(2) a C$_{1-6}$ alkyl group optionally substituted by 1 to 3 substituents selected from halogen atom, carboxy group, hydroxy group, C$_{1-6}$ alkoxy-carbonyl group, and carbamoyl group optionally mono- or di-substituted by C$_{1-6}$ alkyl group;
(3) an amino group optionally substituted by 1 or 2 substituents selected from C$_{1-6}$ alkyl group, C$_{1-6}$ alkyl-carbonyl group, C$_{1-6}$ alkoxy-carbonyl group, C$_{6-14}$ aryl-carbonyl group, C$_{7-13}$ aralkyl-carbonyl group, C$_{1-6}$ alkylsulfonyl group, C$_{6-14}$ arylsulfonyl group and C$_{7-13}$ aralkylsulfonyl group;
(4) a C$_{1-6}$ alkyl-carbonyl group optionally substituted by 1 to 3 substituents selected from halogen atom, and amino group optionally mono- or di-substituted by C$_{1-6}$ alkyl group;
(5) a C$_{3-10}$ cycloalkyl-carbonyl group;
(6) a C$_{1-6}$ alkoxy-carbonyl group optionally substituted by 1 to 3 halogen atoms;
(7) a C$_{1-6}$ alkylsulfonyl group optionally substituted by 1 to 3 halogen atoms;
(8) a carbamoyl group optionally substituted by 1 or 2 substituents selected from C$_{1-6}$ alkyl group optionally substituted by 1 to 3 halogen atoms, C$_{6-14}$ aryl group and C$_{7-13}$ aralkyl group; or
(9) a thiocarbamoyl group optionally mono- or di-substituted by C$_{1-6}$ alkyl group optionally substituted by 1 to 3 halogen atoms, or
R$^1$ and R$^2$ are bonded to form piperidine, piperazine or pyrrolidine each optionally having 1 to 3 substituents selected from
(1) a halogen atom;
(2) a hydroxy group;
(3) an oxo group;
(4) a C$_{1-6}$ alkyl group optionally substituted by 1 to 3 substituents selected from halogen atom, carboxy group, hydroxy group, C$_{1-6}$ alkoxy-carbonyl group, and carbamoyl group optionally mono- or di-substituted by C$_{1-6}$ alkyl group;
(5) an amino group optionally substituted by 1 or 2 substituents selected from C$_{1-6}$ alkyl group, C$_{1-6}$ alkyl-carbonyl group, C$_{1-6}$ alkoxy-carbonyl group, C$_{6-14}$ aryl-carbonyl group, C$_{7-13}$ aralkyl-carbonyl group, C$_{1-6}$ alkylsulfonyl group, C$_{6-14}$ arylsulfonyl group and C$_{7-13}$ aralkylsulfonyl group;
(6) a C$_{1-6}$ alkyl-carbonyl group optionally substituted by 1 to 3 substituents selected from halogen atom, and amino group optionally mono- or di-substituted by C$_{1-6}$ alkyl group; and
(7) a C$_{1-6}$ alkoxy-carbonyl group optionally substituted by 1 to 3 halogen atoms, or R$^1$ and Ar are bonded to form benzazepane, or a salt thereof.

2. The compound of claim 1, wherein Ar is benzene or a salt thereof.

3. The compound of claim 1, wherein A is —(CH$_2$)$_2$—, or a salt thereof.

4. The compound of claim 1, wherein B is —CH$_2$—, or a salt thereof.

5. The compound of claim 1, wherein R$^3$ is a hydrogen atom, or a salt thereof.

6. The compound of claim 1, wherein R$^4$ is 4-chlorophenyl, or a salt thereof.

7. The compound of claim 1 or a salt thereof, which is
N-(4-{2-[6-(4-chlorophenyl)-4-oxothieno[3,2-d]pyrimidin-3(4H)-yl]ethyl}benzyl)-N-methylacetamide;
N-(4-{2-[6-(4-chlorophenyl)-4-oxothieno[3,2-d]pyrimidin-3(4H)-yl]ethyl}benzyl)-N,N',N'-trimethylthiourea;
6-(4-chlorophenyl)-3-[2-(4-{[(3S)-3-fluoropyrrolidin-1-yl]methyl}phenyl)ethyl]thieno[3,2-d]pyrimidin-4(3H)-one;
N'-[4-[2-[6-(4-chlorophenyl)-4-oxothieno[3,2-d]pyrimidin-3(4H)-yl]ethyl]phenyl]-N,N'-dimethylacetohydrazide; or
N$^2$-(4-{2-[6-(4-chlorophenyl)-4-oxothieno[3,2-d]pyrimidin-3(4H)-yl]ethyl}benzyl)-N$^2$-methylglycinamide,
or a salt thereof.

8. A pharmaceutical composition comprising the compound of claim 1 or a salt thereof, and a pharmacologically acceptable carrier.

* * * * *

UNITED STATES PATENT AND TRADEMARK OFFICE
CERTIFICATE OF CORRECTION

PATENT NO. : 7,989,445 B2  
APPLICATION NO. : 11/919301  
DATED : August 2, 2011  
INVENTOR(S) : T. Murata et al.

Page 1 of 1

It is certified that error appears in the above-identified patent and that said Letters Patent is hereby corrected as shown below:

Column 62, line 43, to Column 63, line 17:

Please delete the text beginning at column 62, line 43 of US 7,989,445, and ending at column 63, line 17.

Column 63, line 54, please correct:

"A is $-(CH_2)_2-(CH_2)CO;$"

to

"A is $-(CH_2)_2-$ or $-(CH_2)CO-;$"

Signed and Sealed this  
Twenty-second Day of November, 2011

David J. Kappos  
*Director of the United States Patent and Trademark Office*